(12) United States Patent
Kamerzell

(10) Patent No.: US 10,058,553 B2
(45) Date of Patent: Aug. 28, 2018

(54) FUSED HETEROTRICYCLIC ORGANIC COUMPOUNDS, PHARMACEUTICAL COMPOSITIONS, AND MEDICAL USES THEREOF

(71) Applicant: Alevere Medical Corporation, Broomfield, CO (US)

(72) Inventor: Tim Kamerzell, Overland Park, KS (US)

(73) Assignee: Alevere Medical Corporation, Broomfield, CO (US)

( * ) Notice: Subject to any disclaimer, the term of this patent is extended or adjusted under 35 U.S.C. 154(b) by 0 days.

(21) Appl. No.: 15/133,533

(22) Filed: Apr. 20, 2016

(65) Prior Publication Data

US 2016/0339029 A1    Nov. 24, 2016

Related U.S. Application Data

(63) Continuation of application No. PCT/US2014/061517, filed on Oct. 21, 2014.

(60) Provisional application No. 61/893,529, filed on Oct. 21, 2013, provisional application No. 61/893,544, filed on Oct. 21, 2013, provisional application No. 61/893,556, filed on Oct. 21, 2013, provisional application No. 61/893,564, filed on Oct. 21, 2013.

(51) Int. Cl.
| | | |
|---|---|---|
| *C07D 487/14* | (2006.01) | |
| *A61K 31/519* | (2006.01) | |
| *A61Q 19/06* | (2006.01) | |
| *A61K 31/4985* | (2006.01) | |
| *A61K 31/53* | (2006.01) | |
| *A61K 8/49* | (2006.01) | |
| *A61K 9/00* | (2006.01) | |
| *A61K 31/496* | (2006.01) | |
| *A61Q 19/00* | (2006.01) | |
| *A61K 31/4162* | (2006.01) | |

(52) U.S. Cl.
CPC .......... *A61K 31/519* (2013.01); *A61K 8/4946* (2013.01); *A61K 8/4953* (2013.01); *A61K 8/4966* (2013.01); *A61K 9/0019* (2013.01); *A61K 31/496* (2013.01); *A61K 31/4985* (2013.01); *A61K 31/53* (2013.01); *A61Q 19/00* (2013.01); *A61Q 19/06* (2013.01); *A61K 31/4162* (2013.01); *C07D 487/14* (2013.01)

(58) Field of Classification Search
CPC combination set(s) only.
See application file for complete search history.

(56) References Cited

U.S. PATENT DOCUMENTS

| | | | |
|---|---|---|---|
| 4,588,724 | A | 5/1986 | Greenway, III et al. |
| 7,943,187 | B2 | 5/2011 | Rabie |
| 8,491,947 | B2 | 7/2013 | Rabie |
| 8,513,310 | B2 | 8/2013 | Franchi et al. |
| 2005/0143347 | A1 | 6/2005 | Boderke et al. |
| 2005/0288354 | A1 | 12/2005 | Arnold et al. |
| 2008/0058287 | A1 | 3/2008 | Rose et al. |
| 2009/0143367 | A1 | 6/2009 | Malamas et al. |
| 2009/0162286 | A1 | 6/2009 | Black et al. |
| 2010/0063006 | A1 | 3/2010 | Duncan |
| 2010/0234295 | A1 | 9/2010 | Chen |
| 2011/0212889 | A1 | 9/2011 | Oral et al. |
| 2011/0218163 | A1 | 9/2011 | Rabie |
| 2016/0030389 | A1 | 2/2016 | Duncan et al. |

FOREIGN PATENT DOCUMENTS

| | | |
|---|---|---|
| WO | WO-2004/062389 A1 | 7/2004 |
| WO | WO-2005/009370 A2 | 2/2005 |
| WO | WO-2005/030756 A1 | 4/2005 |
| WO | WO-2007/011743 A2 | 1/2007 |
| WO | WO-2008/113421 A1 | 9/2008 |
| WO | WO-2010/138833 A1 | 12/2010 |
| WO | WO-2011/163389 A2 | 12/2011 |
| WO | WO-2012/108622 A1 | 8/2012 |
| WO | WO-2014/143125 A1 | 9/2014 |

OTHER PUBLICATIONS

Partial Supplementary Search Report from European Patent Office dated Sep. 21, 2016 for European Patent Application No. 13878099.4 (International Patent Application PCT/US2013/048368). (7 pages).
Chang, H.-P. et al. "Suppression of inflammation-associated factors by indole-3-carbinol in mice fed high-fat diets and in isolated, co-cultured macrophages and adipocytes," *Intl. J. Obesity* (2011) vol. 35, No. 12, pp. 1530-1538.
Caruso, M. K. et al. "An evaluation of mesotherapy solutions for inducing lipolysis and treating cellulite," *J. Plastic, Reconstructive and Aesthetic Surgery* (2008) vol. 61, No. 11, pp. 1321-1324.
International Search Report and Written Opinion for International Patent Application PCT/US2013/048368 dated Aug. 13, 2013. (9 pages).
Chang, H.-P. et al. "Antiobesity activities of indole-3-carbinol in high-fat-diet-induced obese mice," *Nutrition* (2011) vol. 27, No. 4, pp. 463-470.
International Search Report and Written Opinion for International Patent Application PCT/US2014/061517 dated Apr. 2, 2015. (14 pages).
PubChem Substance summary for CID AKOS003191731, Deposit Date Jun. 21, 2010.
Poirier, P. et al. "Obesity and Cardiovascular Disease: Pathophysiology, Evaluation, and Effect of Weight Loss," *Circulation* (2006) vol. 113, pp. 898-918.
STN Chemical Structure Search Results (dated Sep. 14, 2013). (1 page).
STN Chemical Structure Search Results (dated Sep. 14, 2013). (7 pages).
STN Chemical Structure Search Results (dated Sep. 14, 2013). (9 pages).

(Continued)

*Primary Examiner* — Nyeemah A Grazier
(74) *Attorney, Agent, or Firm* — Dechert LLP

(57) ABSTRACT

The invention provides fused heterocyclic organic compounds such as dihydropyrazolopyridotriazinones, compositions containing such compounds, medical kits, and methods for using such compounds and compositions for body contouring and/or reduction of fat in a subject.

11 Claims, 6 Drawing Sheets

(56) References Cited

OTHER PUBLICATIONS

Didenko, V. V. et al. "Regioselective and regiospecific reactions of ethyl ortho-[(dimethylamino)vinyl]azoloazinylcarboxylates with hydrazine," *Russian Journal of General Chemistry* (2010) vol. 80, No. 4, pp. 814-817. (abstract only).

Ciciani, G. et al. "Synthesis of new pyrazolo[5,1-c][1,2,4] benzotriazines, pyrazolo[5,1-c]pyrido[4,3-e][1,2,4] triazines and their open analogues as cytotoxic agents in normoxic and hypoxic conditions," *Bioorg. Med. Chem.* (2008) vol. 16, No. 21, pp. 9409-9419.

Afzal, O. et al. "Docking based virtual screening and molecular dynamics study to identify potential monoacylglycerol lipase inhibitors," *Bioorg. Med. Chem. Lett.* (2014) vol. 24, No. 16, pp. 3986-39996.

Extended European Search Report from European Patent Office dated May 16, 2017 for European Patent Application No. 14856633.4 (International Patent Application PCT/US2014/061517). (8 pages).

Registry Database, Chemical Abstracts Service (Columbus, OH) Registry No. 1208530-83-9, STN entry date: Mar. 10, 2010.

PubChem Substance summary for 3-(2-ethyl-6-oxo-3-phenylpyrazolo[5,1-c]pyrido[4,3-e][1,2,4]triazin-7(6H)-yl)propanoic acid. (Dated Dec. 22, 2014).

PubChem Substance summary for 2-methyl-3-phenyl-8,9-dihydro-7H-pyrazolo[5,1-c][1,2,4]benzotriazin-6-one. (Dated Dec. 22, 2014).

FUSED HETEROTRICYCLIC ORGANIC COUMPOUNDS, PHARMACEUTICAL COMPOSITIONS, AND MEDICAL USES THEREOF

CROSS REFERENCE TO RELATED APPLICATIONS

This application is a continuation of International Patent Application number PCT/US2014/061517 filed Oct. 21, 2014, which claims the benefit of and priority to U.S. Provisional Patent Application Ser. No. 61/893,529, filed Oct. 21, 2013; U.S. Provisional Patent Application Ser. No. 61/893,544, filed Oct. 21, 2013; U.S. Provisional Patent Application Ser. No. 61/893,556, filed Oct. 21, 2013; and U.S. Provisional Patent Application Ser. No. 61/893,564, filed Oct. 21, 2013; the contents of each of which are hereby incorporated by reference.

FIELD OF THE INVENTION

The invention provides fused heterocyclic organic compounds such as dihydropyrazolopyridotriazinones, compositions containing such compounds, medical kits, and methods for using such compounds and compositions for body contouring and/or reduction of fat in a subject.

BACKGROUND

Adipose tissue is composed mostly of adipocyte cells (i.e., fat cells), and the primary role of adipose tissue is the storage of energy in the form of lipids (e.g., triglycerides). Excessive amounts of adipose tissue in a subject can lead to disorders such as type 2 diabetes, inflammatory diseases, and cancer. Additionally, adipose tissue (i.e., body fat) can accumulate unevenly in the body and lead to undesirable fatty deposits. The energy stored in body fat can be utilized by breaking down the triglycerides in the body fat to liberate fatty acids through a process referred to as lipolysis. However, utilization of body fat may occur unevenly and the accumulation of fatty deposits in particular regions of the body can be cosmetically unappealing.

There are various reports in the literature of compositions used to reduce the amount of adipose tissue in a subject. Certain reports characterize the compositions as slimming agents for use in reducing the amount of adipose tissue in a particular area of the subject's body, such as the face or neck. For example, U.S. Pat. No. 8,513,310 is generally directed to cosmetic uses of phytosphingosine and cosmetic compositions containing this compound for use as a slimming agent. U.S. Patent Application Publication No. 2008/058287 is generally directed to a mesotherapy cream. U.S. Patent Application Publication No. 2010/063006 is generally directed to compositions and methods to reduce fat and retract skin. Also, U.S. Patent Application Publication No. 2011/218163 is generally directed to paeoniflorin preparations and uses thereof for fat reduction.

However, despite the progress reported in the literature for developing compositions that may be used as medicinal agents to reduce the accumulation of fat in a particular area of a subject's body, the need remains for compositions with improved ability to reduce the accumulation of fat in particular areas of a subject's body. The present invention addresses this need and provides other related advantages.

SUMMARY

The invention provides fused heterocyclic organic compounds such as dihydropyrazolopyridotriazinones, compositions containing such compounds, medical kits, and methods for using such compounds and compositions for body contouring and/or reduction of fat in a subject. The compounds and compositions can be used to reduce the amount of localized deposits of subcutaneous fat in a subject, such as subcutaneous deposits of fat in the vicinity of the subject's face, neck, chin, submental region, arm, stomach, or other body part. The compounds and compositions can also be used to treat medical disorders associated with local accumulation of fat, such as an adipose tissue tumor (e.g., a lipoma), fat embolism, or fatty liver disease. Pharmaceutical compositions, particularly injectable pharmaceutical compositions suited for cosmetic procedures, are provided. Various aspects of the invention are provided in more detail below.

One aspect of the invention provides a family of fused heterotricyclic organic compounds embraced by Formula I in Section II herein that may be used in the methods, compositions and kits described herein, wherein Formula I is represented by:

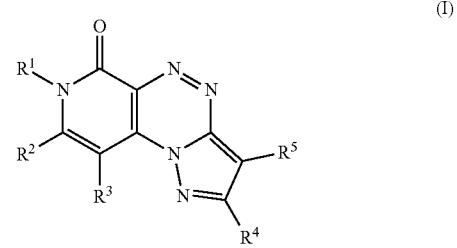

or a pharmaceutically acceptable salt thereof, wherein the variables are as defined in the detailed description.

Another aspect of the invention provides a cosmetic method of modifying the contour of a subject's externally exposed body part containing fat. The method comprises administering to said body part an amount of a fused heterotricyclic organic compound described herein, such as a compound of Formula I in Section II herein, effective to modify the contour of said body part.

Another aspect of the invention provides a method of reducing the amount of subcutaneous fat in a subject. The method comprises exposing subcutaneous fat in a subject to an effective amount of a fused heterotricyclic organic compound described herein, such as a compound of Formula I in Section II herein, to reduce the amount of subcutaneous fat in said subject.

Another aspect of the invention provides a method for inducing retraction of dermal tissue in a subject. The method comprises administering an effective amount of a fused heterotricyclic organic compound described herein, such as a compound of Formula I in Section II herein, to dermal tissue of a subject to induce retraction of dermal tissue.

Another aspect of the invention provides a method for inducing retraction of subcutaneous tissue in a subject. The method comprises administering an effective amount of a fused heterotricyclic organic compound described herein, such as a compound of Formula I in Section II herein, to subcutaneous tissue of a subject to induce retraction of subcutaneous tissue.

Another aspect of the invention provides a method of preventing the accumulation of fat in a subject. The method comprises administering to a subject in need thereof an effective amount of a fused heterotricyclic organic compound described herein, such as a compound of Formula I in Section II herein, to prevent accumulation of fat in the subject.

Another aspect of the invention provides a method of treating a disorder selected from the group consisting of an adipose tissue tumor, fat embolism, dyslipidemia, or fatty liver disease in a subject. The method comprises administering to a subject in need thereof a therapeutically effective amount of a fused heterotricyclic organic compound described herein, such as a compound of Formula I in Section II herein, to treat the disorder.

Another aspect of the invention provides a method of reducing the amount of fat or cholesterol in a subject. The method comprises administering to a subject in need thereof an effective amount of a fused heterotricyclic organic compound described herein, such as a compound of Formula I in Section II herein, to reduce the amount of fat or cholesterol in the subject.

Another aspect of the invention provides a method of reducing the amount of mesenchymal pre-adipocyte stem cell precursors in a subject. The method comprises administering to a subject in need thereof an effective amount of a fused heterotricyclic organic compound described herein, such as a compound of Formula I in Section II herein, to reduce the amount of mesenchymal pre-adipocyte stem cell precursors in the subject.

Another aspect of the invention provides a pharmaceutical composition, comprising a pharmaceutically acceptable carrier and a fused heterotricyclic organic compound described herein, such as a compound of Formula I in Section II herein.

Another aspect of the invention provides a family of dipyrido-pyrimidinone organic compounds embraced by Formula I in Section III herein that may be used in the methods, compositions and kits described herein, wherein Formula I is represented by:

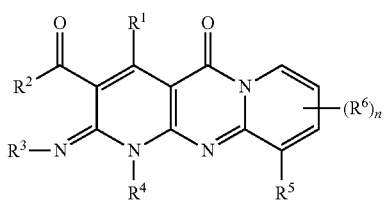

(I)

or a pharmaceutically acceptable salt thereof, wherein the variables are as defined in the detailed description.

Another aspect of the invention provides a cosmetic method of modifying the contour of a subject's externally exposed body part containing fat. The method comprises administering to said body part an amount of a dipyrido-pyrimidinone organic compound described herein, such as a compound of Formula I in Section III herein, effective to modify the contour of said body part.

Another aspect of the invention provides a method of reducing the amount of subcutaneous fat in a subject. The method comprises exposing subcutaneous fat in a subject to an effective amount of a dipyrido-pyrimidinone organic compound described herein, such as a compound of Formula I in Section III herein, to reduce the amount of subcutaneous fat in said subject.

Another aspect of the invention provides a method for inducing retraction of dermal tissue in a subject. The method comprises administering an effective amount of a dipyrido-pyrimidinone organic compound described herein, such as a compound of Formula I in Section III herein, to dermal tissue of a subject to induce retraction of dermal tissue.

Another aspect of the invention provides a method for inducing retraction of subcutaneous tissue in a subject. The method comprises administering an effective amount of a dipyrido-pyrimidinone organic compound described herein, such as a compound of Formula I in Section III herein, to subcutaneous tissue of a subject to induce retraction of subcutaneous tissue.

Another aspect of the invention provides a method of preventing the accumulation of fat in a subject. The method comprises administering to a subject in need thereof an effective amount of a dipyrido-pyrimidinone organic compound described herein, such as a compound of Formula I in Section III herein, to prevent accumulation of fat in the subject.

Another aspect of the invention provides a method of treating a disorder selected from the group consisting of an adipose tissue tumor, fat embolism, dyslipidemia, or fatty liver disease in a subject. The method comprises administering to a subject in need thereof a therapeutically effective amount of a dipyrido-pyrimidinone organic compound described herein, such as a compound of Formula I in Section III herein, to treat the disorder.

Another aspect of the invention provides a method of reducing the amount of fat or cholesterol in a subject. The method comprises administering to a subject in need thereof an effective amount of a dipyrido-pyrimidinone organic compound described herein, such as a compound of Formula I in Section III herein, to reduce the amount of fat or cholesterol in the subject.

Another aspect of the invention provides a method of reducing the amount of mesenchymal pre-adipocyte stem cell precursors in a subject. The method comprises administering to a subject in need thereof an effective amount of a dipyrido-pyrimidinone organic compound described herein, such as a compound of Formula I in Section III herein, to reduce the amount of mesenchymal pre-adipocyte stem cell precursors in the subject.

Another aspect of the invention provides a pharmaceutical composition, comprising a pharmaceutically acceptable carrier and a dipyrido-pyrimidinone organic compound described herein, such as a compound of Formula I in Section III herein.

Another aspect of the invention provides a family of tetrahydropyrimido-furo-isoquinolinone organic compounds embraced by Formula I in Section IV herein that may be used in the methods, compositions and kits described herein, wherein Formula I is represented by:

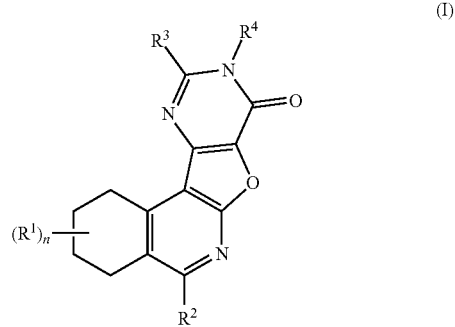

(I)

or a pharmaceutically acceptable salt thereof, wherein the variables are as defined in the detailed description.

Another aspect of the invention provides a cosmetic method of modifying the contour of a subject's externally exposed body part containing fat. The method comprises administering to said body part an amount of a tetrahydropyrimido-furo-isoquinolinone organic compound described herein, such as a compound of Formula I in Section IV herein, effective to modify the contour of said body part.

Another aspect of the invention provides a method of reducing the amount of subcutaneous fat in a subject. The method comprises exposing subcutaneous fat in a subject to an effective amount of a tetrahydropyrimido-furo-isoquinolinone organic compound described herein, such as a compound of Formula I in Section IV herein, to reduce the amount of subcutaneous fat in said subject.

Another aspect of the invention provides a method for inducing retraction of dermal tissue in a subject. The method comprises administering an effective amount of a tetrahydropyrimido-furo-isoquinolinone organic compound described herein, such as a compound of Formula I in Section IV herein, to dermal tissue of a subject to induce retraction of dermal tissue.

Another aspect of the invention provides a method for inducing retraction of subcutaneous tissue in a subject. The method comprises administering an effective amount of a tetrahydropyrimido-furo-isoquinolinone organic compound described herein, such as a compound of Formula I in Section IV herein, to subcutaneous tissue of a subject to induce retraction of subcutaneous tissue.

Another aspect of the invention provides a method of preventing the accumulation of fat in a subject. The method comprises administering to a subject in need thereof an effective amount of a tetrahydropyrimido-furo-isoquinolinone organic compound described herein, such as a compound of Formula I in Section IV herein, to prevent accumulation of fat in the subject.

Another aspect of the invention provides a method of treating a disorder selected from the group consisting of an adipose tissue tumor, fat embolism, dyslipidemia, or fatty liver disease in a subject. The method comprises administering to a subject in need thereof a therapeutically effective amount of a tetrahydropyrimido-furo-isoquinolinone organic compound described herein, such as a compound of Formula I in Section IV herein, to treat the disorder.

Another aspect of the invention provides a method of reducing the amount of fat or cholesterol in a subject. The method comprises administering to a subject in need thereof an effective amount of a tetrahydropyrimido-furo-isoquinolinone organic compound described herein, such as a compound of Formula I in Section IV herein, to reduce the amount of fat or cholesterol in the subject.

Another aspect of the invention provides a method of reducing the amount of mesenchymal pre-adipocyte stem cell precursors in a subject. The method comprises administering to a subject in need thereof an effective amount of a tetrahydropyrimido-furo-isoquinolinone organic compound described herein, such as a compound of Formula I in Section IV herein, to reduce the amount of mesenchymal pre-adipocyte stem cell precursors in the subject.

Another aspect of the invention provides a pharmaceutical composition, comprising a pharmaceutically acceptable carrier and a tetrahydropyrimido-furo-isoquinolinone organic compound described herein, such as a compound of Formula I in Section IV herein.

Another aspect of the invention provides a family of tetrahydrobenzo[4,5]imidazo[1,2-a]pyrazine organic compounds embraced by Formula I in Section V herein that may be used in the methods, compositions and kits described herein, wherein Formula I is represented by:

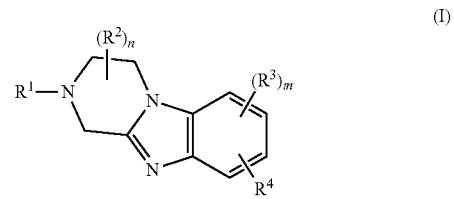

(I)

or a pharmaceutically acceptable salt thereof, wherein the variables are as defined in the detailed description.

Another aspect of the invention provides a cosmetic method of modifying the contour of a subject's externally exposed body part containing fat. The method comprises administering to said body part an amount of a tetrahydrobenzo[4,5]imidazo[1,2-a]pyrazine organic compound described herein, such as a compound of Formula I in Section V herein, effective to modify the contour of said body part.

Another aspect of the invention provides a method of reducing the amount of subcutaneous fat in a subject. The method comprises exposing subcutaneous fat in a subject to an effective amount of a tetrahydrobenzo[4,5]imidazo[1,2-a]pyrazine organic compound described herein, such as a compound of Formula I in Section V herein, to reduce the amount of subcutaneous fat in said subject.

Another aspect of the invention provides a method for inducing retraction of dermal tissue in a subject. The method comprises administering an effective amount of a tetrahydrobenzo[4,5]imidazo[1,2-a]pyrazine organic compound described herein, such as a compound of Formula I in Section V herein, to dermal tissue of a subject to induce retraction of dermal tissue.

Another aspect of the invention provides a method for inducing retraction of subcutaneous tissue in a subject. The method comprises administering an effective amount of a tetrahydrobenzo[4,5]imidazo[1,2-a]pyrazine organic compound described herein, such as a compound of Formula I in Section V herein, to subcutaneous tissue of a subject to induce retraction of subcutaneous tissue.

Another aspect of the invention provides a method of preventing the accumulation of fat in a subject. The method comprises administering to a subject in need thereof an effective amount of a tetrahydrobenzo[4,5]imidazo[1,2-a] pyrazine organic compound described herein, such as a compound of Formula I in Section V herein, to prevent accumulation of fat in the subject.

Another aspect of the invention provides a method of treating a disorder selected from the group consisting of an adipose tissue tumor, fat embolism, dyslipidemia, or fatty liver disease in a subject. The method comprises administering to a subject in need thereof a therapeutically effective amount of a tetrahydrobenzo[4,5]imidazo[1,2-a]pyrazine organic compound described herein, such as a compound of Formula I in Section V herein, to treat the disorder.

Another aspect of the invention provides a method of reducing the amount of fat or cholesterol in a subject. The method comprises administering to a subject in need thereof an effective amount of a tetrahydrobenzo[4,5]imidazo[1,2-a]pyrazine organic compound described herein, such as a compound of Formula I in Section V herein, to reduce the amount of fat or cholesterol in the subject.

Another aspect of the invention provides a method of reducing the amount of mesenchymal pre-adipocyte stem cell precursors in a subject. The method comprises administering to a subject in need thereof an effective amount of a tetrahydrobenzo[4,5]imidazo[1,2-a]pyrazine organic compound described herein, such as a compound of Formula I in Section V herein, to reduce the amount of mesenchymal pre-adipocyte stem cell precursors in the subject.

Another aspect of the invention provides a pharmaceutical composition, comprising a pharmaceutically acceptable carrier and a tetrahydrobenzo[4,5]imidazo[1,2-a]pyrazine organic compound described herein, such as a compound of Formula I in Section V herein.

DETAILED DESCRIPTION

Figure 1:
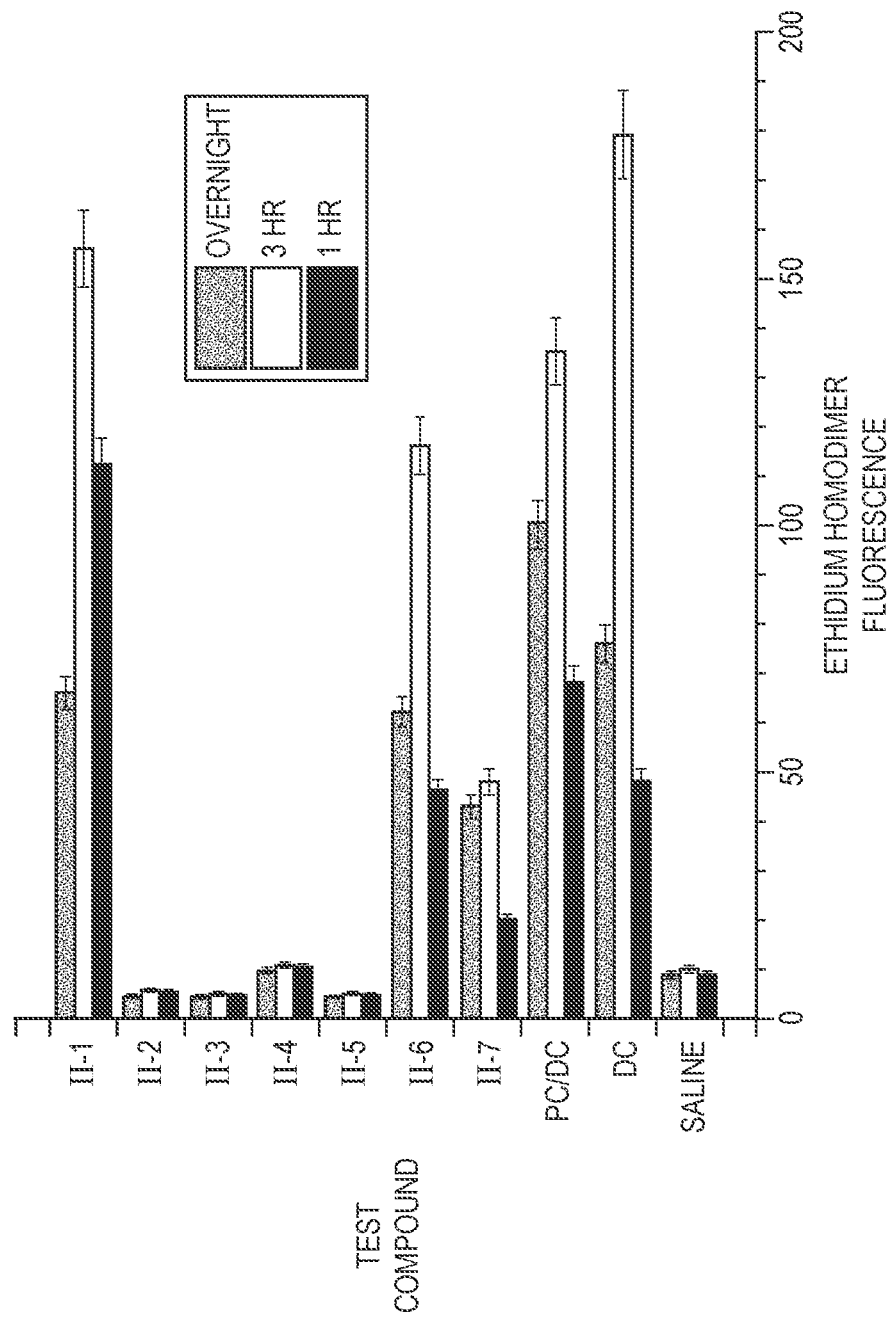
FIG. 1 is a histogram profile showing ethidium homodimer fluorescence intensity when adipocytes are incubated with 10 mg/mL of test compound or control for 1 hr, 3 hrs, or overnight, as described in Example 1.
Figure 2:
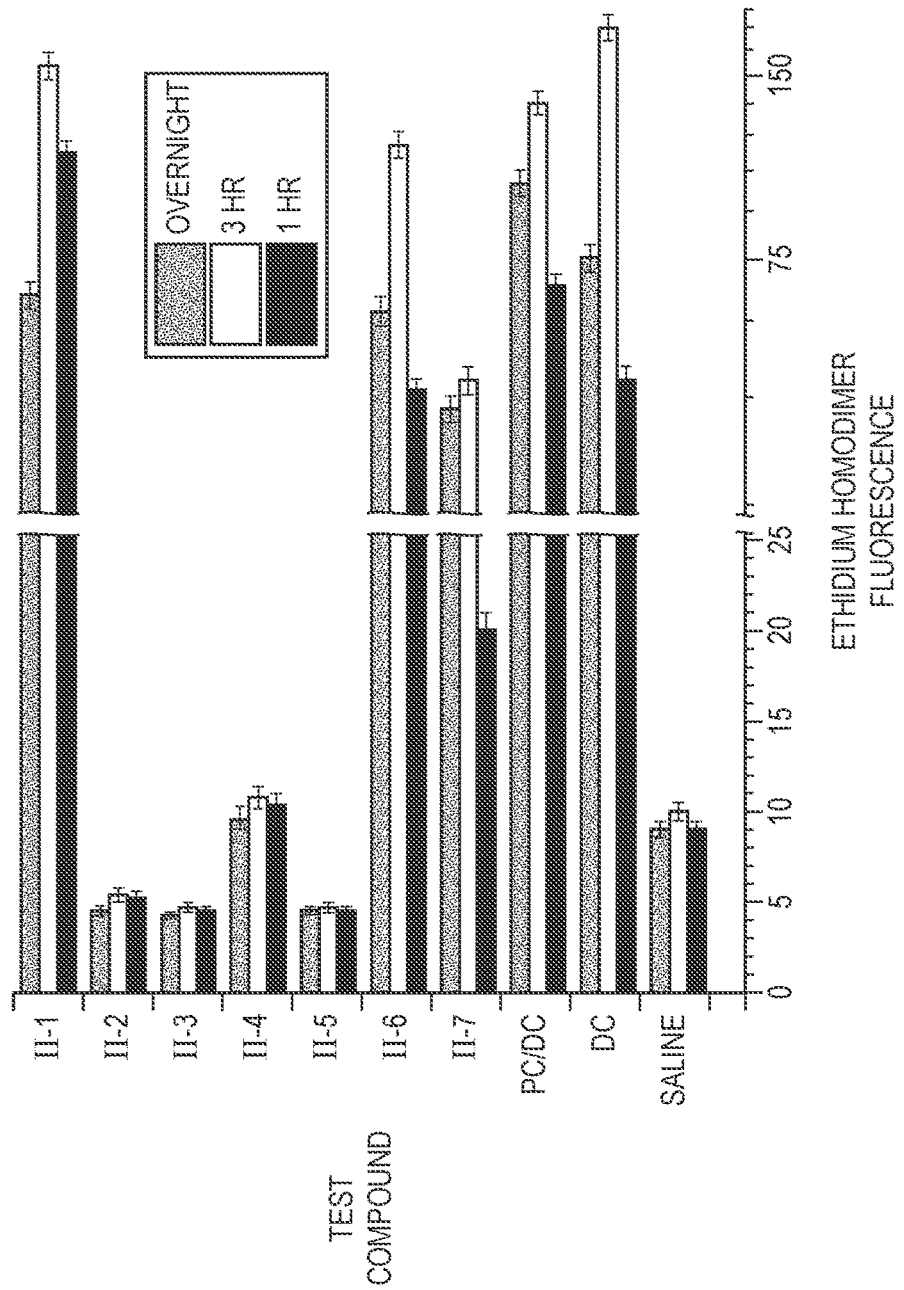
FIG. 2 is an expanded view of the histogram profile showing ethidium homodimer fluorescence intensity when adipocytes are incubated with 10 mg/mL of test compound or control for 1 hr, 3 hrs, or overnight, as described in Example 1.

The invention provides fused heterocyclic organic compounds such as dihydropyrazolopyridotriazinones, compositions containing such compounds, medical kits, and methods for using such compounds and compositions for body contouring and/or reduction of fat in a subject. The compounds and compositions can be used to reduce the amount of localized deposits of subcutaneous fat in a subject, such as subcutaneous deposits of fat in the vicinity of the subject's face, neck, chin, submental region, arm, stomach, or other body part. The compounds and compositions can also be used to treat medical disorders associated with local accumulations of fat, such as an adipose tissue tumor (e.g., a lipoma), fat embolism, or fatty liver disease. Pharmaceutical compositions, particularly injectable pharmaceutical compositions suited for cosmetic procedures, are provided. The practice of the present invention employs, unless otherwise indicated, conventional techniques of organic chemistry, pharmacology, cell biology, and biochemistry. Such techniques are explained in the literature, such as in "Comprehensive Organic Synthesis" (B. M. Trost & I. Fleming, eds., 1991-1992); "Current protocols in molecular biology" (F. M. Ausubel et al., eds., 1987, and periodic updates); and "Current protocols in immunology" (J. E. Coligan et al., eds., 1991), each of which is herein incorporated by reference in its entirety. Various aspects of the invention are set forth below in sections; however, aspects of the invention described in one particular section are not to be limited to any particular section.

I. Definitions

To facilitate an understanding of the present invention, a number of terms and phrases are defined below.

The terms "a" and "an" as used herein mean "one or more" and include the plural unless the context is inappropriate.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" refers to a diradical of an alkyl group. An exemplary alkylene group is —$CH_2CH_2$—.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclopentanes, cyclobutanes and cyclopropanes. Unless specified otherwise, cycloalkyl groups are optionally substituted at one or more ring positions with halogen, alkoxy, or alkyl. In certain embodiments, the cycloalkyl group is not substituted, i.e., it is unsubstituted.

The term "cycloalkylene" refers to a diradical of an cycloalkyl group. An exemplary cycloalkylene group is

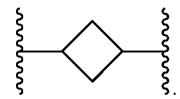

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. In certain embodiments, the aromatic ring is substituted at one or more ring positions with halogen, alkyl, hydroxyl, or alkoxyl. In certain other embodiments, the aromatic ring is not substituted, i.e., it is unsubstituted.

The term "aralkyl" refers to an alkyl group substituted with an aryl group.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. In certain embodiments, the heteroaryl ring is substituted at one or more ring positions with halogen, alkyl, hydroxyl, or alkoxyl. In certain other embodiments, the heteroaryl ring is not substituted, i.e., it is unsubstituted.

The term "heteroaralkyl" refers to an alkyl group substituted with a heteroaryl group.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" and "heterocyclic group" are art-recognized and refer to saturated or partially unsaturated 3- to 10-membered ring structures, alternatively 3- to 7-membered rings, whose ring structures include one to four heteroatoms, such as nitrogen, oxygen, and sulfur. The number of ring atoms in the heterocyclyl group can be specified using $C_x$-$C_x$ nomenclature where x is an integer specifying the number of ring atoms. For example, a $C_3$-$C_7$heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position. One example of a $C_3$heterocyclyl is aziridinyl. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the heterocyclcyl group is not substituted, i.e., it is unsubstituted.

The term "heterocycloalkyl" is art-recognized and refers to a saturated heterocyclyl group as defined above.

The terms "amine" and "amino" are art-recognized and refer to both unsubstituted and substituted amines, e.g., a moiety represented by the general formula —N($R^{50}$)($R^{51}$), wherein $R^{50}$ and $R^{51}$ each independently represent hydrogen, alkyl, cycloalkyl, heterocyclyl, alkenyl, aryl, aralkyl, or —(CH$_2$)$_m$—$R^{61}$; or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, $R^{50}$ and $R^{51}$ each independently represent hydrogen, alkyl, alkenyl, or —(CH$_2$)$_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—$R_{61}$, where m and $R_{61}$ are described above.

The term "carbamate" as used herein refers to a radical of the form —$R_g$OC(O)N($R_h$)—, —$R_g$OC(O)N($R_h$)$R_i$—, or —OC(O)N$R_h R_i$, wherein $R_g$, $R_h$ and $R_i$ are each independently alkoxy, aryloxy, alkyl, alkenyl, alkynyl, amide, amino, aryl, arylalkyl, carboxy, cyano, cycloalkyl, ester, ether, formyl, halogen, haloalkyl, heteroaryl, heterocyclyl, hydroxyl, ketone, nitro, sulfide, sulfonyl, or sulfonamide. Exemplary carbamates include arylcarbamates and heteroaryl carbamates, e.g., wherein at least one of $R_g$, $R_h$ and $R_i$ are independently aryl or heteroaryl, such as phenyl and pyridinyl.

The term "amide" or "amido" as used herein refers to a radical of the form —$R_a$C(O)N($R_b$)—, —$R_a$C(O)N($R_b$)$R_c$—, —C(O)N$R_b R_c$, or —C(O)NH$_2$, wherein $R_a$, $R_b$ and $R_c$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, and the like.

The term "sulfonamide" or "sulfonamido" as used herein refers to a radical having the structure —N($R_r$)—S(O)$_2$—$R_s$— or —S(O)$_2$—N($R_r$)$R_s$, where $R_r$ and $R_s$ can be, for example, hydrogen, alkyl, aryl, cycloalkyl, and heterocyclyl. Exemplary sulfonamides include alkylsulfonamides (e.g., where $R_s$ is alkyl), arylsulfonamides (e.g., where $R_s$ is aryl), cycloalkyl sulfonamides (e.g., where $R_s$ is cycloalkyl), and heterocyclyl sulfonamides (e.g., where $R_s$ is heterocyclyl), etc.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present invention. The symbol ═══ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The invention also encompasses isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed herein by substituting an isotopically labeled reagent for a non-isotopically labeled reagent.

The invention also encompasses solvates of compounds described herein. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin, *Remington's Pharmaceutical Sciences*, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. Fused Heterotricyclic Organic Compounds & Their Use

Certain aspects of the invention provide fused heterotricyclic organic compounds, pharmaceutical compositions containing such compounds, medical kits, and therapeutic applications using such compounds. These compounds, pharmaceutical compositions, medical kits, and therapeutic applications are described in more detail in the sections below.

A. Fused Heterotricyclic Organic Compounds

One aspect of the invention provides fused heterotricyclic organic compounds such as dihydropyrazolopyridotriazinones. The fused heterotricyclic organic compounds are contemplated to be useful in the methods, compositions, and kits described herein. In certain embodiments, the fused heterotricyclic organic compound is a compound embraced by Formula I:

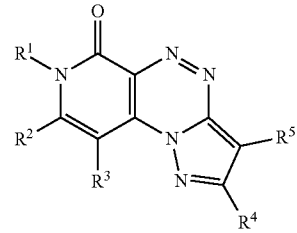

or a pharmaceutically acceptable salt thereof; wherein:

$R^1$ is —($C_1$-$C_6$)alkylene-$X^1$, —($C_3$-$C_6$)cycloalkyl-$X^1$, —$CO_2R^6$, —C(O)$R^6$, —OH, or —N($R^6$)C(O)—($C_1$-$C_6$) alkyl;

$X^1$ is —$CO_2R^6$, —C(O)$R^6$, —C(O)N($R^7$)$R^6$, —N($R^7$)C (O)$R^6$, or —$OR^6$;

$R^2$ and $R^3$ each represent independently hydrogen or —($C_1$-$C_6$)alkyl;

$R^4$ is hydrogen, —($C_1$-$C_6$)alkyl, —($C_3$-$C_7$)cycloalkyl, —($C_1$-$C_6$)alkoxy, or —($C_3$-$C_7$)cycloalkoxy;

$R^5$ is phenyl, 5-6 membered heteroaryl, —($C_3$-$C_7$)cycloalkyl, —($C_1$-$C_6$)alkoxy, or aralkyl, each of which is optionally substituted with 1, 2, or 3 substituents independently selected from the group consisting of halogen, —($C_1$-$C_6$)alkyl, —($C_3$-$C_5$)cycloalkyl, hydroxyl, and —($C_1$-$C_6$) alkoxy; or $R_5$ is hydrogen or —($C_1$-$C_6$)alkyl; and $R^6$ and $R^7$ each represent independently hydrogen or —($C_1$-$C_6$)alkyl.

In certain embodiments, $R^1$ is —($C_1$-$C_6$)alkylene-$X^1$ or —($C_3$-$C_6$)cycloalkyl-$X^1$. In certain other embodiments, $R^1$ is —($C_1$-$C_6$)alkylene-$X^1$. In certain other embodiments, $R^1$ is —($C_1$-$C_6$)alkylene-$CO_2R^6$. In certain other embodiments, $R^1$ is —($CH_2$)$_2$—$CO_2R^6$. In certain other embodiments, $R^1$ is —($C_1$-$C_6$)alkylene-$CO_2H$. In certain other embodiments, $R^1$ is —($CH_2$)$_2$—$CO_2H$. In certain other embodiments, $R^1$ is —($CH_2$)$_3$—$OCH_3$.

In certain embodiments, $X^1$ is —$CO_2R^6$ or —C(O)$R^6$. In certain other embodiments, $X^1$ is —$CO_2R^6$.

In certain embodiments, $R^2$ and $R^3$ are hydrogen.

In certain embodiments, $R^4$ —($C_1$-$C_6$)alkyl. In certain other embodiments, $R^4$ is methyl or ethyl. In certain other embodiments, $R^4$ is hydrogen.

In certain embodiments, $R^5$ is phenyl or a 5-6 membered heteroaryl, each of which is optionally substituted with 1, 2, or 3 substituents independently selected from the group consisting of halogen and —($C_1$-$C_6$)alkyl. In certain other embodiments, $R^5$ is phenyl optionally substituted with 1, 2, or 3 substituents independently selected from the group consisting of halogen and —($C_1$-$C_6$)alkyl. In certain other embodiments, $R^5$ is phenyl substituted with chloro, bromo, or fluoro. In certain embodiments, $R^5$ is phenyl substituted at the para-position with chloro or fluoro. In certain other embodiments, $R^5$ is phenyl. In certain embodiments, $R_5$ is —($C_1$-$C_6$)alkyl.

The description above describes multiple embodiments relating to compounds of Formula I. The patent application specifically contemplates all combinations of the embodiments. For example, the invention contemplates a compound of Formula I wherein $R^1$ is —($C_1$-$C_6$)alkylene-$X^1$, $X^1$ is —$CO_2R^6$, $R^2$ and $R^3$ are hydrogen, and $R^5$ is phenyl optionally substituted with 1, 2, or 3 substituents independently selected from the group consisting of halogen and —($C_1$-$C_6$)alkyl.

In certain embodiments, the compound is a compound of Formula I-A:

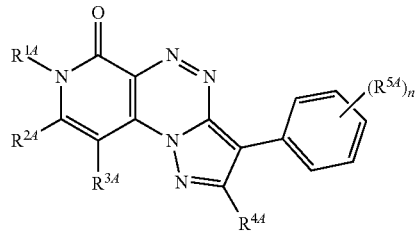

(I-A)

or a pharmaceutically acceptable salt thereof; wherein:

$R^{1A}$ is —($C_1$-$C_6$)alkylene-$CO_2R^{6A}$, —($C_3$-$C_6$)cycloalkyl-$CO_2R^{6A}$, —($C_1$-$C_6$)alkylene-O—($C_1$-$C_6$)alkyl, or —($C_3$-$C_6$)cycloalkyl-O—($C_1$-$C_6$)alkyl;

$R^{2A}$ and $R^{3A}$ each represent independently hydrogen or methyl;

$R^{4A}$ is hydrogen or —($C_1$-$C_6$)alkyl;

$R^{5A}$ represents independently for each occurrence hydrogen, halogen, or —($C_1$-$C_6$)alkyl;

$R^{6A}$ is hydrogen or —($C_1$-$C_6$)alkyl, and n is 1, 2, or 3.

In certain embodiments, $R^{1A}$ is —($C_1$-$C_6$)alkylene-$CO_2R^{6A}$. In certain embodiments, $R^{2A}$ and $R^{3A}$ are hydrogen. In certain embodiments, $R^{6A}$ is hydrogen. In certain embodiments, n is 1.

The description above describes multiple embodiments relating to compounds of Formula I-A. The patent application specifically contemplates all combinations of the embodiments.

In certain embodiments, the compound is one of the following or a pharmaceutically acceptable salt thereof:

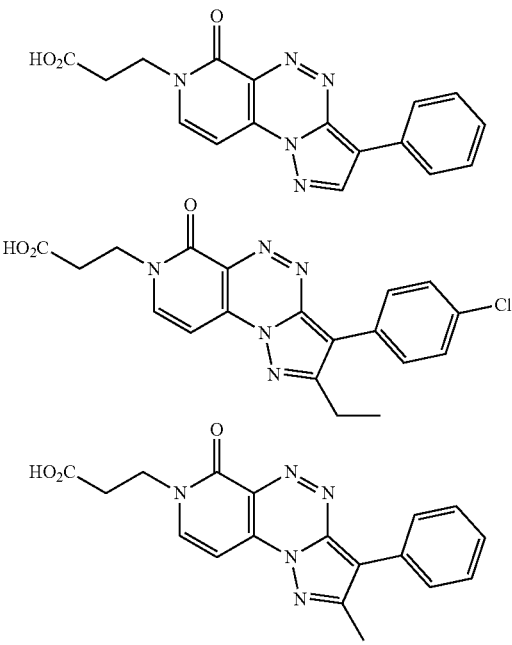

In certain other embodiments, the compound is one of the following or a pharmaceutically acceptable salt thereof:

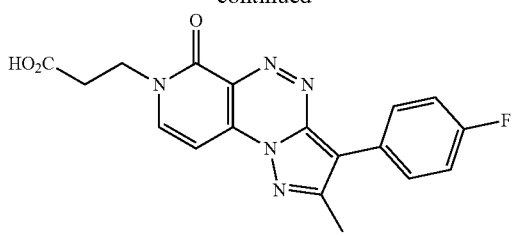

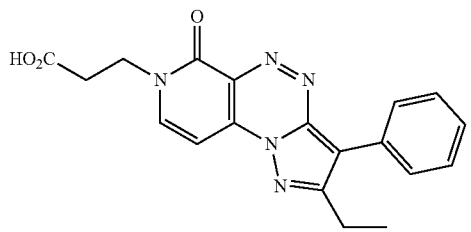

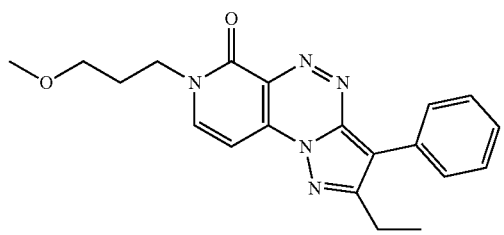

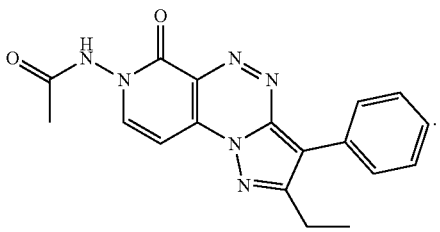

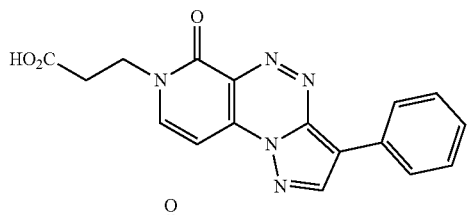

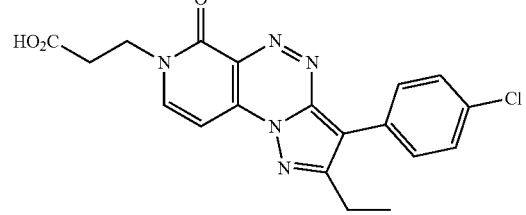

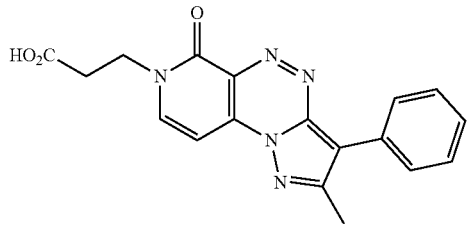

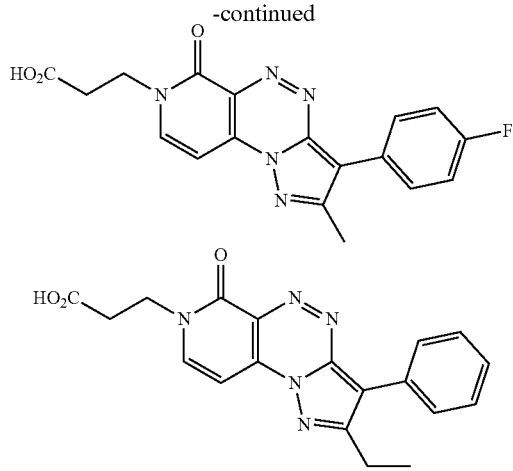
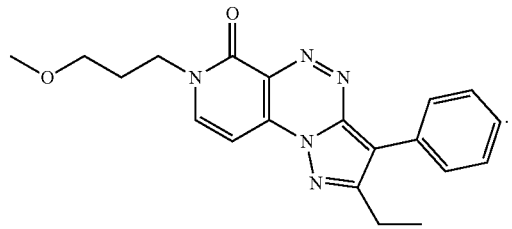

In certain other embodiments, the compound is one of the compounds listed in Table 1 below or a pharmaceutically acceptable salt thereof.

TABLE 1

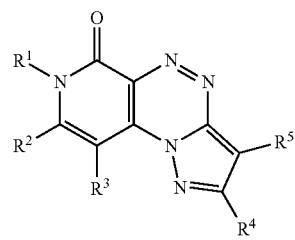

| Compound No. | $R^1$ | $R^2$ | $R^3$ | $R^4$ | $R^5$ |
|---|---|---|---|---|---|
| I-1 | —(CH$_2$)$_2$CO$_2$H | H | H | H | phenyl |
| I-2 | —(CH$_2$)$_2$CO$_2$Na | H | H | methyl | phenyl |
| I-3 | —(CH$_2$)$_2$CO$_2$H | H | H | ethyl | phenyl |
| I-4 | —(CH$_2$)$_2$CO$_2$H | H | H | ethyl | para-chloro-phenyl |
| I-5 | —(CH$_2$)$_2$CO$_2$H | H | H | methyl | para-fluoro-phenyl |
| I-6 | —(CH$_2$)$_3$OCH$_3$ | H | H | ethyl | phenyl |
| I-7 | —(CH$_2$)$_2$CO$_2$H | methyl | H | H | phenyl |
| I-8 | —(CH$_2$)$_2$CO$_2$H | H | methyl | H | phenyl |
| I-9 | —(CH$_2$)$_2$CO$_2$H | methyl | methyl | H | phenyl |
| I-10 | —(CH$_2$)$_2$CO$_2$H | H | H | cyclopropryl | phenyl |
| I-11 | —(CH$_2$)$_2$CO$_2$H | H | H | H | para-fluoro-phenyl |
| I-12 | —(CH$_2$)$_2$CO$_2$H | H | H | H | para-chloro-phenyl |
| I-13 | —(CH$_2$)$_2$CO$_2$H | H | H | H | meta-fluoro-phenyl |
| I-14 | —(CH$_2$)$_2$CO$_2$H | H | H | H | 3,5-difluorophenyl |
| I-15 | —(CH$_2$)$_2$CO$_2$H | H | H | H | 3,5-dimethylphenyl |
| I-16 | —(CH$_2$)$_2$CO$_2$H | H | H | H | 4-pyridyl |
| I-17 | —(CH$_2$)$_2$CO$_2$H | H | H | H | cyclohexyl |
| I-18 | —(CH$_2$)$_2$CO$_2$H | H | H | H | benzyl |
| I-19 | —(CH$_2$)$_2$CO$_2$H | H | H | H | para-methoxybenzyl |
| I-20 | —(CH$_2$)$_2$CO$_2$H | H | H | H | —(CH$_2$)$_2$C(H)(CH$_3$)$_2$ |
| I-21 | —(CH$_2$)$_3$CO$_2$H | H | H | H | phenyl |
| I-22 | —(CH$_2$)$_3$CO$_2$H | H | H | H | para-chloro-phenyl |
| I-23 | —(CH$_2$)$_3$CO$_2$H | H | H | H | meta-fluoro-phenyl |
| I-24 | —(CH$_2$)$_3$CO$_2$H | H | H | H | 3,5-difluorophenyl |
| I-25 | —(CH$_2$)$_3$CO$_2$H | H | H | H | 3,5-dimethylphenyl |
| I-26 | —(CH$_2$)$_3$CO$_2$H | H | H | H | 4-pyridyl |
| I-27 | —(CH$_2$)$_3$CO$_2$H | H | H | H | cyclohexyl |
| I-28 | —(CH$_2$)$_3$CO$_2$H | H | H | H | benzyl |
| I-29 | —(CH$_2$)$_3$CO$_2$H | H | H | H | para-methoxybenzyl |

TABLE 1-continued

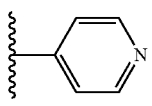

| Compound No. | R$^1$ | R$^2$ | R$^3$ | R$^4$ | R$^5$ |
|---|---|---|---|---|---|
| I-30 | —(CH$_2$)$_3$CO$_2$H | H | H | H | —(CH$_2$)$_2$C(H)(CH$_3$)$_2$ |
| I-31 | —(CH$_2$)$_2$CO$_2$CH$_3$ | H | H | H | phenyl |
| I-32 | —(CH$_2$)$_2$CO$_2$CH$_3$ | H | H | ethyl | para-chloro-phenyl |
| I-33 | —(CH$_2$)$_2$CO$_2$CH$_3$ | H | H | H | meta-fluoro-phenyl |
| I-34 | —(CH$_2$)$_2$CO$_2$CH$_3$ | H | H | H | 3,5-difluorophenyl |
| I-35 | —(CH$_2$)$_2$CO$_2$CH$_3$ | H | H | methyl | 3,5-dimethylphenyl |
| I-36 | —(CH$_2$)$_2$CO$_2$CH$_3$ | H | H | H | 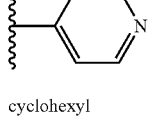 |
| I-37 | —(CH$_2$)$_2$CO$_2$CH$_3$ | H | H | H | cyclohexyl |
| I-38 | —(CH$_2$)$_2$CO$_2$CH$_3$ | H | H | methyl | benzyl |
| I-39 | —(CH$_2$)$_2$CO$_2$CH$_3$ | H | H | H | para-methoxybenzyl |
| I-40 | —(CH$_2$)$_2$CO$_2$CH$_3$ | H | H | methyl | —(CH$_2$)$_2$C(H)(CH$_3$)$_2$ |
| I-41 | —(CH$_2$)$_2$C(O)NH$_2$ | H | H | H | phenyl |
| I-42 | —(CH$_2$)$_2$C(O)NH$_2$ | H | H | ethyl | para-chloro-phenyl |
| I-43 | —(CH$_2$)$_2$C(O)NH$_2$ | H | H | H | meta-fluoro-phenyl |
| I-44 | —(CH$_2$)$_2$C(O)NH$_2$ | H | H | H | 3,5-difluorophenyl |
| I-45 | —(CH$_2$)$_2$C(O)NH$_2$ | H | H | methyl | 3,5-dimethylphenyl |
| I-46 | —(CH$_2$)$_3$OH | H | H | H | 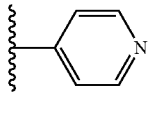 |
| I-47 | —(CH$_2$)$_3$OH | H | H | H | cyclohexyl |
| I-48 | —(CH$_2$)$_3$OH | H | H | methyl | benzyl |
| I-49 | —(CH$_2$)$_3$OH | H | H | H | para-methoxybenzyl |
| I-50 | —(CH$_2$)$_3$OH | H | H | methyl | —(CH$_2$)$_2$C(H)(CH$_3$)$_2$ |
| I-51 | —C(H)(CH$_3$)CO$_2$H | H | H | H | phenyl |
| I-52 | —C(H)(CH$_3$)CO$_2$H | H | H | H | para-chloro-phenyl |
| I-53 | —C(H)(CH$_3$)CO$_2$H | H | H | H | meta-fluoro-phenyl |
| I-54 | —C(H)(CH$_3$)CO$_2$H | H | H | H | 3,5-difluorophenyl |
| I-55 | —C(H)(CH$_3$)CO$_2$H | H | H | H | 3,5-dimethylphenyl |
| I-56 | —(CH$_2$)—C(H)(CH$_3$)CO$_2$H | H | H | H | 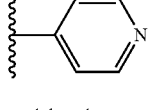 |
| I-57 | —(CH$_2$)—C(H)(CH$_3$)CO$_2$H | H | H | H | cyclohexyl |
| I-58 | —(CH$_2$)—C(H)(CH$_3$)CO$_2$H | H | H | H | benzyl |
| I-59 | —(CH$_2$)—C(H)(CH$_3$)CO$_2$H | H | H | H | para-methoxybenzyl |
| I-60 | —(CH$_2$)—C(H)(CH$_3$)CO$_2$H | H | H | H | —(CH$_2$)$_2$C(H)(CH$_3$)$_2$ |
| I-61 | —(CH$_2$)$_2$C(O)CH$_3$ | H | H | H | phenyl |
| I-62 | —(CH$_2$)$_2$C(O)CH$_3$ | H | H | ethyl | para-chloro-phenyl |
| I-63 | —(CH$_2$)$_2$C(O)CH$_3$ | H | H | H | meta-fluoro-phenyl |
| I-64 | —(CH$_2$)$_2$C(O)CH$_3$ | H | H | H | 3,5-difluorophenyl |
| I-65 | —(CH$_2$)$_2$C(O)CH$_3$ | H | H | methyl | 3,5-dimethylphenyl |
| I-66 | —(CH$_2$)$_2$C(O)CH$_3$ | H | H | H | 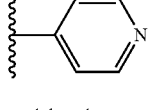 |
| I-67 | —(CH$_2$)$_2$C(O)CH$_3$ | H | H | H | cyclohexyl |
| I-68 | —(CH$_2$)$_2$C(O)CH$_3$ | H | H | methyl | benzyl |
| I-69 | —(CH$_2$)$_2$C(O)CH$_3$ | H | H | H | para-methoxybenzyl |
| I-70 | —(CH$_2$)$_2$C(O)CH$_3$ | H | H | methyl | —(CH$_2$)$_2$C(H)(CH$_3$)$_2$ |
| I-71 | OH | H | H | H | H |
| I-72 | OH | H | H | methyl | H |

TABLE 1-continued

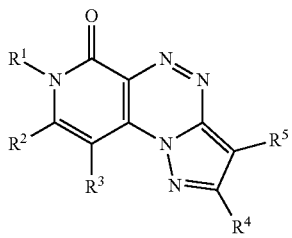

| Compound No. | R¹ | R² | R³ | R⁴ | R⁵ |
|---|---|---|---|---|---|
| I-73 | $CO_2H$ | H | H | H | H |
| I-74 | $CO_2H$ | H | H | methyl | H |
| I-75 | —C(H)(CH₃)CO₂H | H | H | H | H |

Methods for preparing compounds described herein are illustrated in the following synthetic schemes. These schemes are given for the purpose of illustrating the invention, and should not be regarded in any manner as limiting the scope or the spirit of the invention. Starting materials shown in the schemes can be obtained from commercial sources or can be prepared based on procedures described in the literature.

The synthetic route illustrated in Scheme II-1 depicts exemplary procedures for preparing esters, aldehydes, alcohols, and ketone containing compounds starting from commercially available carboxylic acid A. In the first step, commercially available carboxylic acid A is subjected to an esterification reaction with alcohol R'OH to produce ester compound B. Esterification reactions are well known in the literature and such reactions are often performed using an acid catalyst, such as hydrochloric acid. Selective reduction of the ester group in compound B using, for example, lithium borohydride, provides alcohol C. To the extent an aldehyde compound is desired, alcohol C can be oxidized using procedures known in the literature for converting a hydroxyl group to an aldehyde, such as oxidation using Dess-Martin Periodinane, to provide aldehyde D. Further, to the extent a ketone compound is desired, aldehyde D can be reacted with an activated carbon nucleophile, such as R"MgCl, to form a secondary alcohol (not shown) that is then oxidized using procedures known in the literature, such as Dess-Martin Periodinane, to form ketone compound E. Further description of functional group conversation procedures are described in, for example, "Comprehensive Organic Synthesis" (B. M. Trost & I. Fleming, eds., 1991-1992); Carey, F. A. and Sundberg, R. J. Advanced Organic Chemistry Part B: Reactions and Synthesis, 3$^{rd}$ Ed.; Plenum Press: New York, 1990; and J. March, Advanced Organic Chemistry, McGraw Hill Book Company, New York, (1992, 4$^{th}$ edition). It is also appreciated that if a particular compound contains a functional group sensitive to one or more of the synthetic transformations described herein, then conventional protecting group strategies are contemplated to be applied. For a description of protecting group strategies and procedures, see, for example, Greene, T. W.; Wuts, P. G. M. Protective Groups in Organic Synthesis, 2nd ed.; Wiley, New York, 1991.

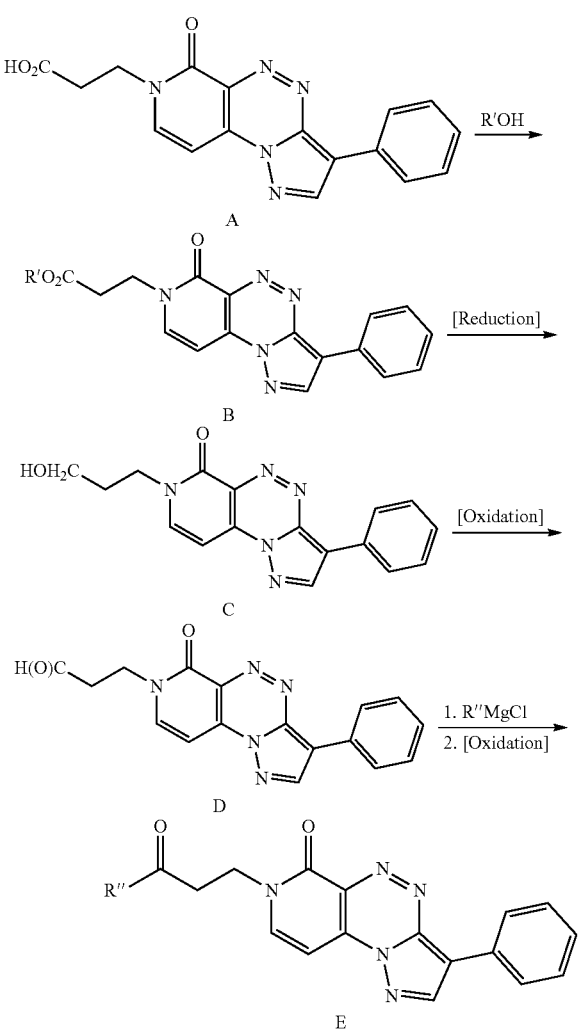

SCHEME II-1.

R' is alkyl;
R" is alkyl.

Synthetic procedures in Scheme II-2 illustrate how chemical groups can be added to the eastern portion of the fused heterotricyclic core. For example, palladium coupling procedures can be used to react heteroaromatic bromide A1 with a boronic acid containing the desired aromatic group, such as an optionally substituted phenyl group or an optionally substituted 5-6 membered heteroaromatic group, to provide compound B1. A specific illustration of this synthetic procedure is provided in Scheme II-3 where the first reaction sequence shows a para-methylphenyl group being attached to the fused heterotricyclic core to provide compound B2 and the second reaction sequence shows a methylpyridinyl group being attached to the fused tricyclic core to provide compound C2. One advantage of the palladium coupling approach is that a large number of variously substituted aryl and heteroaromatic boronic acids are commercially available or may be easily prepared using procedures described in the literature.

procedures described in, for example, B. R. Kim et al. in *Synthesis,* 2012, 42-50, provides amide C3.

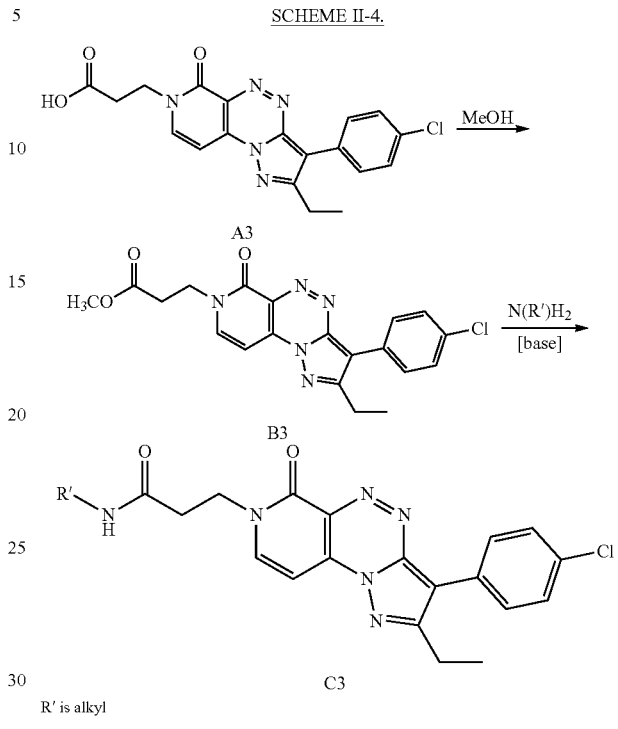

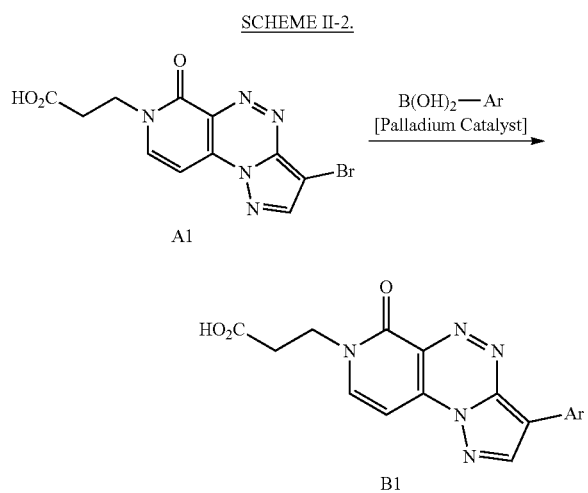

Synthetic procedures in Scheme II-5 illustrate how chemical groups can be added to the western portion of the fused heterotricyclic core. For example, reaction of amide A4 with

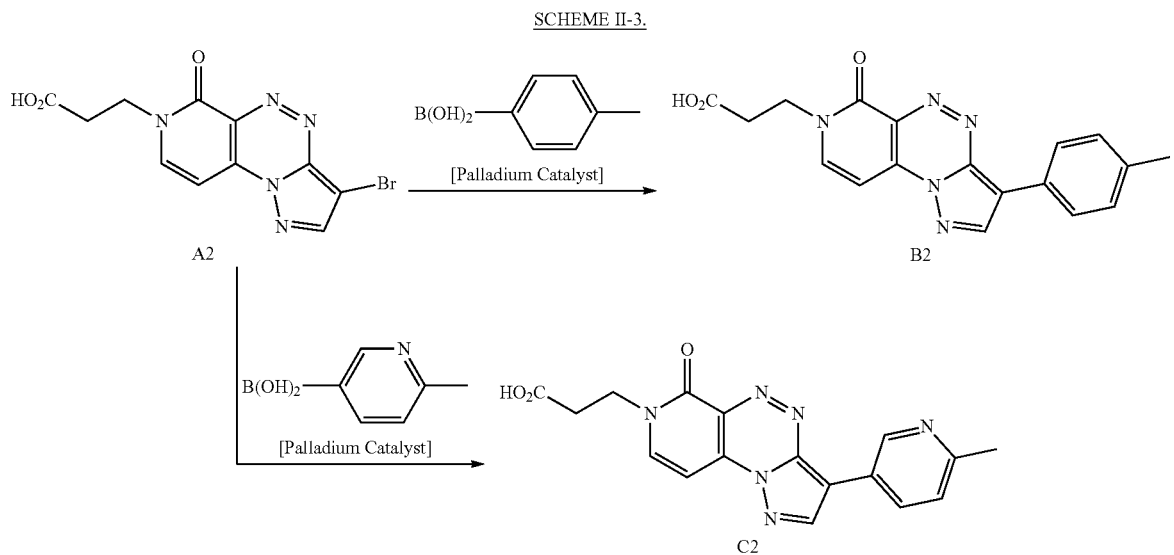

Scheme II-4 illustrates procedures for preparing amides. Commercially available carboxylic acid A3 is subjected to esterification according to standard literature procedures using methanol to provide ester compound B3. Reaction of ester B3 with amine N(R')H₂ (where R' is alkyl) in the presence of a base (e.g., potassium t-butoxide) according to base (e.g., tert-butyl lithium) provides an organolithium intermediate (not shown) that will undergo reaction with epoxide B4 to provide alcohol C4. Oxidation of alcohol C4 using standard procedures from the literature, such as Dess-Martin Periodinane, provides ketone compound D4. Selective reduction of ketone D4 using procedures from the literature (e.g., tosylhydrazine and catechol borane) provides alkane E4. Removal of the protecting group (Pg) (e.g., by TBAF when Pg is tert-butyldimethylsilyl) provides alcohol F4, which can be oxidized to carboxylic acid G4 using oxidation procedures described in the literature. For additional discussion of oxidation, reduction, and protecting group removal procedures, see, for example, "Comprehensive Organic Synthesis" (B. M. Trost & I. Fleming, eds., 1991-1992); Carey, F. A. and Sundberg, R. J. Advanced Organic Chemistry Part B: Reactions and Synthesis, $3^{rd}$ Ed.; Plenum Press: New York, 1990; J. March, Advanced Organic Chemistry, McGraw Hill Book Company, New York, (1992, $4^{th}$ edition); and Greene, T. W.; Wuts, P. G. M. *Protective Groups in Organic Synthesis,* 2nd ed.; Wiley, New York, 1991.

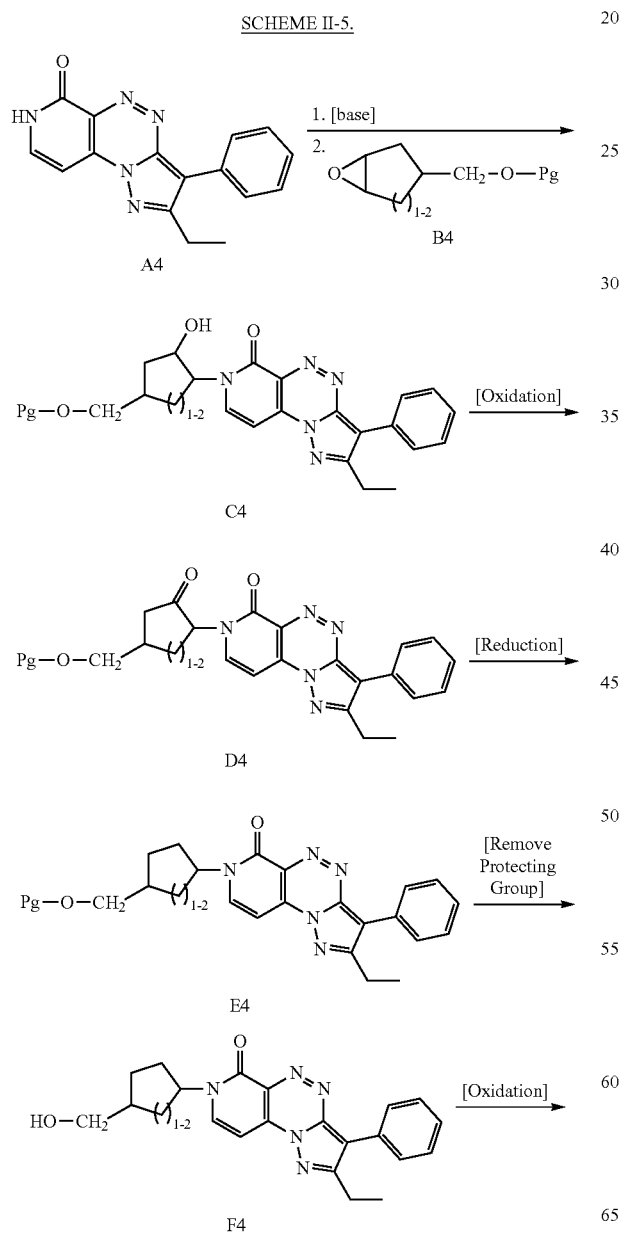

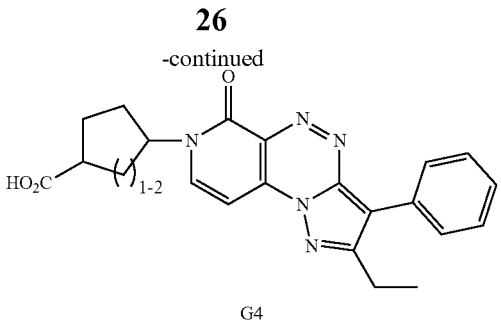

B. Therapeutic Applications of Fused Heterotricyclic Organic Compounds

The invention provides methods for body contouring and/or reduction of fat in a subject using the fused heterotricyclic organic compounds and pharmaceutical compositions described herein. Methods include the use of fused heterotricyclic organic compounds described herein as stand-alone therapeutic agents and/or as part of a combination therapy with another medicinal agent.

Cosmetic Methods of Modifying the Contour of a Subject's Externally Exposed Body Part One aspect of the invention provides a method of modifying the contour of a subject's externally exposed body part containing fat. The method comprises administering to said body part an amount of a fused heterotricyclic organic compound described herein, such as a compound of Formula I described above in Sub-Section A, effective to modify the contour of said body part. Formula I, as described above in Sub-Section A, is represented by:

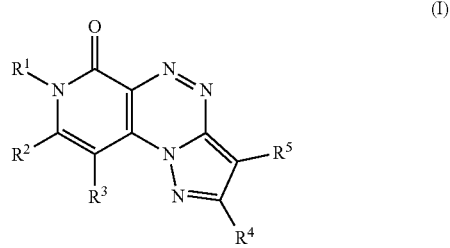

or a pharmaceutically acceptable salt thereof, wherein the variables are as defined above in Sub-Section A.

In certain embodiments, the externally exposed body part containing fat is the subject's face, neck, chin, submental region, arm, thigh, knee, calf, buttocks, hips, or abdomen. In certain other embodiments, the externally exposed body part containing fat is the subject's face. In certain other embodiments, the externally exposed body part containing fat is the subject's chin or cheek. In certain embodiments, the externally exposed body part is the subject's neck.

In certain embodiments, the subject experiences at least a 5% by weight reduction in the amount of fat in the subject's body part exposed to said compound. In certain other embodiments, the subject experiences at least a 10% by weight reduction in the amount of fat in the subject's body part exposed to said compound. In certain embodiments, the subject experiences at least a 15% by weight reduction in the amount of fat in the subject's body part exposed to said compound. In certain other embodiments, the subject experiences at least a 25% by weight reduction in the amount of fat in the subject's body part exposed to said compound. In certain other embodiments, the subject experiences from about 1% to about 10%, about 10% to about 20%, about 20% to about 40%, about 40% to about 60%, about 60% to about 80%, about 1% to about 30%, or about 1% to about 50% by weight reduction in the amount of fat in the subject's body part exposed to said compound.

In certain embodiments, the administering comprises injecting said compound into said body part.

In certain embodiments, the subject is an adult human. In certain embodiments, the subject is an animal, such as dog or cat.

In certain embodiments, the compound is one of the generic or specific compounds described above in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing the Amount of Subcutaneous Fat

Another aspect of the invention provides a method of reducing the amount of subcutaneous fat in a subject. The method comprises exposing subcutaneous fat in a subject to an effective amount of a fused heterotricyclic organic compound described herein, such as a compound of Formula I described above in Sub-Section A, to reduce the amount of subcutaneous fat in said subject. Formula I, as described above in Sub-Section A, is represented by:

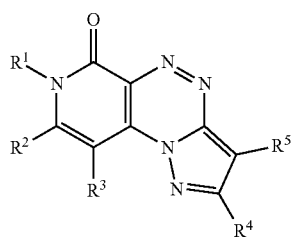

(I)

or a pharmaceutically acceptable salt thereof, wherein the variables are as defined above in Sub-Section A.

In certain embodiments, the subcutaneous fat is located in the subject's face, neck, chin, submental region, arm, thigh, knee, calf, buttocks, hips, or abdomen. In certain other embodiments, the subcutaneous fat is located in subject's face. In certain other embodiments, the subcutaneous fat is located in subject's neck.

In certain embodiments, the subject experiences at least a 5% by weight reduction in the amount of subcutaneous fat in the subject's body part exposed to said compound. In certain other embodiments, the subject experiences at least a 10% by weight reduction in the amount of subcutaneous fat in the subject's body part exposed to said compound. In certain embodiments, the subject experiences at least a 15% by weight reduction in the amount of subcutaneous fat in the subject's body part exposed to said compound. In certain other embodiments, the subject experiences at least a 25% by weight reduction in the amount of subcutaneous fat in the subject's body part exposed to said compound. In certain other embodiments, the subject experiences 1% to about 10%, about 10% to about 20%, about 20% to about 40%, about 40% to about 60%, about 60% to about 80%, about 1% to about 30%, or about 1% to about 50% by weight reduction in the amount of subcutaneous fat in the subject's body part exposed to said compound.

In certain embodiments, said exposing comprises injecting said compound of Formula I into a region of subcutaneous fat.

In certain embodiments, the subject is an adult human.

In certain embodiments, the compound is one of the generic or specific compounds described above in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Inducing Retraction of Dermal Tissue

Another aspect of the invention provides a method for inducing retraction of dermal tissue in a subject. The method comprises administering an effective amount of a fused heterotricyclic organic compound described herein, such as a compound of Formula I described above in Sub-Section A, to dermal tissue of a subject to induce retraction of dermal tissue. Formula I, as described above in Sub-Section A, is represented by:

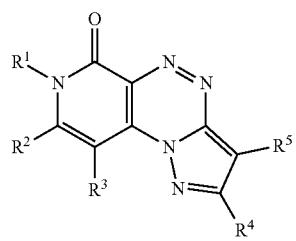

(I)

or a pharmaceutically acceptable salt thereof, wherein the variables are as defined above in Sub-Section A.

In certain embodiments, said administering comprises injecting said compound into dermal tissue.

In certain embodiments, the subject is an adult human.

In certain embodiments, the compound is one of the generic or specific compounds described above in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Inducing Retraction of Subcutaneous Tissue

Another aspect of the invention provides a method for inducing retraction of subcutaneous tissue in a subject. The method comprises administering an effective amount of a fused heterotricyclic organic compound described herein, such as a compound of Formula I described above in Sub-Section A, to subcutaneous tissue of a subject to induce retraction of subcutaneous tissue. Formula I, as described above in Sub-Section A, is represented by:

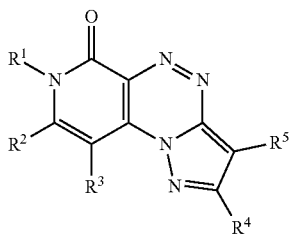

or a pharmaceutically acceptable salt thereof, wherein the variables are as defined above in Sub-Section A.

In certain embodiments, said administering comprises injecting said compound into subcutaneous tissue.

In certain embodiments, the subject is an adult human.

In certain embodiments, the compound is one of the generic or specific compounds described above in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Preventing Accumulation of Fat

Another aspect of the invention provides a method of preventing the accumulation of fat in a subject. The method comprises administering to a subject in need thereof an effective amount of a fused heterotricyclic organic compound described herein, such as a compound of Formula I described above in Sub-Section A, to prevent accumulation of fat in the subject. Formula I, as described above in Sub-Section A, is represented by:

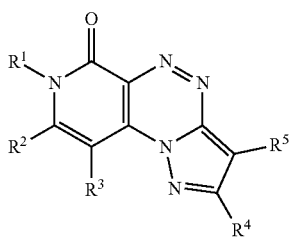

or a pharmaceutically acceptable salt thereof, wherein the variables are as defined above in Sub-Section A.

In certain embodiments, the fat is subcutaneous fat.

In certain embodiments, the accumulation of fat in a subject occurs in the subject's face, neck, chin, submental region, arm, thigh, knee, calf, buttocks, hips, or abdomen.

In certain embodiments, said administering comprises injecting said compound into tissue in the region in which accumulation of fat is to be prevented.

In certain embodiments, the subject is an adult human.

In certain embodiments, the compound is one of the generic or specific compounds described above in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Treating Medical Disorders

Another aspect of the invention provides a method of treating a disorder selected from the group consisting of an adipose tissue tumor, fat embolism, dyslipidemia, or fatty liver disease in a subject. The method comprises administering to a subject in need thereof a therapeutically effective amount of a fused heterotricyclic organic compound described herein, such as a compound of Formula I described above in Sub-Section A, to treat the disorder. Formula I, as described above in Sub-Section A, is represented by:

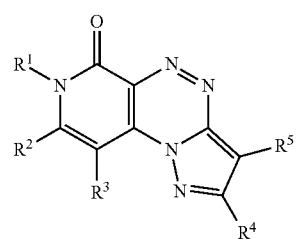

or a pharmaceutically acceptable salt thereof, wherein the variables are as defined above in Sub-Section A.

In certain embodiments, the disorder is an adipose tissue tumor (e.g., a lipoma). For example, in certain embodiments, the lipoma is an adenolipoma, angiolipoleiomyoma, angiolipoma, chondroid lipoma, corpus callosum lipoma, hibernoma, intradermal spindle cell lipoma, neural fibrolipoma, pleomorphic lipoma, spindle-cell lipoma, or a superficial subcutaneous lipoma.

In certain embodiments, the disorder is fat embolism. In certain other embodiments, the disorder is dyslipidemia. In certain other embodiments, the disorder is fatty liver disease. In certain embodiments, the disorder is fatty liver disease due to alcohol-induced liver cirrhosis.

In certain embodiments, the subject is an adult human.

In certain embodiments, the compound is one of the generic or specific compounds described above in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing the Amount of Fat or Cholesterol

Another aspect of the invention provides a method of reducing the amount of fat or cholesterol in a subject. The method comprises administering to a subject in need thereof an effective amount of a fused heterotricyclic organic compound described herein, such as a compound of Formula I described above in Sub-Section A, to reduce the amount of fat or cholesterol in the subject. Formula I, as described above in Sub-Section A, is represented by:

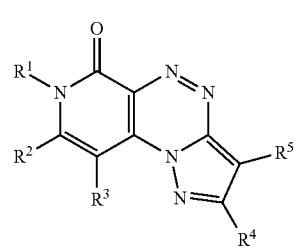

or a pharmaceutically acceptable salt thereof, wherein the variables are as defined above in Sub-Section A.

In certain embodiments, the method reduces the amount of fat in a subject.

In certain embodiments, the method improves regulation of energy balance in the subject, lipid homeostatis, insulin sensitivity, blood pressure homeostatis, or vascular health of the subject.

In certain embodiments, the method reduces the amount of cholesterol in a subject.

In certain embodiments, the subject suffers from a cardiovascular disease. For example, in certain embodiments, the cardiovascular disease is coronary artery disease or peripheral vascular disease.

In certain embodiments, the subject is an adult human.

In certain embodiments, the compound is one of the generic or specific compounds described above in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing the Amount of Mesenchymal Pre-adipocyte Stem Cell Precursors Another aspect of the invention provides a method of reducing the amount of mesenchymal pre-adipocyte stem cell precursors in a subject. The method comprises administering to a subject in need thereof an effective amount of a fused heterotricyclic organic compound described herein, such as a compound of Formula I described above in Sub-Section A, to reduce the amount of mesenchymal pre-adipocyte stem cell precursors in the subject. Formula I, as above in Sub-Section A, is represented by:

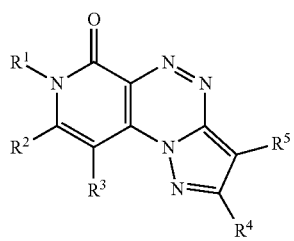

(I)

or a pharmaceutically acceptable salt thereof, wherein the variables are as defined in Section II.

In certain embodiments, the subject is an adult human.

In certain embodiments, the compound is one of the generic or specific compounds described above in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Inducing Death of Adipocyte Cells

Another aspect of the invention provides a method of inducing the death of an adipocyte cell. The method comprises exposing an adipocyte cell to an effective amount of a fused heterotricyclic organic compound described herein, such as a compound of Formula I described above in Sub-Section A, to induce death of the adipocyte cell. Formula I, as described above in Sub-Section A, is represented by:

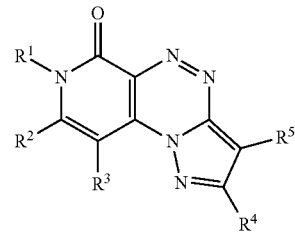

(I)

or a pharmaceutically acceptable salt thereof, wherein the variables are as defined in Sub-Section A.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing Skin Aging

Another aspect of the invention provides a method of reducing skin aging in a subject. The method comprises administering to a subject in need thereof an effective amount of a fused heterotricyclic organic compound described herein, such as a compound of Formula I described above in Sub-Section A, to reduce the effects of skin aging. Formula I, as described above in Sub-Section A, is represented by:

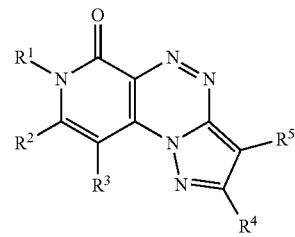

(I)

or a pharmaceutically acceptable salt thereof, wherein the variables are as defined in Sub-Section A.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

The description above describes multiple embodiments relating to various methods, such as methods of body contouring and/or reducing fat in a subject using certain fused heterotricyclic organic compounds. The patent application specifically contemplates all combinations of the embodiments. For example, the invention contemplates body contouring and/or reducing fat in a subject by administering a therapeutically effective amount of a compound of Formula I-A.

Combination Therapy

As indicated above, the invention embraces combination therapy, which includes the administration of a fused heterocyclic organic compound described herein (such as compound of Formula I or I-A described above in Sub-Section A) and a second agent as part of a specific treatment regimen intended to provide the beneficial effect from the co-action of these therapeutic agents. The beneficial effect of the combination may include pharmacokinetic or pharmacodynamic co-action resulting from the combination of therapeutic agents.

C. Pharmaceutical Compositions Containing Fused Heterotricyclic Organic Compounds The invention provides pharmaceutical compositions comprising a fused heterotricyclic organic compound described herein, such as a compound of Formula I or I-A described above in Sub-Section A, and a pharmaceutically acceptable carrier. In certain embodiments, the pharmaceutical compositions preferably comprise an effective amount of one or more of the fused heterotricyclic organic compounds described above (i.e., an amount effective to achieve one or more of the therapeutic applications described above in Sub-Section B), formulated together with one or more pharmaceutically acceptable carriers (additives) and/or diluents. As described in detail below in Section VI, pharmaceutical compositions of the present invention may be specially formulated for administration in solid or liquid form, including those adapted for the following: (1) parenteral administration by, for example, subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) oral administration, for example, drenches (aqueous or non-aqueous solutions or suspensions), tablets (e.g., those targeted for buccal, sublingual, and/or systemic absorption), boluses, powders, granules, pastes for application to the tongue; (4) intravaginally or intrarectally, for example, as a pessary, cream or foam; (5) sublingually; (6) occularly; (7) transdermally; or (8) nasally.

D. Medical Kits Containing Fused Heterotricyclic Organic Compounds

Another aspect of the invention provides a kit for body contouring and/or reducing the amount of fat in a subject. The kit comprises: i) instructions for body contouring and/or reducing the amount of fat in a subject (for example, modifying the contour of a subject's externally exposed body part containing fat; reducing the amount of subcutaneous fat in a subject; inducing retraction of dermal tissue or subcutaneous tissue in a subject; preventing the accumulation of fat in a subject; treating a disorder selected from the group consisting of an adipose tissue tumor (e.g., a lipoma), fat embolism, dyslipidemia, or fatty liver disease in a subject; reducing the amount of fat or cholesterol in a subject; and reducing the amount of mesenchymal pre-adipocyte stem cell precursors in a subject); and ii) a fused heterotricyclic organic compound described herein, such as a compound of Formula I described above in Sub-Section A. The kit may comprise one or more unit dosage forms containing an amount of a fused heterotricyclic organic compound described herein, such as a compound of Formula I described above in Sub-Section A, that is effective for body contouring and/or reduction of fat in a subject.

III. Dipyrido-Pyrimidinone Organic Compounds & Their Use

Certain aspects of the invention provide dipyrido-pyrimidinone organic compounds, pharmaceutical compositions containing such compounds, medical kits, and therapeutic applications using such compounds. These compounds, pharmaceutical compositions, medical kits, and therapeutic applications are described in more detail in the sections below.

A. Dipyrido-pyrimidinone Organic Compounds

One aspect of the invention provides dipyrido-pyrimidinone organic compounds. The dipyrido-pyrimidinone compounds are contemplated to be useful in the methods, compositions, and kits described herein. In certain embodiments, the dipyrido-pyrimidinone organic compound is a compound embraced by Formula I:

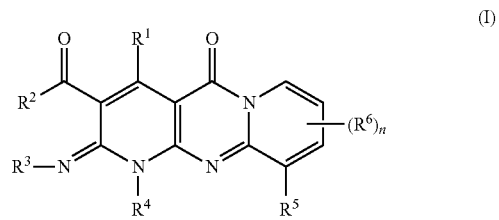

or a pharmaceutically acceptable salt thereof, wherein:

$R^1$ and $R^6$ each represent independently for each occurrence hydrogen, halogen, —($C_1$-$C_6$)alkyl, or —($C_3$-$C_6$)cycloalkyl;

$R^2$ is —$N(R^7)R^8$, —$OR^7$, —($C_1$-$C_6$)alkyl, or —($C_3$-$C_6$)cycloalkyl;

$R^3$ is hydrogen, —($C_1$-$C_6$)alkyl, or —($C_3$-$C_6$)cycloalkyl;

$R^4$ is aralkyl or heteroaralkyl, each of which is optionally substituted with 1, 2, or 3 substituents independently selected from the group consisting of halogen, —($C_1$-$C_6$)alkyl, —($C_3$-$C_6$)cycloalkyl, hydroxyl, —($C_1$-$C_6$)alkoxy, —$N(R^7)R^8$, —$C(O)N(R^7)R^8$, and —$N(R^7)C(O)R^8$;

$R^5$ is hydrogen, —($C_1$-$C_6$)alkyl, —($C_3$-$C_6$)cycloalkyl, —$CO_2R^7$, —$C(O)N(R^7)R^8$, or —$N(R^7)C(O)R^8$;

$R^7$ and $R^8$ each represent independently for each occurrence hydrogen, —($C_1$-$C_6$)alkyl, or —($C_3$-$C_6$)cycloalkyl; or when $R^7$ and $R^8$ are attached to the same nitrogen atom, then $R^7$ and $R^8$ may be taken together with the nitrogen atom to which they are attached to form a 3-7 membered heterocycle; and n is 1, 2, or 3.

In certain embodiments, $R^1$ and $R^6$ are hydrogen.

In certain embodiments, $R^2$ is —$N(R^7)R^8$ or —$OR^7$. In certain other embodiments, $R^2$ is —$N(R^7)R^8$. In certain other embodiments, $R^2$ is —$NH_2$.

In certain embodiments, $R^3$ is hydrogen.

In certain embodiments, $R^4$ is aralkyl or heteroaralkyl, each of which is optionally substituted with 1, 2, or 3 substituents independently selected from the group consisting of chloro, fluoro —($C_1$-$C_6$)alkyl, cyclopropyl, hydroxyl, and —($C_1$-$C_6$)alkoxy. In certain other embodiments, $R^4$ is aralkyl or heteroaralkyl, each of which is optionally substituted with methyl or methoxy. In certain other embodiments, $R^4$ is benzyl optionally substituted with methyl or methoxy. In certain other embodiments, $R^4$ is benzyl. In certain other embodiments, $R^4$ is —($C_1$-$C_3$)alkylene-pyridinyl optionally substituted with methyl. In certain other embodiments, $R^4$ is —$CH_2$-pyridinyl.

In certain embodiments, $R^5$ is hydrogen or —($C_1$-$C_6$)alkyl. In certain other embodiments, $R^5$ is hydrogen, methyl, or ethyl.

The description above describes multiple embodiments relating to compounds of Formula I. The patent application specifically contemplates all combinations of the embodiments.

In certain embodiments, the compound is a compound of Formula I-A:

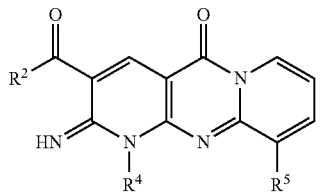

(I-A)

or a pharmaceutically acceptable salt thereof, wherein:

$R^2$ is —N($R^7$)$R^8$;

$R^4$ is aralkyl or heteroaralkyl, each of which is optionally substituted with 1, 2, or 3 substituents independently selected from the group consisting of halogen, —(C$_1$-C$_6$)alkyl, —(C$_3$-C$_5$)cycloalkyl, hydroxyl, —(C$_1$-C$_6$)alkoxy, and —N($R^7$)$R^8$;

$R^5$ is hydrogen, —(C$_1$-C$_6$)alkyl, or —(C$_3$-C$_6$)cycloalkyl;

$R^7$ and $R^8$ each represent independently hydrogen, —(C$_1$-C$_6$)alkyl, or —(C$_3$-C$_6$)cycloalkyl; or when $R^7$ and $R^8$ are attached to the same nitrogen atom, then $R^7$ and $R^8$ may be taken together with the nitrogen atom to which they are attached to form a 3-7 membered heterocycle.

In certain embodiments, $R^2$ is —NH$_2$.

In certain embodiments, $R^4$ is aralkyl or heteroaralkyl, each of which is optionally substituted with 1, 2, or 3 substituents independently selected from the group consisting of chloro, fluoro —(C$_1$-C$_6$)alkyl, cyclopropyl, hydroxyl, and —(C$_1$-C$_6$)alkoxy. In certain other embodiments, $R^4$ is aralkyl or heteroaralkyl, each of which is optionally substituted with methyl or methoxy. In certain other embodiments, $R^4$ is benzyl optionally substituted with methyl or methoxy. In certain other embodiments, $R^4$ is benzyl. In certain other embodiments, $R^4$ is —(C$_1$-C$_3$)alkylene-pyridinyl optionally substituted with methyl. In certain other embodiments, $R^4$ is —CH$_2$-pyridinyl.

In certain embodiments, $R^5$ is hydrogen. In certain other embodiments, $R^5$ is —(C$_1$-C$_6$)alkyl. In certain other embodiments, $R^5$ is methyl or ethyl.

The description above describes multiple embodiments relating to compounds of Formula I-A. The patent application specifically contemplates all combinations of the embodiments.

In certain embodiments, the compound is one of the following or a pharmaceutically acceptable salt thereof:

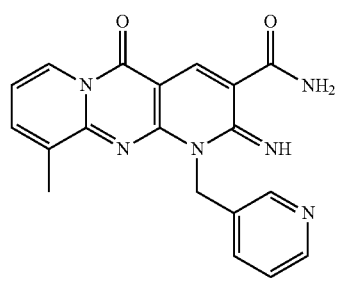

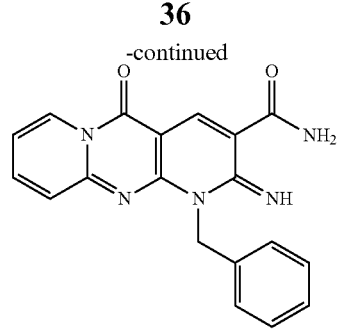

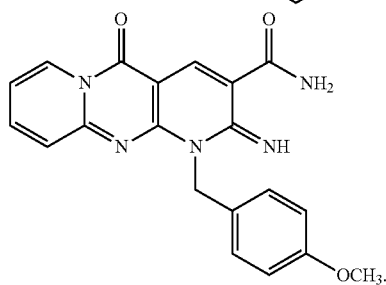

In certain other embodiments, the compound is one of the compounds listed in Table 2 below or a pharmaceutically acceptable salt thereof.

TABLE 2

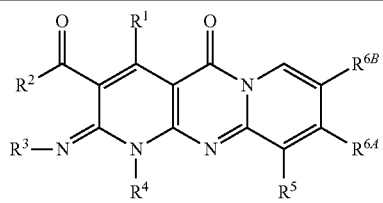

| Compound No. | $R^1$ | $R^2$ | $R^3$ | $R^4$ | $R^5$ |
|---|---|---|---|---|---|
| I-1 | H | NH$_2$ | H | benzyl | H |
| I-2 | H | NH$_2$ | H | para-methoxybenzyl | H |
| I-3 | H | NH$_2$ | H | ortho-methoxybenzyl | H |
| I-4 | H | NH$_2$ | H | meta-methoxybenzyl | H |
| I-5 | H | NH$_2$ | H | para-methylbenzyl | H |
| I-6 | H | NH$_2$ | H | ortho-methylbenzyl | H |
| I-7 | H | NH$_2$ | H | para-chlorobenzyl | H |
| I-8 | H | NH$_2$ | H | ortho-chlorobenzyl | H |
| I-9 | H | NH$_2$ | H | 3,5-difluorobenzyl | H |
| I-10 | H | NH$_2$ | H | para-cyclopropylbenzyl | H |
| I-11 | H | NH$_2$ | H | para-hydroxybenzyl | H |
| I-12 | H | NH$_2$ | H | 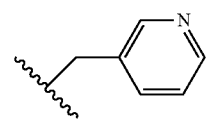 | H |
| I-13 | H | NH$_2$ | H | 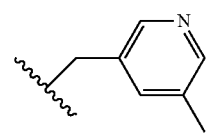 | H |
| I-14 | H | NH$_2$ | H | 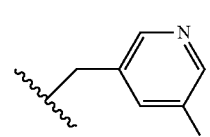 | H |

TABLE 2-continued

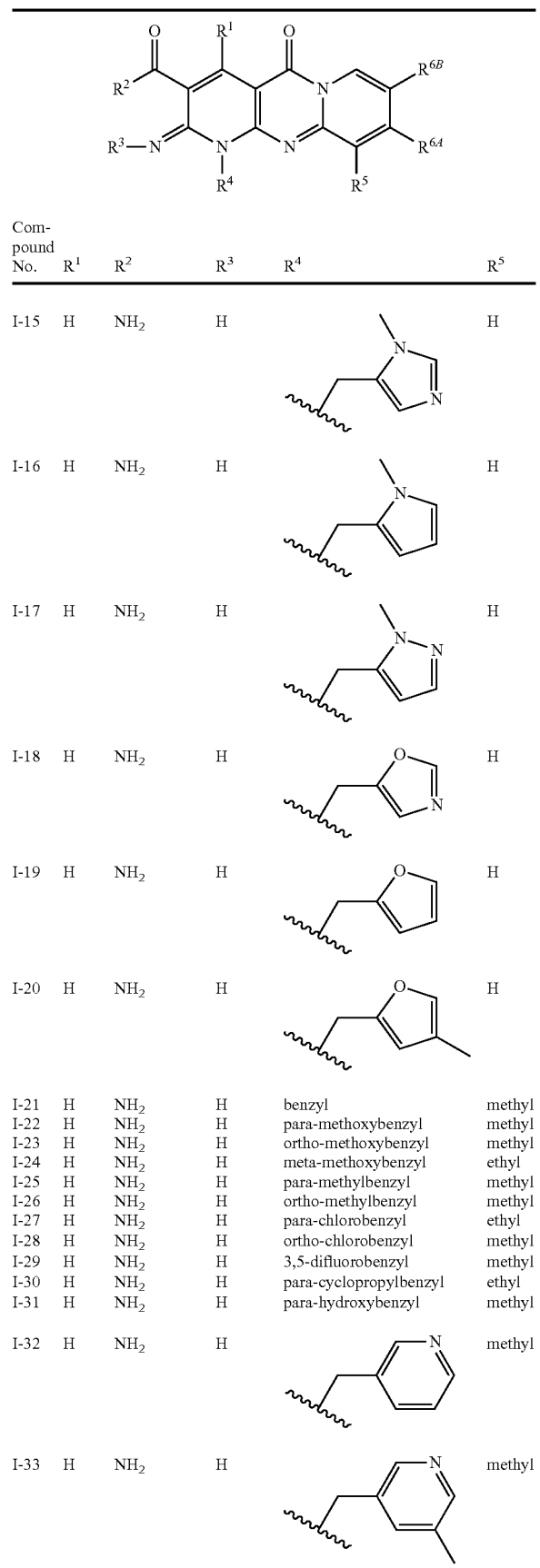
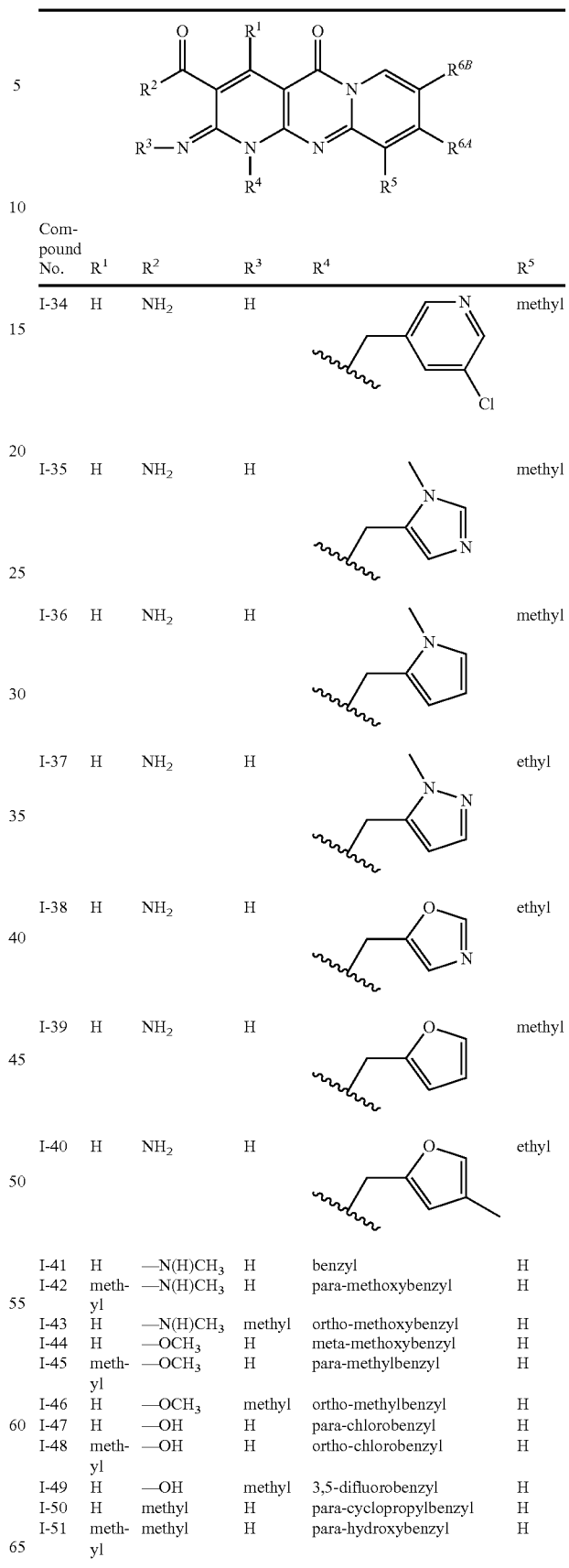

| Compound No. | R¹ | R² | R³ | R⁴ | R⁵ |
|---|---|---|---|---|---|
| I-15 | H | NH₂ | H | (1-methylimidazol-5-yl)methyl | H |
| I-16 | H | NH₂ | H | (1-methylpyrrol-2-yl)methyl | H |
| I-17 | H | NH₂ | H | (1-methylpyrazol-5-yl)methyl | H |
| I-18 | H | NH₂ | H | (oxazol-5-yl)methyl | H |
| I-19 | H | NH₂ | H | (furan-2-yl)methyl | H |
| I-20 | H | NH₂ | H | (4-methylfuran-2-yl)methyl | H |
| I-21 | H | NH₂ | H | benzyl | methyl |
| I-22 | H | NH₂ | H | para-methoxybenzyl | methyl |
| I-23 | H | NH₂ | H | ortho-methoxybenzyl | methyl |
| I-24 | H | NH₂ | H | meta-methoxybenzyl | ethyl |
| I-25 | H | NH₂ | H | para-methylbenzyl | methyl |
| I-26 | H | NH₂ | H | ortho-methylbenzyl | methyl |
| I-27 | H | NH₂ | H | para-chlorobenzyl | ethyl |
| I-28 | H | NH₂ | H | ortho-chlorobenzyl | methyl |
| I-29 | H | NH₂ | H | 3,5-difluorobenzyl | methyl |
| I-30 | H | NH₂ | H | para-cyclopropylbenzyl | ethyl |
| I-31 | H | NH₂ | H | para-hydroxybenzyl | methyl |
| I-32 | H | NH₂ | H | (pyridin-3-yl)methyl | methyl |
| I-33 | H | NH₂ | H | (5-methylpyridin-3-yl)methyl | methyl |
| I-34 | H | NH₂ | H | (5-chloropyridin-3-yl)methyl | methyl |
| I-35 | H | NH₂ | H | (1-methylimidazol-5-yl)methyl | methyl |
| I-36 | H | NH₂ | H | (1-methylpyrrol-2-yl)methyl | methyl |
| I-37 | H | NH₂ | H | (1-methylpyrazol-5-yl)methyl | ethyl |
| I-38 | H | NH₂ | H | (oxazol-5-yl)methyl | ethyl |
| I-39 | H | NH₂ | H | (furan-2-yl)methyl | methyl |
| I-40 | H | NH₂ | H | (4-methylfuran-2-yl)methyl | ethyl |
| I-41 | H | —N(H)CH₃ | H | benzyl | H |
| I-42 | methyl | —N(H)CH₃ | H | para-methoxybenzyl | H |
| I-43 | H | —N(H)CH₃ | methyl | ortho-methoxybenzyl | H |
| I-44 | H | —OCH₃ | H | meta-methoxybenzyl | H |
| I-45 | methyl | —OCH₃ | H | para-methylbenzyl | H |
| I-46 | H | —OCH₃ | methyl | ortho-methylbenzyl | H |
| I-47 | H | —OH | H | para-chlorobenzyl | H |
| I-48 | methyl | —OH | H | ortho-chlorobenzyl | H |
| I-49 | H | —OH | methyl | 3,5-difluorobenzyl | H |
| I-50 | H | methyl | H | para-cyclopropylbenzyl | H |
| I-51 | methyl | methyl | H | para-hydroxybenzyl | H |

TABLE 2-continued

| Compound No. | R¹ | R² | R³ | R⁴ | (group) | R⁵ |
|---|---|---|---|---|---|---|
| I-52 | H | —N(H)CH₃ | H | | pyridin-3-ylmethyl | H |
| I-53 | H | —N(H)CH₃ | H | | (4-methylpyridin-3-yl)methyl | H |
| I-54 | H | —N(H)CH₃ | methyl | | (5-chloropyridin-3-yl)methyl | H |
| I-55 | H | —OCH₃ | H | | (1-methylimidazol-5-yl)methyl | H |
| I-56 | H | —OCH₃ | H | | (1-methylpyrrol-2-yl)methyl | H |
| I-57 | H | —OCH₃ | methyl | | (1-methylimidazol-5-yl)methyl | H |
| I-58 | H | —OH | H | | oxazol-5-ylmethyl | H |
| I-59 | H | —OH | H | | furan-2-ylmethyl | H |
| I-60 | H | —OH | methyl | | (4-methylfuran-2-yl)methyl | H |

Methods for preparing compounds described herein are illustrated in the following synthetic schemes. These schemes are given for the purpose of illustrating the invention, and should not be regarded in any manner as limiting the scope or the spirit of the invention. Starting materials shown in the schemes can be obtained from commercial sources or can be prepared based on procedures described in the literature.

The synthetic route illustrated in Scheme III-1 depicts exemplary procedures for preparing monoalkyl amides, dialkyl amides, and alkylimine compounds starting from amide A, which is commercially available at least when group A is phenyl, pyridinyl, and p-methoxylphenyl. In the first step, amide A is reacted with a protecting group (Pg-X) that reacts with the imine functional group to provide protected imine B. Exemplary reaction procedures include reacting amide A with

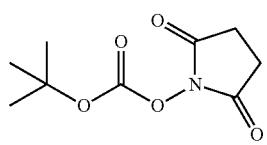

in the presence of a mild base, such as pyridine, to provide protected imine B. Reaction of protected imine B with one molar equivalent of methyl iodide the presence of a mild base, such as pyridine, provides monoalkyl amide C. The protecting group (Pg) in monoalkyl amide C can be removed, such by treatment with TMSI when the protecting group is —CO₂-tert-butyl, to provide monoalkyl amide product E. Alternatively, monoalkyl amide C can be reacted with a second molar equivalent of methyl iodide in the presence of a mild base, such as pyridine, to provide dialkyl amide D. The protecting group (Pg) in dialkyl amide D can be removed, such by treatment with TMSI when the protecting group is —CO₂-tert-butyl, to provide dialkyl amide product F. If desired, alkylimine G can be prepared by reacting dialkyl amide product F with one molar equivalent of methyl iodide in the presence of a mild base, such as pyridine. If further functional group manipulations are desired, such chemical transformations can be performed using procedures described in the literature, such as in, for example, "Comprehensive Organic Synthesis" (B. M. Trost & I. Fleming, eds., 1991-1992); Carey, F. A. and Sundberg, R. J. Advanced Organic Chemistry Part B: Reactions and Synthesis, 3$^{rd}$ Ed.; Plenum Press: New York, 1990; and J. March, Advanced Organic Chemistry, McGraw Hill Book Company, New York, (1992, 4$^{th}$ edition). For example, amides (such as the exocyclic primary amide in Compound A) can be converted to a —CO₂H group by treatment with acid and water, and such a carboxylic acid can be converted to an alkyl ester, such as a —CO₂CH₃ group upon reaction of the —CO₂H group with methanol in the presence of acid.

SCHEME III-1.

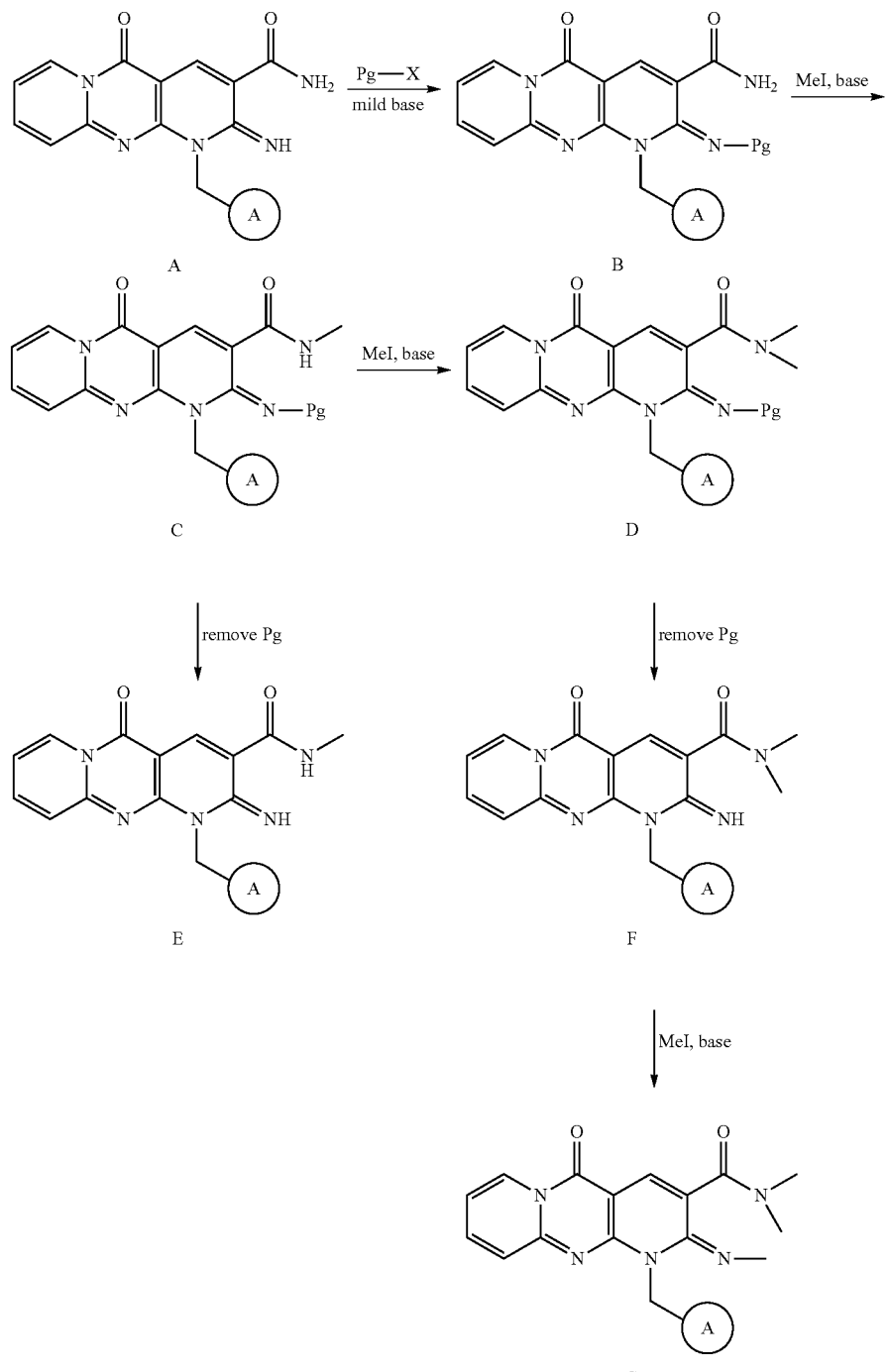

A is aryl or heteroaryl
Pg is protecting group
X is a leaving group

The synthetic route illustrated in Scheme III-2 depicts exemplary procedures for preparing compounds having various aralkyl or heteroaralkyl groups attached to the tricyclic core starting from amine A1. The procedure involves reacting amine A1 with an aralkyl halide or a heteroaralkyl halide B1 in the presence of a mild base to form synthetic intermediate C1. Protecting groups are removed from compound C1 to provide final product D1. Exemplary protecting groups useful in such transformations are described in, for example, Greene, T. W.; Wuts, P. G. M. *Protective Groups in Organic Synthesis*, 2$_{nd}$ ed.; Wiley, New York, 1991. There are many aralkyl halides and heteroaralkyl halides B1 available from commercial sources or that can be prepared according to procedures described in the literature. In certain embodiments, compound B1 is one of the following: para-cyclopropylbenzyl bromide, 3,5-difluorobenzyl bromide,

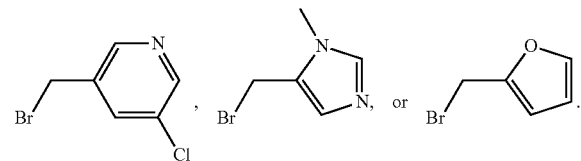

SCHEME III-2.

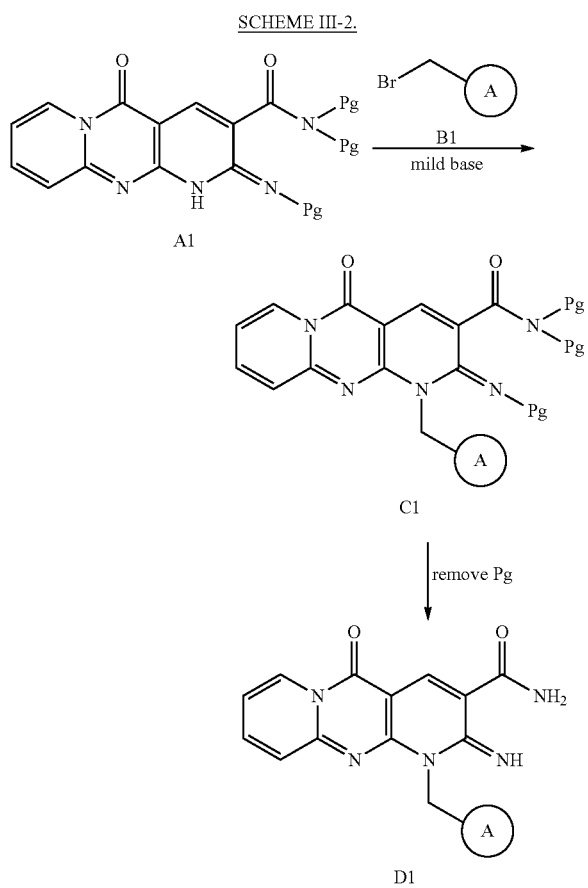

A is aryl or heteroaryl
Pg is protecting group

B. Therapeutic Applications of Dipyrido-pyrimidinone Organic Compounds

The invention provides methods for body contouring and/or reduction of fat in a subject using the dipyrido-pyrimidinone organic compounds and pharmaceutical compositions described herein. Methods include the use of dipyrido-pyrimidinone organic compounds described herein as stand-alone therapeutic agents and/or as part of a combination therapy with another medicinal agent.

Cosmetic Methods of Modifying the Contour of a Subject's Externally Exposed Body Part One aspect of the invention provides a method of modifying the contour of a subject's externally exposed body part containing fat. The method comprises administering to said body part an amount of a dipyrido-pyrimidinone organic compound described herein, such as a compound of Formula I described above in Sub-Section A, effective to modify the contour of said body part. Formula I, as described above in Sub-Section A, is represented by:

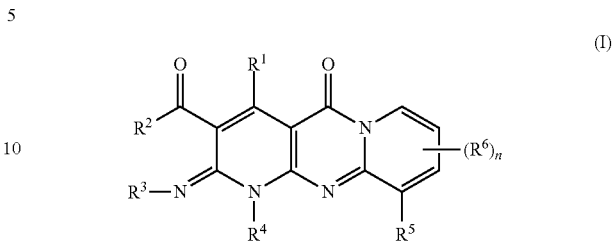

or a pharmaceutically acceptable salt thereof, wherein the variables are as defined in Sub-Section A.

In certain embodiments, the externally exposed body part containing fat is the subject's face, neck, chin, submental region, arm, thigh, knee, calf, buttocks, hips, or abdomen. In certain other embodiments, the externally exposed body part containing fat is the subject's face. In certain other embodiments, the externally exposed body part containing fat is the subject's chin or cheek. In certain embodiments, the externally exposed body part is the subject's neck.

In certain embodiments, the subject experiences at least a 5% by weight reduction in the amount of fat in the subject's body part exposed to said compound. In certain other embodiments, the subject experiences at least a 10% by weight reduction in the amount of fat in the subject's body part exposed to said compound. In certain embodiments, the subject experiences at least a 15% by weight reduction in the amount of fat in the subject's body part exposed to said compound. In certain other embodiments, the subject experiences at least a 25% by weight reduction in the amount of fat in the subject's body part exposed to said compound. In certain other embodiments, the subject experiences from about 1% to about 10%, about 10% to about 20%, about 20% to about 40%, about 40% to about 60%, about 60% to about 80%, about 1% to about 30%, or about 1% to about 50% by weight reduction in the amount of fat in the subject's body part exposed to said compound.

In certain embodiments, the administering comprises injecting said compound into said body part.

In certain embodiments, the subject is an adult human. In certain embodiments, the subject is an animal, such as dog or cat.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing the Amount of Subcutaneous Fat

Another aspect of the invention provides a method of reducing the amount of subcutaneous fat in a subject. The method comprises exposing subcutaneous fat in a subject to an effective amount of a dipyrido-pyrimidinone organic compound described herein, such as a compound of Formula I described above in Sub-Section A, to reduce the amount of subcutaneous fat in said subject. Formula I, as described above in Sub-Section A, is represented by:

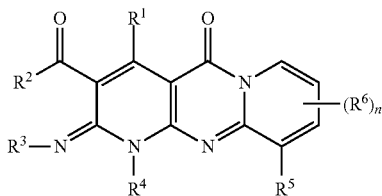

or a pharmaceutically acceptable salt thereof, wherein the variables are as defined in Sub-Section A.

In certain embodiments, the subcutaneous fat is located in the subject's face, neck, chin, submental region, arm, thigh, knee, calf, buttocks, hips, or abdomen. In certain other embodiments, the subcutaneous fat is located in subject's face. In certain other embodiments, the subcutaneous fat is located in subject's neck.

In certain embodiments, the subject experiences at least a 5% by weight reduction in the amount of subcutaneous fat in the subject's body part exposed to said compound. In certain other embodiments, the subject experiences at least a 10% by weight reduction in the amount of subcutaneous fat in the subject's body part exposed to said compound. In certain embodiments, the subject experiences at least a 15% by weight reduction in the amount of subcutaneous fat in the subject's body part exposed to said compound. In certain other embodiments, the subject experiences at least a 25% by weight reduction in the amount of subcutaneous fat in the subject's body part exposed to said compound. In certain other embodiments, the subject experiences 1% to about 10%, about 10% to about 20%, about 20% to about 40%, about 40% to about 60%, about 60% to about 80%, about 1% to about 30%, or about 1% to about 50% by weight reduction in the amount of subcutaneous fat in the subject's body part exposed to said compound.

In certain embodiments, said exposing comprises injecting said compound of Formula I into a region of subcutaneous fat.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Inducing Retraction of Dermal Tissue

Another aspect of the invention provides a method for inducing retraction of dermal tissue in a subject. The method comprises administering an effective amount of a dipyrido-pyrimidinone organic compound described herein, such as a compound of Formula I described above in Sub-Section A, to dermal tissue of a subject to induce retraction of dermal tissue. Formula I, as described above in Sub-Section A, is represented by:

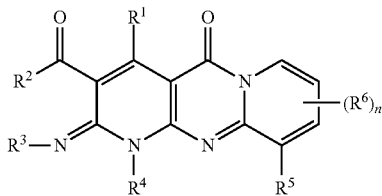

or a pharmaceutically acceptable salt thereof, wherein the variables are as defined in Sub-Section A.

In certain embodiments, said administering comprises injecting said compound into dermal tissue.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Inducing Retraction of Subcutaneous Tissue

Another aspect of the invention provides a method for inducing retraction of subcutaneous tissue in a subject. The method comprises administering an effective amount of a dipyrido-pyrimidinone organic compound described herein, such as a compound of Formula I described above in Sub-Section A, to subcutaneous tissue of a subject to induce retraction of subcutaneous tissue. Formula I, as described above in Sub-Section A, is represented by:

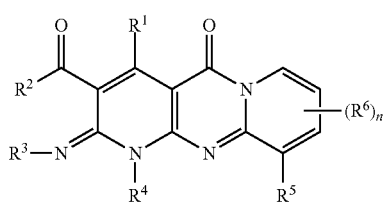

or a pharmaceutically acceptable salt thereof, wherein the variables are as defined in Sub-Section A.

In certain embodiments, said administering comprises injecting said compound into subcutaneous tissue.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Preventing Accumulation of Fat

Another aspect of the invention provides a method of preventing the accumulation of fat in a subject. The method comprises administering to a subject in need thereof an effective amount of a dipyrido-pyrimidinone organic compound described herein, such as a compound of Formula I described above in Sub-Section A, to prevent accumulation of fat in the subject. Formula I, as described above in Sub-Section A, is represented by:

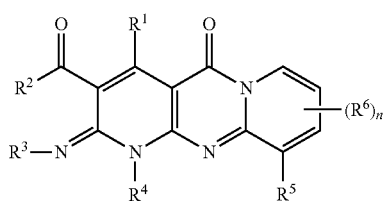

or a pharmaceutically acceptable salt thereof, wherein the variables are as defined in Sub-Section A.

In certain embodiments, the fat is subcutaneous fat.

In certain embodiments, the accumulation of fat in a subject occurs in the subject's face, neck, chin, submental region, arm, thigh, knee, calf, buttocks, hips, or abdomen.

In certain embodiments, said administering comprises injecting said compound into tissue in the region in which accumulation of fat is to be prevented.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Treating Medical Disorders

Another aspect of the invention provides a method of treating a disorder selected from the group consisting of an adipose tissue tumor, fat embolism, dyslipidemia, or fatty liver disease in a subject. The method comprises administering to a subject in need thereof a therapeutically effective amount of a dipyrido-pyrimidinone organic compound described herein, such as a compound of Formula I described above in Sub-Section A, to treat the disorder. Formula I, as described above in Sub-Section A, is represented by:

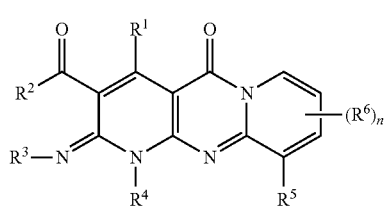

or a pharmaceutically acceptable salt thereof, wherein the variables are as defined in Sub-Section A.

In certain embodiments, the disorder is an adipose tissue tumor (e.g., a lipoma). For example, in certain embodiments, the lipoma is an adenolipoma, angiolipoleiomyoma, angiolipoma, chondroid lipoma, corpus callosum lipoma, hibernoma, intradermal spindle cell lipoma, neural fibrolipoma, pleomorphic lipoma, spindle-cell lipoma, or a superficial subcutaneous lipoma.

In certain embodiments, the disorder is fat embolism. In certain other embodiments, the disorder is dyslipidemia. In certain other embodiments, the disorder is fatty liver disease. In certain embodiments, the disorder is fatty liver disease due to alcohol-induced liver cirrhosis.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing the Amount of Fat or Cholesterol

Another aspect of the invention provides a method of reducing the amount of fat or cholesterol in a subject. The method comprises administering to a subject in need thereof an effective amount of a dipyrido-pyrimidinone organic compound described herein, such as a compound of Formula I described above in Sub-Section A, to reduce the amount of fat or cholesterol in the subject. Formula I, as described above in Sub-Section A, is represented by:

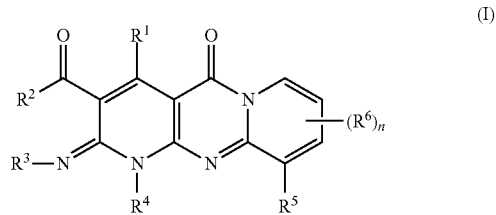

or a pharmaceutically acceptable salt thereof, wherein the variables are as defined in Sub-Section A.

In certain embodiments, the method reduces the amount of fat in a subject.

In certain embodiments, the method improves regulation of energy balance in the subject, lipid homeostatis, insulin sensitivity, blood pressure homeostatis, or vascular health of the subject.

In certain embodiments, the method reduces the amount of cholesterol in a subject.

In certain embodiments, the subject suffers from a cardiovascular disease. For example, in certain embodiments, the cardiovascular disease is coronary artery disease or peripheral vascular disease.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing the Amount of Mesenchymal Pre-adipocyte Stem Cell Precursors Another aspect of the invention provides a method of reducing the amount of mesenchymal pre-adipocyte stem cell precursors in a subject. The method comprises administering to a subject in need thereof an effective amount of a dipyrido-pyrimidinone organic compound described herein, such as a compound of Formula I described above in Sub-Section A, to reduce the amount of mesenchymal pre-adipocyte stem cell precursors in the subject. Formula I, as described above in Sub-Section A, is represented by:

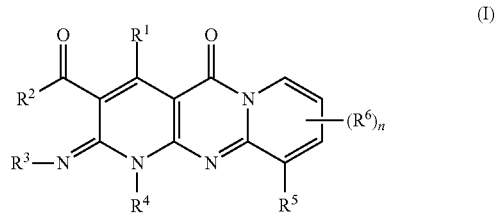

or a pharmaceutically acceptable salt thereof, wherein the variables are as defined in Sub-Section A.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Inducing Death of Adipocyte Cells

Another aspect of the invention provides a method of inducing the death of an adipocyte cell. The method comprises exposing an adipocyte cell to an effective amount of a dipyrido-pyrimidinone organic compound described herein, such as a compound of Formula I, to induce death of the adipocyte cell. Formula I, as described above in Sub-Section A, is represented by:

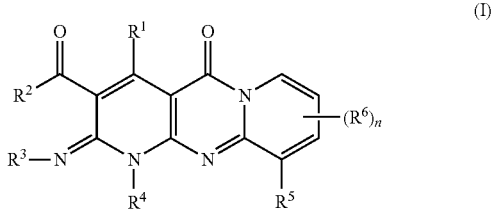

(I)

or a pharmaceutically acceptable salt thereof, wherein the variables are as defined in Sub-Section A.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing Skin Aging

Another aspect of the invention provides a method of reducing skin aging in a subject. The method comprises administering to a subject in need thereof an effective amount of a dipyrido-pyrimidinone organic compound described herein, such as a compound of Formula I described above in Sub-Section A, to reduce the effects of skin aging. Formula I, as described above in Sub-Section A, is represented by:

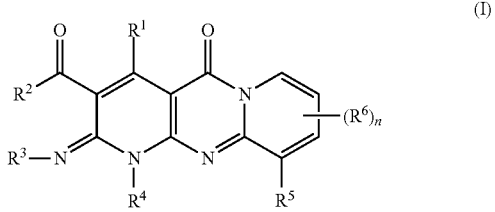

(I)

or a pharmaceutically acceptable salt thereof, wherein the variables are as defined in Sub-Section A.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

The description above describes multiple embodiments relating to various methods, such as methods of body contouring and/or reducing fat in a subject using certain dipyrido-pyrimidinone organic compounds. The patent application specifically contemplates all combinations of the embodiments. For example, the invention contemplates body contouring and/or reducing fat in a subject by administering a therapeutically effective amount of a compound of Formula I-A.

Combination Therapy

As indicated above, the invention embraces combination therapy, which includes the administration of a dipyrido-pyrimidinone organic compound described herein (such as compound of Formula I or I-A described above in Sub-Section A) and a second agent as part of a specific treatment regimen intended to provide the beneficial effect from the co-action of these therapeutic agents. The beneficial effect of the combination may include pharmacokinetic or pharmacodynamic co-action resulting from the combination of therapeutic agents.

C. Pharmaceutical Compositions Containing Dipyrido-pyrimidinone Organic Compounds The invention provides pharmaceutical compositions comprising a dipyrido-pyrimidinone organic compound described herein, such as a compound of Formula I or I-A described above in Sub-Section A, and a pharmaceutically acceptable carrier. In certain embodiments, the pharmaceutical compositions preferably comprise an effective amount of one or more of the dipyrido-pyrimidinone organic compounds described above (i.e., an amount effective to achieve one or more of the therapeutic applications described in Sub-Section B herein), formulated together with one or more pharmaceutically acceptable carriers (additives) and/or diluents. As described in detail below in Section VI, pharmaceutical compositions of the present invention may be specially formulated for administration in solid or liquid form, including those adapted for the following: (1) parenteral administration by, for example, subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) oral administration, for example, drenches (aqueous or non-aqueous solutions or suspensions), tablets (e.g., those targeted for buccal, sublingual, and/or systemic absorption), boluses, powders, granules, pastes for application to the tongue; (4) intravaginally or intrarectally, for example, as a pessary, cream or foam; (5) sublingually; (6) occularly; (7) transdermally; or (8) nasally.

D. Medical Kits Containing Dipyrido-pyrimidinone Organic Compounds

Another aspect of the invention provides a kit for body contouring and/or reducing the amount of fat in a subject. The kit comprises: i) instructions for body contouring and/or reducing the amount of fat in a subject (for example, modifying the contour of a subject's externally exposed body part containing fat; reducing the amount of subcutaneous fat in a subject; inducing retraction of dermal tissue or subcutaneous tissue in a subject; preventing the accumulation of fat in a subject; treating a disorder selected from the group consisting of an adipose tissue tumor (e.g., a lipoma), fat embolism, dyslipidemia, or fatty liver disease in a subject; reducing the amount of fat or cholesterol in a subject; and reducing the amount of mesenchymal pre-adipocyte stem cell precursors in a subject); and ii) a dipyrido-pyrimidinone organic compound described herein, such as a compound of Formula I described above in Sub-Section A. The kit may comprise one or more unit dosage forms containing an amount of a dipyrido-pyrimidinone organic compound described herein, such as a compound of Formula described above in Sub-Section A, that is effective for body contouring and/or reduction of fat in a subject.

The description above describes multiple aspects and embodiments of the invention, including dipyrido-pyrimidinone organic compounds, compositions comprising dipyrido-pyrimidinone organic compounds, methods of using the dipyrido-pyrimidinone organic compounds, and kits. The patent application specifically contemplates all combinations and permutations of the aspects and embodiments. For example, the invention contemplates body contouring and/or reducing fat in a human patient by administering a therapeutically effective amount of a compound of Formula I-A described above in Sub-Section A. Further, for example, the invention contemplates a kit for body contouring and/or reduction of fat in a subject, the kit comprising instructions for body contouring and/or reducing fat in a subject and ii) a dipyrido-pyrimidinone organic compound described herein, such as a compound of Formula I-A described above in Sub-Section A.

IV. Tetrahydropyrimido-Furo-Isoquinolinone Organic Compounds & Their Use

Certain aspects of the invention provide tetrahydropyrimido-furo-isoquinolinone organic compounds, pharmaceutical compositions containing such compounds, medical kits, and therapeutic applications using such compounds. These compounds, pharmaceutical compositions, medical kits, and therapeutic applications are described in more detail in the sections below.

A. Tetrahydropyrimido-furo-isoquinolinone Organic Compounds

One aspect of the invention provides tetrahydropyrimido-furo-isoquinolinone organic compounds. The tetrahydropyrimido-furo-isoquinolinone organic compounds are contemplated to be useful in the methods, compositions, and kits described herein. In certain embodiments, the tetrahydropyrimido-furo-isoquinolinone organic compound is a compound embraced by Formula I:

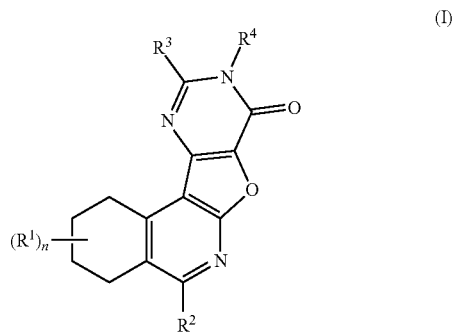

(I)

or a pharmaceutically acceptable salt thereof, wherein:

$R^1$ and $R^3$ each represent independently for each occurrence hydrogen, halogen, —($C_1$-$C_6$)alkyl, or —($C_3$-$C_6$)cycloalkyl;

$R^2$ is —($C_1$-$C_6$)alkyl, —($C_3$-$C_6$)cycloalkyl, phenyl, 5-6 membered heteroaryl, aralkyl, or —($C_1$-$C_6$)alkoxy, wherein said cycloalkyl, phenyl, 5-6 membered heteroaryl, and aralkyl are optionally substituted with 1, 2, or 3 substituents independently selected from the group consisting of halogen, —($C_1$-$C_6$)alkyl, —($C_3$-$C_6$)cycloalkyl, hydroxyl, and —($C_1$-$C_6$)alkoxy;

$R^4$ is —($C_1$-$C_6$)alkylene-$X^1$ or —($C_3$-$C_6$)cycloalkyl-$X^1$;

$X^1$ is —C(O)N($R^5$)$R^6$, —N($R^5$)C(O)$R^6$, —$CO_2R^6$, —C(O)$R^6$, —O$R^6$, or —N($R^5$)$R^6$;

$R^5$ and $R^6$ each represent independently hydrogen, —($C_1$-$C_6$)alkyl, or —($C_3$-$C_6$)cycloalkyl; or when $R^5$ and $R^6$ are attached to the same nitrogen atom, then $R^5$ and $R^6$ may be taken together with the nitrogen atom to which they are attached to form a 3-7 membered heterocycle; and n is 1, 2, or 3.

In certain embodiments, $R^1$ is hydrogen.

In certain embodiments, $R^2$ is —($C_1$-$C_6$)alkyl. In certain other embodiments, $R^2$ is methyl, ethyl, n-propyl, or isopropyl. In certain other embodiments, $R^2$ is phenyl. In certain other embodiments, $R^2$ is phenyl substituted with 1, 2, or 3 substituents independently selected from the group consisting of halogen, —($C_1$-$C_6$)alkyl, hydroxyl, and —($C_1$-$C_6$)alkoxy.

In certain embodiments, $R^3$ is hydrogen.

In certain embodiments, $R^4$ is —($C_1$-$C_6$)alkylene-$X^1$. In certain other embodiments, $R^4$ is —($C_1$-$C_6$)alkylene-C(O)N($R^5$)$R^6$. In certain other embodiments, $R^4$ is —$CH_2$—C(O)N($R^5$)$R^6$. In certain other embodiments, $R^4$ is —($C_1$-$C_6$)alkylene-C(O)$NH_2$. In certain other embodiments, $R^4$ is —$CH_2$—C(O)$NH_2$.

In certain embodiments, $X^1$ is —C(O)N($R^5$)$R^6$. In certain other embodiments, $X^1$ is —N($R^5$)C(O)$R^6$. In certain other embodiments, $X^1$ is —$CO_2R^6$. In certain other embodiments, $X^1$ is —N($R^5$)$R^6$.

In certain embodiments, $R^5$ and $R^6$ each represent independently hydrogen or —($C_1$-$C_6$)alkyl. In certain other embodiments, $R^5$ and $R^6$ are hydrogen.

The description above describes multiple embodiments relating to compounds of Formula I. The patent application specifically contemplates all combinations of the embodiments.

In certain embodiments, the compound is a compound of Formula I-A:

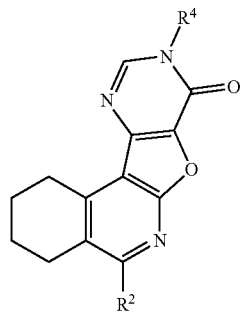

(I-A)

or a pharmaceutically acceptable salt thereof, wherein:

$R^2$ is —($C_1$-$C_6$)alkyl or phenyl, wherein said phenyl is optionally substituted with 1, 2, or 3 substituents independently selected from the group consisting of halogen, —($C_1$-$C_6$)alkyl, —($C_3$-$C_6$)cycloalkyl, hydroxyl, and —($C_1$-$C_6$)alkoxy;

$R^4$ is —($C_1$-$C_6$)alkylene-$X^1$ or —($C_3$-$C_6$)cycloalkyl-$X^1$;

$X^1$ is —C(O)N($R^5$)$R^6$, —N($R^5$)C(O)$R^6$, or —$CO_2R^6$; and $R^5$ and $R^6$ each represent independently hydrogen or —($C_1$-$C_6$)alkyl, or when $R^5$ and $R^6$ are attached to the same nitrogen atom, then $R^5$ and $R^6$ may be taken together with the nitrogen atom to which they are attached to form a 3-7 membered heterocycle.

In certain embodiments, $R^2$ is —($C_1$-$C_6$)alkyl. In certain other embodiments, $R^2$ is methyl, ethyl, n-propyl, or isopropyl. In certain other embodiments, $R^2$ is phenyl. In certain other embodiments, $R^2$ is phenyl substituted with 1, 2, or 3 substituents independently selected from the group consisting of halogen, —($C_1$-$C_6$)alkyl, hydroxyl, and —($C_1$-$C_6$)alkoxy.

In certain embodiments, $R^4$ is —$CH_2$—C(O)N($R^5$)$R^6$. In certain other embodiments, $R^4$ is —($C_1$-$C_6$)alkylene-C(O)$NH_2$. In certain other embodiments, $R^4$ is —$CH_2$—C(O)$NH_2$.

The description above describes multiple embodiments relating to compounds of Formula I-A. The patent application specifically contemplates all combinations of the embodiments.

In certain embodiments, the compound is one of the following or a pharmaceutically acceptable salt thereof:

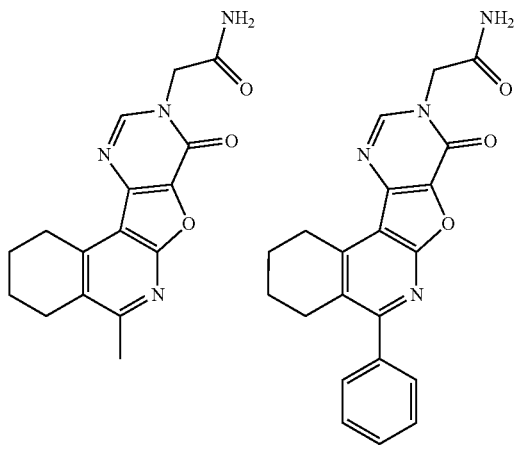 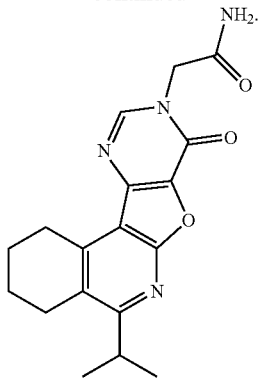

In certain other embodiments, the compound is one of the compounds listed in Table 3 below or a pharmaceutically acceptable salt thereof.

TABLE 3

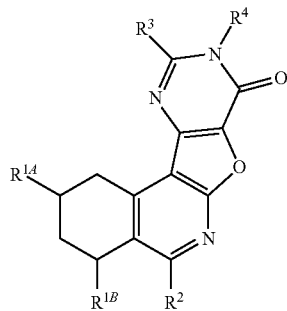

| Compound No. | $R^{1A}$ | $R^{1B}$ | $R^2$ | $R^3$ | $R^4$ |
|---|---|---|---|---|---|
| I-1 | H | H | methyl | H | —CH$_2$CONH$_2$ |
| I-2 | H | H | ethyl | H | —CH$_2$CONH$_2$ |
| I-3 | H | H | phenyl | H | —CH$_2$CONH$_2$ |
| I-4 | H | H | para-chlorophenyl | H | —CH$_2$CONH$_2$ |
| I-5 | H | H | para-methylphenyl | H | —CH$_2$CONH$_2$ |
| I-6 | H | H | meta-methoxyphenyl | H | —CH$_2$CONH$_2$ |
| I-7 | H | H | benzyl | H | —CH$_2$CONH$_2$ |
| I-8 | H | H | para-chlorobenzyl | H | —CH$_2$CONH$_2$ |
| I-9 | H | H | 3-pyridylmethyl | H | —CH$_2$CONH$_2$ |
| I-10 | H | H | (5-methylpyridin-3-yl)methyl | H | —CH$_2$CONH$_2$ |
| I-11 | H | H | (5-chloropyridin-3-yl)methyl | H | —CH$_2$CONH$_2$ |

TABLE 3-continued

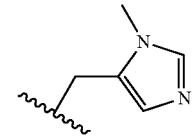 [SMILES: *Cc1cncn1C]

| Compound No. | $R^{1A}$ | $R^{1B}$ | $R^2$ | $R^3$ | $R^4$ |
|---|---|---|---|---|---|
| I-12 | H | H | 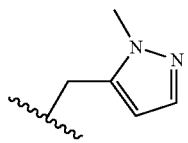 [SMILES: *Cc1ccnn1C] | H | —CH$_2$CONH$_2$ |
| I-13 | H | H | 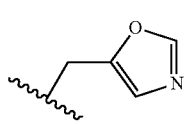 [SMILES: *Cc1cnco1] | H | —CH$_2$CONH$_2$ |
| I-14 | H | H | 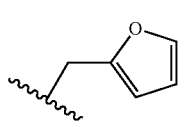 [SMILES: *Cc1ccco1] | H | —CH$_2$CONH$_2$ |
| I-15 | H | H | 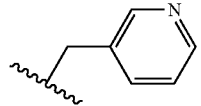 [SMILES: *Cc1cccnc1] | H | —CH$_2$CONH$_2$ |
| I-16 | H | H | methyl | H | —(CH$_2$)$_2$CONH$_2$ |
| I-17 | H | H | ethyl | H | —(CH$_2$)$_2$CONH$_2$ |
| I-18 | CH$_3$ | H | phenyl | H | —(CH$_2$)$_2$CONH$_2$ |
| I-19 | H | CH$_3$ | para-chlorophenyl | H | —(CH$_2$)$_2$CONH$_2$ |
| I-20 | H | H | para-methylphenyl | CH$_3$ | —(CH$_2$)$_2$CONH$_2$ |
| I-21 | CH$_3$ | CH$_3$ | meta-methoxyphenyl | CH$_3$ | —(CH$_2$)$_2$CONH$_2$ |
| I-22 | F | H | benzyl | H | —(CH$_2$)$_2$CONH$_2$ |
| I-23 | H | F | para-chlorobenzyl | H | —(CH$_2$)$_2$CONH$_2$ |
| I-24 | H | H | 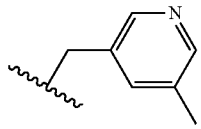 [SMILES: *Cc1cncc(C)c1] | H | —(CH$_2$)$_2$CONH$_2$ |
| I-25 | H | CH$_3$ | 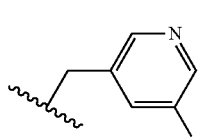 | H | —(CH$_2$)$_2$CONH$_2$ |
| I-26 | H | H | 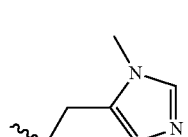 | CH$_3$ | —(CH$_2$)$_2$CONH$_2$ |
| I-27 | CH$_3$ | H |  | CH$_3$ | —(CH$_2$)$_2$CONH$_2$ |

TABLE 3-continued

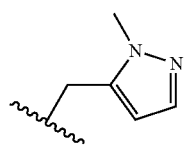 [SMILES: *Cc1ccnn1C]

| Compound No. | $R^{1A}$ | $R^{1B}$ | $R^2$ | $R^3$ | $R^4$ |
| --- | --- | --- | --- | --- | --- |
| I-28 | H | H | 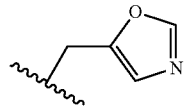 [SMILES: *Cc1cnco1] | H | —(CH$_2$)$_2$CONH$_2$ |
| I-29 | H | CH$_3$ | 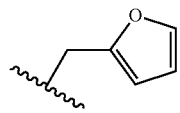 | H | —(CH$_2$)$_2$CONH$_2$ |
| I-30 | H | H | 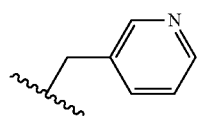 [SMILES: *Cc1cccnc1] | CH$_3$ | —(CH$_2$)$_2$CONH$_2$ |
| I-31 | H | H | methyl | H | —CH$_2$CO$_2$H |
| I-32 | H | H | ethyl | H | —CH$_2$CO$_2$H |
| I-33 | H | H | phenyl | H | —CH$_2$CO$_2$H |
| I-34 | H | H | para-chlorophenyl | H | —CH$_2$CO$_2$H |
| I-35 | H | H | cyclopropyl | H | —CH$_2$CO$_2$H |
| I-36 | H | H | cyclopentyl | H | —CH$_2$CO$_2$H |
| I-37 | H | H | cyclohexyl | H | —CH$_2$CO$_2$H |
| I-38 | H | H | 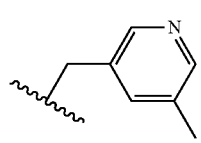 [SMILES: *Cc1cncc(C)c1] | H | —CH$_2$CO$_2$H |
| I-39 | H | H | 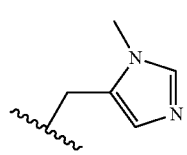 [SMILES: *Cc1cncn1C] | H | —CH$_2$CO$_2$H |
| I-40 | H | H | 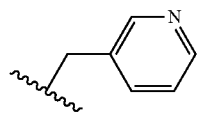 [SMILES: *Cc1cccnc1] | H | —CH$_2$CO$_2$H |
| I-41 | H | H | methyl | H | —CH$_2$CH$_2$—NH$_2$ |
| I-42 | H | H | ethyl | H | —CH$_2$CH$_2$—NH$_2$ |
| I-43 | H | H | phenyl | H | —CH$_2$CH$_2$—NH$_2$ |
| I-44 | H | H | para-chlorophenyl | H | —CH$_2$CH$_2$—NH$_2$ |
| I-45 | H | H | cyclopropyl | H | —CH$_2$CH$_2$—NH$_2$ |
| I-46 | H | H | cylcopentyl | H | —CH$_2$CH$_2$—NH$_2$ |
| I-47 | H | H | cyclohexyl | H | —CH$_2$CH$_2$—NH$_2$ |
| I-48 | H | H |  | H | —CH$_2$CH$_2$—NH$_2$ |

TABLE 3-continued

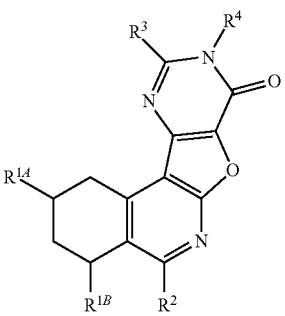

| Compound No. | $R^{1A}$ | $R^{1B}$ | $R^2$ | $R^3$ | $R^4$ |
|---|---|---|---|---|---|
| I-49 | H | H | 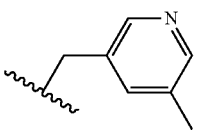 [SMILES: *Cc1cncc(C)c1] | H | —CH$_2$CH$_2$—NH$_2$ |
| I-50 | H | H | 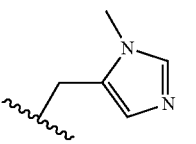 [SMILES: *Cc1cncn1C] | H | —CH$_2$CH$_2$—NH$_2$ |
| I-51 | H | H | methyl | H | —CH$_2$CO$_2$CH$_3$ |
| I-52 | H | H | ethyl | H | —CH$_2$CO$_2$CH$_3$ |
| I-53 | H | H | phenyl | H | —CH$_2$CO$_2$CH$_3$ |
| I-54 | H | H | para-chlorophenyl | H | —CH$_2$CO$_2$CH$_3$ |
| I-55 | H | H | cyclopropyl | H | —CH$_2$CO$_2$CH$_3$ |
| I-56 | H | H | cyclopentyl | H | —CH$_2$CO$_2$CH$_3$ |
| I-57 | H | H | cyclohexyl | H | —CH$_2$CO$_2$CH$_3$ |
| I-58 | H | H | 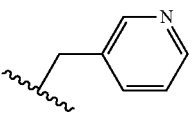 | H | —CH$_2$CO$_2$CH$_3$ |
| I-59 | H | H | 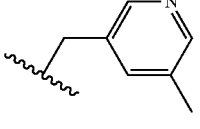 | H | —CH$_2$CO$_2$CH$_3$ |
| I-60 | H | H | 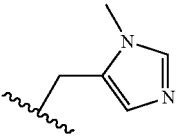 [SMILES: *Cc1cncn1C] | H | —CH$_2$CO$_2$CH$_3$ |

Methods for preparing compounds described herein are illustrated in the following synthetic schemes. These schemes are given for the purpose of illustrating the invention, and should not be regarded in any manner as limiting the scope or the spirit of the invention. Starting materials shown in the schemes can be obtained from commercial sources or can be prepared based on procedures described in the literature.

The synthetic route illustrated in Scheme IV-1 depicts exemplary procedures for preparing amines, carboxylic acids, alkyl esters, and aldehyde compounds starting from amide A, which is commercially available when, for example, R is methyl, ethyl, or phenyl. In the first step, amide A is subjected to acid-catalyzed hydrolysis, such as using hydrochloric acid and water, to provide carboxylic acid C. If desired, carboxylic acid C can be subjected to an esterification reaction with an alcohol, such as methanol, to produce ester compound D. Esterification reactions are well known in the literature and such reactions are often performed using an acid catalyst, such as hydrochloric acid. Selective reduction of the ester group in compound D provides aldehyde E, and such reductions can be carried out using procedures described in the literature, such as selective reduction using diisobutylaluminum hydride at low temperature. Separately, if desired, amine compound B can be prepared from amide A by selective reduction of the exocyclic amide group. Also, if desired, the exocyclic amide group in compound A or the primary amino group in compound B can be alkylated, such as by reacting with one equivalent of methyl iodide in the presence of a hindered base, to provide a monoalkylated amide or amine, respectively.

Joshi-Pangu et al. in *J. Org. Chem.*, 2012, vol. 77, 6629-6633. Next, alkylboronate E1 is subjected to palladium coupling conditions with an aryl bromide, heteroaryl bro-

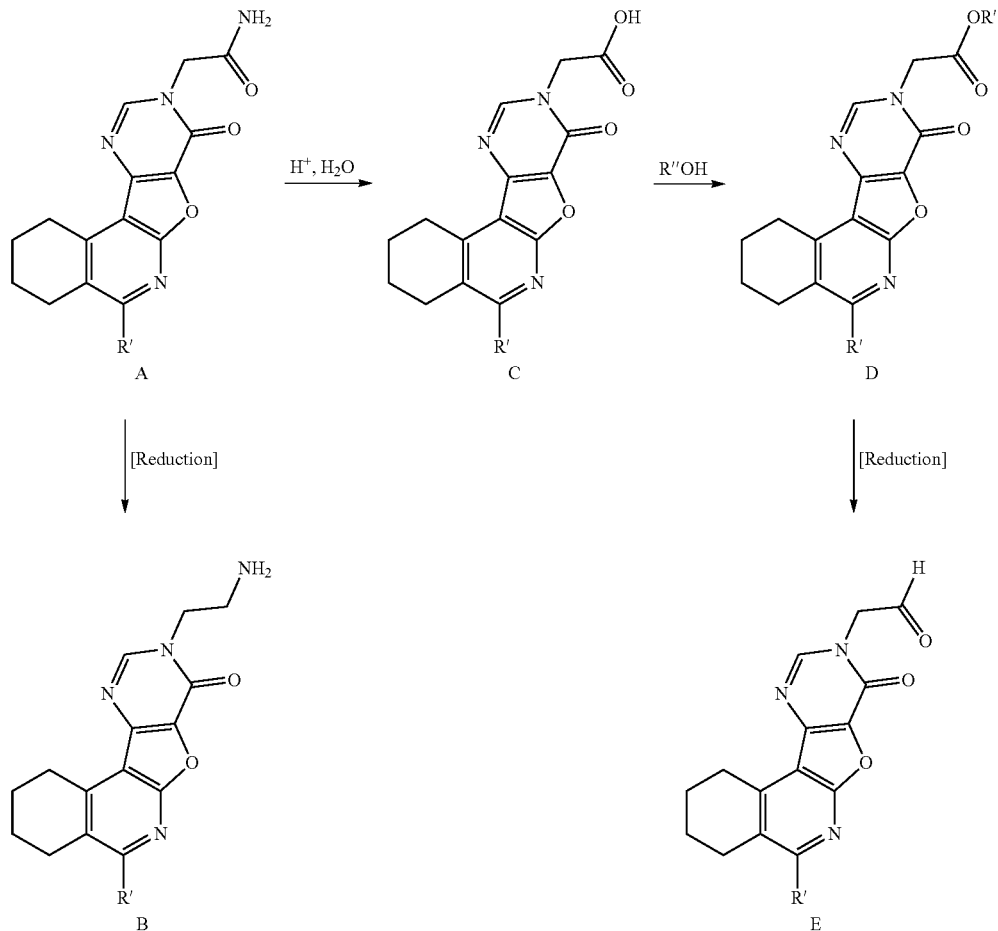

SCHEME IV-1.

R' is, for example, aryl, heteroaryl, aralkyl, heteroaralkyl, alkyl, or cycloalkyl.
R" is, for example, alkyl.

A variety of substituents can be attached to the pyridinyl portion of the multicyclic core of tetrahydropyrimido-furo-isoquinolinones. An exemplary procedure for installing such substituents is illustrated in Scheme IV-2 below. Starting from commercially available amide A1, a protecting group is installed on the exocyclic amide to form compound B1. Various protecting groups are described in the literature, and one possible protecting group is —C(O)CH$_2$CH$_2$Si(CH$_3$)$_3$, which is installed by reacting amide A1 with ClC(O)CH$_2$CH$_2$Si(CH$_3$)$_3$ in the presence of a mild base, such as pyridine or imidazole. Then, selective oxidation of the benzylic methyl group on compound B1 provides alcohol C1. Alcohol C1 is converted to bromide D1 using, for example, PBR$_3$ or other agents or procedures known in the art for converting a primary hydroxyl group to a bromide. Bromide D1 is then reacted with bis(pinacolato)diboron in the presence of a palladium catalyst and tBu$_2$MeP.HBF$_4$ to provide alkylboronate E1. For exemplary description of procedures for forming alkylboronates, see, for example, mide, or alkyl bromide to provide compound F1. The protecting group on F1 can be removed, such as by using tetrabutylammonium fluoride when the protecting group is —C(O)CH$_2$CH$_2$Si(CH$_3$)$_3$, to provide final product G1. Further description of functional group conversation procedures are described in, for example, "Comprehensive Organic Synthesis" (B. M. Trost & I. Fleming, eds., 1991-1992); Carey, F. A. and Sundberg, R. J. Advanced Organic Chemistry Part B: Reactions and Synthesis, 3$^{rd}$ Ed.; Plenum Press: New York, 1990; and J. March, Advanced Organic Chemistry, McGraw Hill Book Company, New York, (1992, 4$^{th}$ edition). It is also appreciated that if a particular compound contains a functional group sensitive to one or more of the synthetic transformations described herein, then conventional protecting group strategies are contemplated to be applied. For a description of protecting group strategies and procedures, see, for example, Greene, T. W.; Wuts, P. G. M. *Protective Groups in Organic Synthesis*, 2nd ed.; Wiley, New York, 1991.

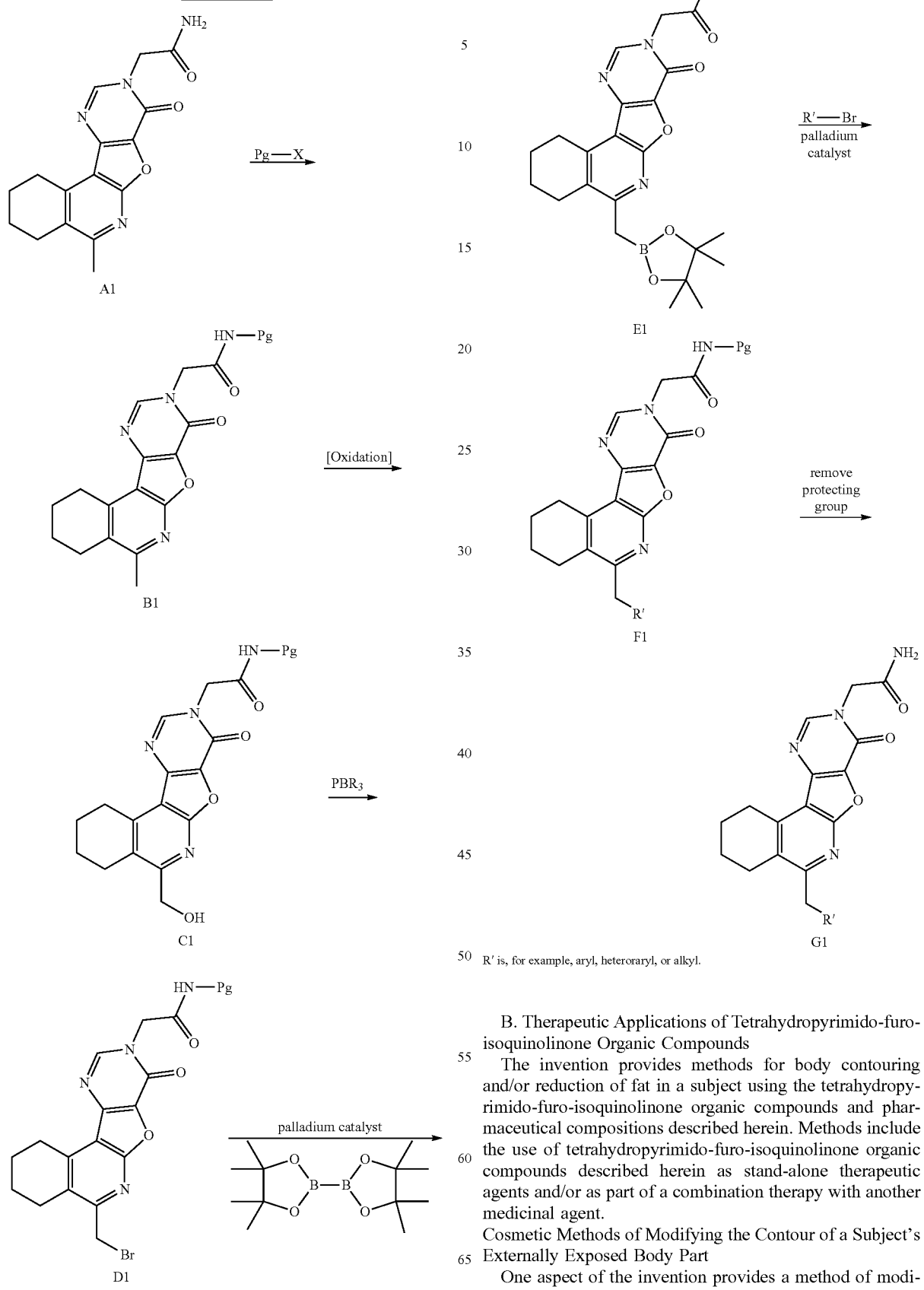

R' is, for example, aryl, heteroaryl, or alkyl.

B. Therapeutic Applications of Tetrahydropyrimido-furo-isoquinolinone Organic Compounds The invention provides methods for body contouring and/or reduction of fat in a subject using the tetrahydropyrimido-furo-isoquinolinone organic compounds and pharmaceutical compositions described herein. Methods include the use of tetrahydropyrimido-furo-isoquinolinone organic compounds described herein as stand-alone therapeutic agents and/or as part of a combination therapy with another medicinal agent.

Cosmetic Methods of Modifying the Contour of a Subject's Externally Exposed Body Part One aspect of the invention provides a method of modifying the contour of a subject's externally exposed body part containing fat. The method comprises administering to said body part an amount of a tetrahydropyrimido-furo-isoquinolinone organic compound described herein, such as a compound of Formula I described above in Sub-Section A, effective to modify the contour of said body part. Formula I, as described above in Sub-Section A, is represented by:

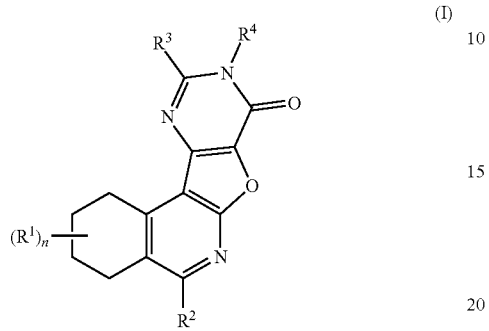

or a pharmaceutically acceptable salt thereof, wherein the variables are as defined in Sub-Section A.

In certain embodiments, the externally exposed body part containing fat is the subject's face, neck, chin, submental region, arm, thigh, knee, calf, buttocks, hips, or abdomen. In certain other embodiments, the externally exposed body part containing fat is the subject's face. In certain other embodiments, the externally exposed body part containing fat is the subject's chin or cheek. In certain embodiments, the externally exposed body part is the subject's neck.

In certain embodiments, the subject experiences at least a 5% by weight reduction in the amount of fat in the subject's body part exposed to said compound. In certain other embodiments, the subject experiences at least a 10% by weight reduction in the amount of fat in the subject's body part exposed to said compound. In certain embodiments, the subject experiences at least a 15% by weight reduction in the amount of fat in the subject's body part exposed to said compound. In certain other embodiments, the subject experiences at least a 25% by weight reduction in the amount of fat in the subject's body part exposed to said compound. In certain other embodiments, the subject experiences from about 1% to about 10%, about 10% to about 20%, about 20% to about 40%, about 40% to about 60%, about 60% to about 80%, about 1% to about 30%, or about 1% to about 50% by weight reduction in the amount of fat in the subject's body part exposed to said compound.

In certain embodiments, the administering comprises injecting said compound into said body part.

In certain embodiments, the subject is an adult human. In certain embodiments, the subject is an animal, such as dog or cat.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing the Amount of Subcutaneous Fat

Another aspect of the invention provides a method of reducing the amount of subcutaneous fat in a subject. The method comprises exposing subcutaneous fat in a subject to an effective amount of a tetrahydropyrimido-furo-isoquinolinone organic compound described herein, such as a compound of Formula I described above in Sub-Section A, to reduce the amount of subcutaneous fat in said subject. Formula I, as described above in Sub-Section A, is represented by:

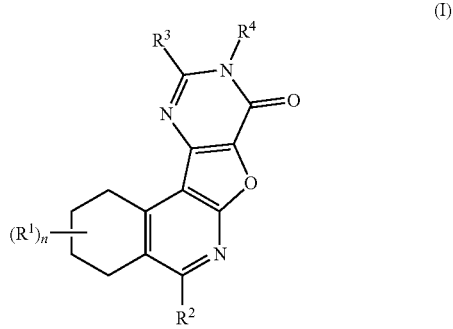

or a pharmaceutically acceptable salt thereof, wherein the variables are as defined in Sub-Section A.

In certain embodiments, the subcutaneous fat is located in the subject's face, neck, chin, submental region, arm, thigh, knee, calf, buttocks, hips, or abdomen. In certain other embodiments, the subcutaneous fat is located in subject's face. In certain other embodiments, the subcutaneous fat is located in subject's neck.

In certain embodiments, the subject experiences at least a 5% by weight reduction in the amount of subcutaneous fat in the subject's body part exposed to said compound. In certain other embodiments, the subject experiences at least a 10% by weight reduction in the amount of subcutaneous fat in the subject's body part exposed to said compound. In certain embodiments, the subject experiences at least a 15% by weight reduction in the amount of subcutaneous fat in the subject's body part exposed to said compound. In certain other embodiments, the subject experiences at least a 25% by weight reduction in the amount of subcutaneous fat in the subject's body part exposed to said compound. In certain other embodiments, the subject experiences 1% to about 10%, about 10% to about 20%, about 20% to about 40%, about 40% to about 60%, about 60% to about 80%, about 1% to about 30%, or about 1% to about 50% by weight reduction in the amount of subcutaneous fat in the subject's body part exposed to said compound.

In certain embodiments, said exposing comprises injecting said compound of Formula I into a region of subcutaneous fat.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Inducing Retraction of Dermal Tissue

Another aspect of the invention provides a method for inducing retraction of dermal tissue in a subject. The method comprises administering an effective amount of a tetrahydropyrimido-furo-isoquinolinone organic compound described herein, such as a compound of Formula I described above in Sub-Section A, to dermal tissue of a subject to induce retraction of dermal tissue. Formula I, as described above in Sub-Section A, is represented by:

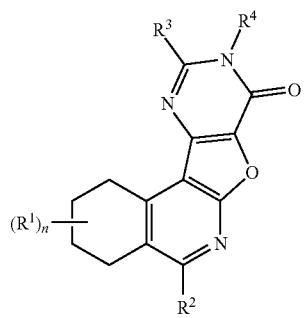

(I)

or a pharmaceutically acceptable salt thereof, wherein the variables are as defined in Sub-Section A.

In certain embodiments, said administering comprises injecting said compound into dermal tissue.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Inducing Retraction of Subcutaneous Tissue

Another aspect of the invention provides a method for inducing retraction of subcutaneous tissue in a subject. The method comprises administering an effective amount of a tetrahydropyrimido-furo-isoquinolinone organic compound described herein, such as a compound of Formula I described above in Sub-Section A, to subcutaneous tissue of a subject to induce retraction of subcutaneous tissue. Formula I, as described above in Sub-Section A, is represented by:

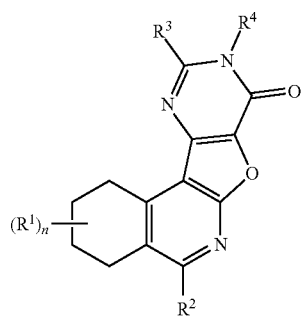

(I)

or a pharmaceutically acceptable salt thereof, wherein the variables are as defined in Sub-Section A.

In certain embodiments, said administering comprises injecting said compound into subcutaneous tissue.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Preventing Accumulation of Fat

Another aspect of the invention provides a method of preventing the accumulation of fat in a subject. The method comprises administering to a subject in need thereof an effective amount of a tetrahydropyrimido-furo-isoquinolinone organic compound described herein, such as a compound of Formula I described above in Sub-Section A, to prevent accumulation of fat in the subject. Formula I, as described above in Sub-Section A, is represented by:

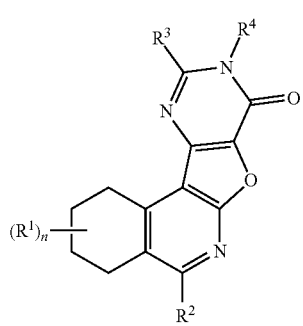

(I)

or a pharmaceutically acceptable salt thereof, wherein the variables are as defined in Sub-Section A.

In certain embodiments, the fat is subcutaneous fat.

In certain embodiments, the accumulation of fat in a subject occurs in the subject's face, neck, chin, submental region, arm, thigh, knee, calf, buttocks, hips, or abdomen.

In certain embodiments, said administering comprises injecting said compound into tissue in the region in which accumulation of fat is to be prevented.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Treating Medical Disorders

Another aspect of the invention provides a method of treating a disorder selected from the group consisting of an adipose tissue tumor, fat embolism, dyslipidemia, or fatty liver disease in a subject. The method comprises administering to a subject in need thereof a therapeutically effective amount of a tetrahydropyrimido-furo-isoquinolinone organic compound described herein, such as a compound of Formula I described above in Sub-Section A, to treat the disorder. Formula I, as described above in Sub-Section A, is represented by:

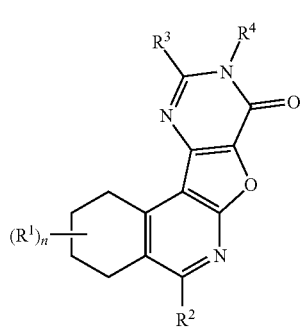

(I)

or a pharmaceutically acceptable salt thereof, wherein the variables are as defined in Sub-Section A.

In certain embodiments, the disorder is an adipose tissue tumor (e.g., a lipoma). For example, in certain embodiments, the lipoma is an adenolipoma, angiolipoleiomyoma, angiolipoma, chondroid lipoma, corpus callosum lipoma, hibernoma, intradermal spindle cell lipoma, neural fibrolipoma, pleomorphic lipoma, spindle-cell lipoma, or a superficial subcutaneous lipoma.

In certain embodiments, the disorder is fat embolism. In certain other embodiments, the disorder is dyslipidemia. In certain other embodiments, the disorder is fatty liver disease. In certain embodiments, the disorder is fatty liver disease due to alcohol-induced liver cirrhosis.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing the Amount of Fat or Cholesterol

Another aspect of the invention provides a method of reducing the amount of fat or cholesterol in a subject. The method comprises administering to a subject in need thereof an effective amount of a tetrahydropyrimido-furo-isoquinolinone organic compound described herein, such as a compound of Formula I described above in Sub-Section A, to reduce the amount of fat or cholesterol in the subject. Formula I, as described above in Sub-Section A, is represented by:

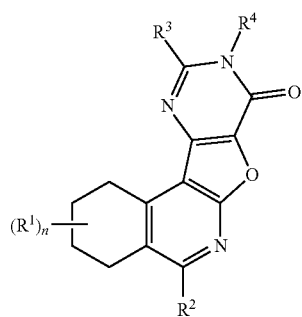

or a pharmaceutically acceptable salt thereof, wherein the variables are as defined in Sub-Section A.

In certain embodiments, the method reduces the amount of fat in a subject.

In certain embodiments, the method improves regulation of energy balance in the subject, lipid homeostatis, insulin sensitivity, blood pressure homeostatis, or vascular health of the subject.

In certain embodiments, the method reduces the amount of cholesterol in a subject.

In certain embodiments, the subject suffers from a cardiovascular disease. For example, in certain embodiments, the cardiovascular disease is coronary artery disease or peripheral vascular disease.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing the Amount of Mesenchymal Pre-adipocyte Stem Cell Precursors Another aspect of the invention provides a method of reducing the amount of mesenchymal pre-adipocyte stem cell precursors in a subject. The method comprises administering to a subject in need thereof an effective amount of a tetrahydropyrimido-furo-isoquinolinone organic compound described herein, such as a compound of Formula I described above in Sub-Section A, to reduce the amount of mesenchymal pre-adipocyte stem cell precursors in the subject. Formula I, as described above in Sub-Section A, is represented by:

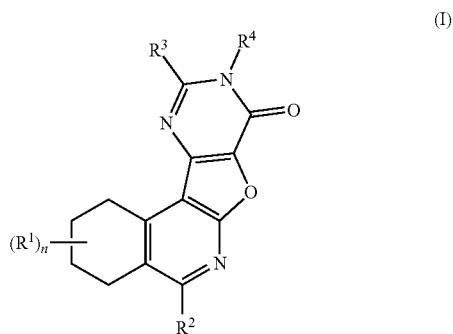

or a pharmaceutically acceptable salt thereof, wherein the variables are as defined in Sub-Section A.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Inducing Death of Adipocyte Cells

Another aspect of the invention provides a method of inducing the death of an adipocyte cell. The method comprises exposing an adipocyte cell to an effective amount of a tetrahydropyrimido-furo-isoquinolinone organic compound described herein, such as a compound of Formula I described above in Sub-Section A, to induce death of the adipocyte cell. Formula I, as described above in Sub-Section A, is represented by:

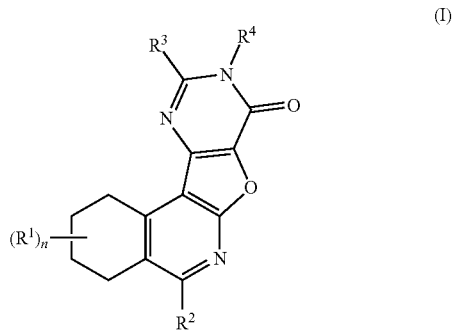

or a pharmaceutically acceptable salt thereof, wherein the variables are as defined in Sub-Section A.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing Skin Aging

Another aspect of the invention provides a method of reducing skin aging in a subject. The method comprises administering to a subject in need thereof an effective amount of a tetrahydropyrimido-furo-isoquinolinone organic compound described herein, such as a compound of Formula I described above in Sub-Section A, to reduce the effects of skin aging. Formula I, as described above in Sub-Section A, is represented by:

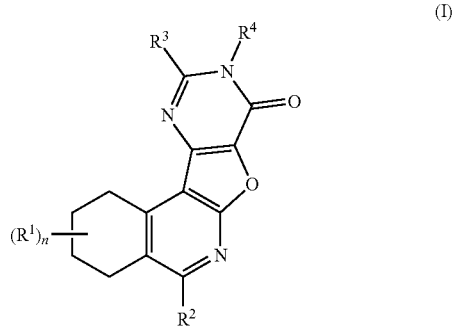

or a pharmaceutically acceptable salt thereof, wherein the variables are as defined in Sub-Section A.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

The description above describes multiple embodiments relating to various methods, such as methods of body contouring and/or reducing fat in a subject using certain tetrahydropyrimido-furo-isoquinolinone organic compounds. The patent application specifically contemplates all combinations of the embodiments. For example, the invention contemplates body contouring and/or reducing fat in a subject by administering a therapeutically effective amount of a compound of Formula I-A.

Combination Therapy

As indicated above, the invention embraces combination therapy, which includes the administration of a tetrahydropyrimido-furo-isoquinolinone organic compound described herein (such as compound of Formula I or I-A described above in Sub-Section A) and a second agent as part of a specific treatment regimen intended to provide the beneficial effect from the co-action of these therapeutic agents. The beneficial effect of the combination may include pharmacokinetic or pharmacodynamic co-action resulting from the combination of therapeutic agents.

C. Pharmaceutical Compositions Containing Tetrahydropyrimido-furo-isoquinolinone Organic Compounds The invention provides pharmaceutical compositions comprising a tetrahydropyrimido-furo-isoquinolinone organic compound described herein, such as a compound of Formula I or I-A described above in Sub-Section A, and a pharmaceutically acceptable carrier. In certain embodiments, the pharmaceutical compositions preferably comprise an effective amount of one or more of the tetrahydropyrimido-furo-isoquinolinone organic compounds described above (i.e., an amount effective to achieve one or more of the therapeutic applications described above in Sub-Section B), formulated together with one or more pharmaceutically acceptable carriers (additives) and/or diluents. As described in detail below in Section VI, pharmaceutical compositions of the present invention may be specially formulated for administration in solid or liquid form, including those adapted for the following: (1) parenteral administration by, for example, subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) oral administration, for example, drenches (aqueous or non-aqueous solutions or suspensions), tablets (e.g., those targeted for buccal, sublingual, and/or systemic absorption), boluses, powders, granules, pastes for application to the tongue; (4) intravaginally or intrarectally, for example, as a pessary, cream or foam; (5) sublingually; (6) occularly; (7) transdermally; or (8) nasally.

D. Medical Kits Containing Tetrahydropyrimido-furo-isoquinolinone Organic Compounds Another aspect of the invention provides a kit for body contouring and/or reducing the amount of fat in a subject. The kit comprises: i) instructions for body contouring and/or reducing the amount of fat in a subject (for example, modifying the contour of a subject's externally exposed body part containing fat; reducing the amount of subcutaneous fat in a subject; inducing retraction of dermal tissue or subcutaneous tissue in a subject; preventing the accumulation of fat in a subject; treating a disorder selected from the group consisting of an adipose tissue tumor (e.g., a lipoma), fat embolism, dyslipidemia, or fatty liver disease in a subject; reducing the amount of fat or cholesterol in a subject; and reducing the amount of mesenchymal pre-adipocyte stem cell precursors in a subject); and ii) a tetrahydropyrimido-furo-isoquinolinone organic compound described herein, such as a compound of Formula I described above in Sub-Section A. The kit may comprise one or more unit dosage forms containing an amount of a tetrahydropyrimido-furo-isoquinolinone organic compound described herein, such as a compound of Formula I described above in Sub-Section A, that is effective for body contouring and/or reduction of fat in a subject.

The description above describes multiple aspects and embodiments of the invention, including tetrahydropyrimido-furo-isoquinolinone organic compounds, compositions comprising tetrahydropyrimido-furo-isoquinolinone organic compounds, methods of using the tetrahydropyrimido-furo-isoquinolinone organic compounds, and kits. The patent application specifically contemplates all combinations and permutations of the aspects and embodiments. For example, the invention contemplates body contouring and/or reducing fat in a human patient by administering a therapeutically effective amount of a compound of Formula I-A described above in Sub-Section A. Further, for example, the invention contemplates a kit for body contouring and/or reduction of fat in a subject, the kit comprising instructions for body contouring and/or reducing fat in a subject and ii) a tetrahydropyrimido-furo-isoquinolinone organic compound described herein, such as a compound of Formula I-A described above in Sub-Section A.

V. Tetrahydrobenzo[4,5]Imidazo[1,2-A]Pyrazine Organic Compounds & Their Use

Certain aspects of the invention provide tetrahydrobenzo[4,5]imidazo[1,2-a]pyrazine organic compounds, pharmaceutical compositions containing such compounds, medical kits, and therapeutic applications using such compounds. These compounds, pharmaceutical compositions, medical kits, and therapeutic applications are described in more detail in the sections below.

A. Tetrahydrobenzo[4,5]Imidazo[1,2-a]Pyrazine Organic Compounds

One aspect of the invention provides tetrahydrobenzo[4,5]imidazo[1,2-a]pyrazine organic compounds. The tetrahydrobenzo[4,5]imidazo[1,2-a]pyrazine organic compounds are contemplated to be useful in the methods, compositions, and kits described herein. In certain embodiments, the tetrahydrobenzo[4,5]imidazo[1,2-a]pyrazine organic compound is a compound embraced by Formula I:

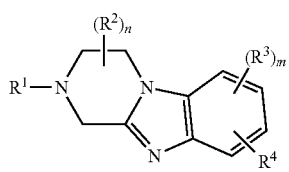

(I)

or a pharmaceutically acceptable salt thereof, wherein:

$R^1$ is phenyl, 5-6 membered heteroaryl, aralkyl, —($C_1$-$C_6$)alkyl, —($C_3$-$C_6$)cycloalkyl —($C_1$-$C_6$)alkylene-OH, or —($C_1$-$C_6$)alkylene-O—($C_1$-$C_6$)alkyl, wherein said phenyl, 5-6 membered heteroaryl, aralkyl, and cycloalkyl are optionally substituted with 1, 2, or 3 substituents independently selected from the group consisting of halogen, —($C_1$-$C_6$)alkyl, —($C_3$-$C_6$)cycloalkyl, hydroxyl, —($C_1$-$C_6$)alkoxy, and —N($R^5$)$R^6$;

$R^2$ and $R^3$ each represent independently for each occurrence hydrogen, —($C_1$-$C_6$)alkyl, or halogen;

$R^4$ is —C(O)N($R^5$)$R^6$, —N($R^5$)C(O)$R^6$, —CO$_2$$R^6$, —C(O)$R^6$, —($C_1$-$C_6$)alkylene-N($R^5$)$R^6$, —($C_1$-$C_6$)alkylene-O$R^6$, or —($C_1$-$C_6$)alkoxy; and $R^5$ and $R^6$ each represent independently for each occurrence hydrogen, —($C_1$-$C_6$)alkyl, or —($C_3$-$C_6$)cycloalkyl; or when $R^5$ and $R^6$ are attached to the same nitrogen atom, then $R^5$ and $R^6$ may be taken together with the nitrogen atom to which they are attached to form a 3-7 membered heterocycle; and n and m each represent independently 1 or 2.

In certain embodiments, $R^1$ is phenyl substituted with 1, 2, or 3 substituents independently selected from the group consisting of halogen, —($C_1$-$C_6$)alkyl, —($C_3$-$C_6$)cycloalkyl, hydroxyl, —($C_1$-$C_6$)alkoxy, and —N($R^5$)$R^6$. In certain other embodiments, $R^1$ is phenyl substituted with a methoxy group and optionally 1 or 2 additional substituents independently selected from the group consisting of halogen and —($C_1$-$C_6$)alkyl. In certain other embodiments, $R^1$ is methoxyphenyl. In certain other embodiments, $R^1$—($C_1$-$C_6$)alkylene-OH.

In certain embodiments, $R^2$ and $R^3$ are hydrogen.

In certain embodiments, $R^4$ is —C(O)N($R^5$)$R^6$. In certain other embodiments, $R^4$ is —C(O)NH$_2$.

The description above describes multiple embodiments relating to compounds of Formula I. The patent application specifically contemplates all combinations of the embodiments.

In certain embodiments, the compound is a compound of Formula I-A:

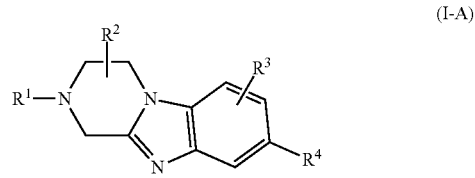

(I-A)

or a pharmaceutically acceptable salt thereof, wherein:

$R^1$ is phenyl, —($C_1$-$C_6$)alkylene-OH, or —($C_1$-$C_6$)alkylene-O—($C_1$-$C_6$)alkyl, wherein said phenyl is optionally substituted with 1, 2, or 3 substituents independently selected from the group consisting of halogen, —($C_1$-$C_6$)alkyl, —($C_3$-$C_6$)cycloalkyl, hydroxyl, and —($C_1$-$C_6$)alkoxy;

$R^2$ and $R^3$ each represent independently for each occurrence hydrogen and methyl;

$R^4$ is —C(O)N($R^5$)$R^6$, —N($R^5$)C(O)$R^6$, or —($C_1$-$C_2$)alkylene-N($R^5$)$R^6$; and $R^5$ and $R^6$ each represent independently hydrogen, —($C_1$-$C_6$)alkyl, or —($C_3$-$C_6$)cycloalkyl; or when $R^5$ and $R^6$ are attached to the same nitrogen atom, then $R^5$ and $R^6$ may be taken together with the nitrogen atom to which they are attached to form a 3-7 membered heterocycle.

In certain embodiments, $R^1$ is phenyl substituted with 1, 2, or 3 substituents independently selected from the group consisting of —($C_1$-$C_3$)alkyl, —($C_3$-$C_6$)cycloalkyl, hydroxyl, and —($C_1$-$C_6$)alkoxy. In certain other embodiments, $R^1$ is phenyl substituted with a methoxy group and optionally 1 or 2 —($C_1$-$C_6$)alkyl groups. In certain other embodiments, $R^1$ is methoxyphenyl. In certain other embodiments, $R^1$—($C_1$-$C_6$)alkylene-OH.

In certain embodiments, $R^4$ is —C(O)N($R^5$)$R^6$. In certain other embodiments, $R^4$ is —C(O)NH$_2$.

The description above describes multiple embodiments relating to compounds of Formula I-A. The patent application specifically contemplates all combinations of the embodiments.

In certain embodiments, the compound is one of the following or a pharmaceutically acceptable salt thereof:

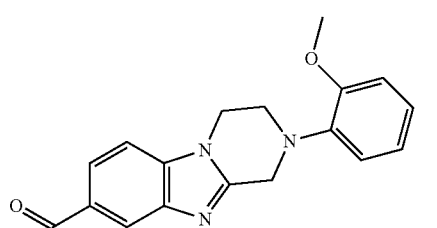

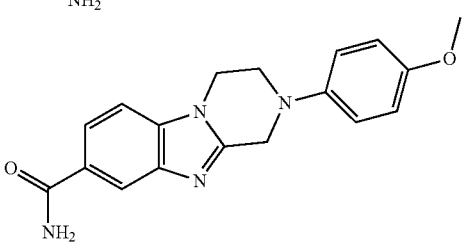

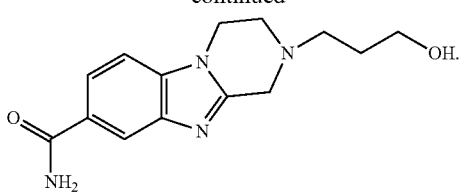

In certain other embodiments, the compound is one of the compounds listed in Table 4 below or a pharmaceutically acceptable salt thereof.

TABLE 4

| Compound No. | $R^1$ | $R^2$ | $R^3$ | $R^4$ |
|---|---|---|---|---|
| I-1 | 2-methoxy-phenyl | H | H | —$CONH_2$ |
| I-2 | 3-methoxy-phenyl | H | H | —$CONH_2$ |
| I-3 | 4-methoxy-phenyl | H | H | —$CONH_2$ |
| I-4 | 2-methoxy-4-methyl-phenyl | H | H | —$CONH_2$ |
| I-5 | 2-methyl-4-methoxy-phenyl | H | H | —$CONH_2$ |
| I-6 | 2-methoxy-4-cyclopropyl-phenyl | H | H | —$CONH_2$ |
| I-7 | benzyl | H | H | —$CONH_2$ |
| I-8 | 4-methoxy-benzyl | H | H | —$CONH_2$ |
| I-9 | —$(CH_2)_3$—OH | H | H | —$CONH_2$ |
| I-10 | —$(CH_2)_2$—OH | H | H | —$CONH_2$ |
| I-11 | —$CH_2CH(CH_3)$—OH | H | H | —$CONH_2$ |
| I-12 | 4-hydroxy-cyclohexyl | H | H | —$CONH_2$ |
| I-13 | 3-hydroxy-cyclobutyl | H | H | —$CONH_2$ |
| I-14 | pyridin-3-yl | H | H | —$CONH_2$ |
| I-15 | 5-methoxy-pyridin-3-yl | H | H | —$CONH_2$ |
| I-16 | 1-methyl-pyrrol-2-yl | H | H | —$CONH_2$ |
| I-17 | 1-methyl-imidazol-5-yl | H | H | —$CONH_2$ |
| I-18 | —$(CH_2)_3$—$OCH_3$ | H | H | —$CONH_2$ |
| I-19 | —$(CH_2)_2$—$OCH_3$ | H | H | —$CONH_2$ |
| I-20 | 4-methoxy-cyclohexyl | H | H | —$CONH_2$ |
| I-21 | 2-methoxy-phenyl | $CH_3$ | H | —$CONH_2$ |
| I-22 | 3-methoxy-phenyl | H | $CH_3$ | —$CONH_2$ |
| I-23 | 4-methoxy-phenyl | $CH_3$ | $CH_3$ | —$CONH_2$ |
| I-24 | 2-methoxy-4-methyl-phenyl | H | $CH_3$ | —$CONH_2$ |
| I-25 | 2-methyl-4-methoxy-phenyl | H | $CH_3$ | —$CONH_2$ |
| I-26 | 2-methoxy-4-cyclopropyl-phenyl | $CH_3$ | $CH_3$ | —$CONH_2$ |
| I-27 | benzyl | $CH_3$ | H | —$CONH_2$ |
| I-28 | 4-methoxy-benzyl | H | $CH_3$ | —$CONH_2$ |
| I-29 | —$(CH_2)_3$—OH | $CH_3$ | $CH_3$ | —$CONH_2$ |
| I-30 | —$(CH_2)_2$—OH | $CH_3$ | H | —$CONH_2$ |
| I-31 | —$CH_2CH(CH_3)$—OH | H | $CH_3$ | —$CONH_2$ |
| I-32 | 4-hydroxy-cyclohexyl | $CH_3$ | $CH_3$ | —$CONH_2$ |

TABLE 4-continued

| Compound No. | R¹ | R² | R³ | R⁴ |
|---|---|---|---|---|
| I-33 | 3-hydroxycyclobutyl | CH₃ | H | —CONH₂ |
| I-34 | pyridin-3-yl | H | CH₃ | —CONH₂ |
| I-35 | 5-methoxypyridin-3-yl | CH₃ | F | —CONH₂ |
| I-36 | 1-methyl-1H-pyrrol-2-yl | F | H | —CONH₂ |
| I-37 | 1-methyl-1H-imidazol-5-yl | H | F | —CONH₂ |
| I-38 | —(CH₂)₃—OCH₃ | CH₃ | Cl | —CONH₂ |
| I-39 | —(CH₂)₂—OCH₃ | Cl | H | —CONH₂ |
| I-40 | 4-methoxycyclohexyl | H | Cl | —CONH₂ |
| I-41 | 2-methoxy-phenyl | H | H | —CON(H)CH₃ |
| I-42 | 3-methoxy-phenyl | H | H | —CON(H)CH₃ |
| I-43 | 4-methoxy-phenyl | H | H | —CON(H)CH₃ |
| I-44 | 2-methoxy-4-methylphenyl | H | H | —CON(H)CH₃ |
| I-45 | 4-methoxy-2-methylphenyl | H | H | —CON(H)CH₃ |
| I-46 | 4-cyclopropyl-2-methoxyphenyl | H | H | —CON(H)CH₂CH₃ |
| I-47 | benzyl | H | H | —CON(H)CH₂CH₃ |
| I-48 | 4-methoxy-benzyl | H | H | —CON(H)CH₂CH₃ |
| I-49 | —(CH₂)₃—OH | H | H | —CON(H)CH₂CH₃ |
| I-50 | —(CH₂)₂—OH | H | H | —CON(H)CH₂CH₃ |
| I-51 | 2-methoxy-phenyl | H | H | —CO₂H |
| I-52 | 3-methoxy-pehnyl | H | H | —CO₂H |
| I-53 | 4-methoxy-phenyl | H | H | —CO₂H |
| I-54 | 2-methoxy-4-methylphenyl | H | H | —CO₂H |
| I-55 | 4-methoxy-2-methylphenyl | H | H | —CO₂H |
| I-56 | 4-cyclopropyl-2-methoxyphenyl | H | H | —CO₂H |
| I-57 | benzyl | H | H | —CO₂H |
| I-58 | 4-methoxy-benzyl | H | H | —CO₂H |
| I-59 | —(CH₂)₃—OH | H | H | —CO₂H |
| I-60 | —(CH₂)₂—OH | H | H | —CO₂H |
| I-61 | 2-methoxy-phenyl | H | H | —CO₂CH₃ |
| I-62 | 3-methoxy-phenyl | H | H | —CO₂CH₃ |
| I-63 | 4-methoxy-phenyl | H | H | —CO₂CH₃ |
| I-64 | 2-methoxy-4-methylphenyl | H | H | —CO₂CH₃ |
| I-65 | 4-methoxy-2-methylphenyl | H | H | —CO₂CH₃ |
| I-66 | 4-cyclopropyl-2-methoxyphenyl | H | H | —CO₂CH₃ |
| I-67 | benzyl | H | H | —CO₂CH₃ |
| I-68 | 4-methoxy-benzyl | H | H | —CO₂CH₃ |
| I-69 | —(CH₂)₃—OH | H | H | —CO₂CH₃ |
| I-70 | —(CH₂)₂—OH | H | H | —CO₂CH₃ |
| I-71 | 2-methoxy-phenyl | H | H | —CH₂NH₂ |
| I-72 | 3-methoxy-phenyl | H | H | —CH₂NH₂ |
| I-73 | 4-methoxy-phenyl | H | H | —CH₂NH₂ |

TABLE 4-continued

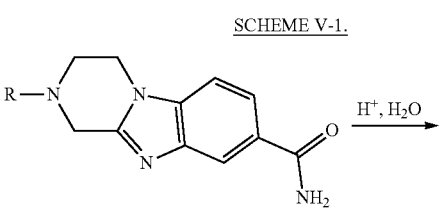

| Compound No. | R¹ | R² | R³ | R⁴ |
|---|---|---|---|---|
| I-74 | MeO-[2-methyl-phenyl] | H | H | —CH₂NH₂ |
| I-75 | [3-methyl-phenyl]-OMe | H | H | —CH₂NH₂ |
| I-76 | MeO-[4-cyclopropyl-phenyl] | H | H | —CH₂NH₂ |
| I-77 | benzyl | H | H | —CH₂NH₂ |
| I-78 | 4-methoxy-benzyl | H | H | —CH₂NH₂ |
| I-79 | —(CH₂)₃—OH | H | H | —CH₂NH₂ |
| I-80 | —(CH₂)₂—OH | H | H | —CH₂NH₂ |

Methods for preparing compounds described herein are illustrated in the following synthetic schemes. These schemes are given for the purpose of illustrating the invention, and should not be regarded in any manner as limiting the scope or the spirit of the invention. Starting materials shown in the schemes can be obtained from commercial sources or can be prepared based on procedures described in the literature.

The synthetic route illustrated in Scheme V-1 depicts exemplary procedures for preparing carboxylic acids, alkyl esters, and ketone compounds starting from aryl amide A, which is commercially available when, for example, R is ortho-methoxyphenyl, para-methoxyphenyl, and 3-hydroxypropyl. In the first step, amide A is subjected to acid-catalyzed hydrolysis, such as using hydrochloric acid and water, to provide carboxylic acid B. If desired, carboxylic acid B can be subjected to an esterification reaction with an alcohol, such as methanol, to produce ester compound C. Esterification reactions are well known in the literature and such reactions are often performed using an acid catalyst, such as hydrochloric acid. Reduction of the ester group in compound C can be performed using literature procedures to provide aldehyde D. Reaction of aldehyde D with a Grignard reagent, such as CH₃MgCl, provides alcohol E that can be oxidized using procedures known in the literature for converting a hydroxyl group to a ketone, such as oxidation using Dess-Martin Periodinane, to provide ketone F. Further description of functional group conversation procedures are described in, for example, "Comprehensive Organic Synthesis" (B. M. Trost & I. Fleming, eds., 1991-1992); Carey, F. A. and Sundberg, R. J. Advanced Organic Chemistry Part B: Reactions and Synthesis, 3$^{rd}$ Ed.; Plenum Press: New York, 1990; and J. March, Advanced Organic Chemistry, McGraw Hill Book Company, New York, (1992, 4$^{th}$ edition). It is appreciated that if a particular compound contains a functional group sensitive to one or more of the synthetic transformations described herein, then conventional protecting group strategies are contemplated to be applied. For a description of protecting group strategies and procedures, see, for example, Greene, T. W.; Wuts, P. G. M. *Protective Groups in Organic Synthesis*, 2$_{nd}$ ed.; Wiley, New York, 1991.

SCHEME V-1.

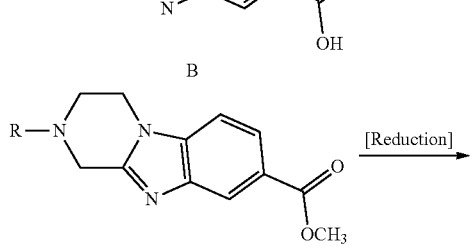

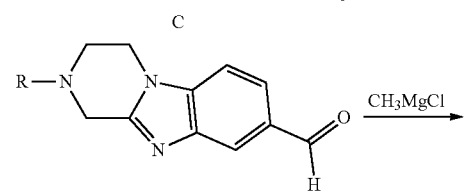

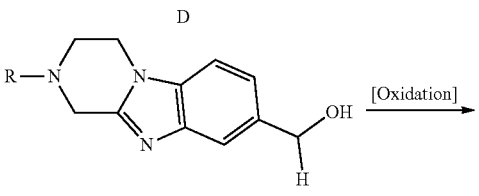

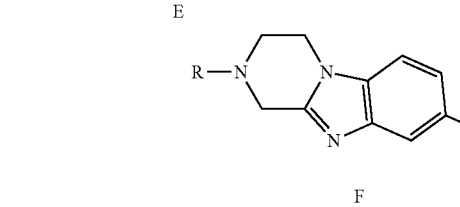

R is, for example, aryl, heteroaryl, cycloalkyl, or alkyl.

The synthetic route illustrated in Scheme V-2 depicts exemplary procedures for preparing amine compounds starting aryl amide A, which is commercially available when, for example, R is ortho-methoxyphenyl, para-methoxyphenyl, and 3-hydroxypropyl. In this procedure, amide A1 is reduced using, for example, lithium aluminum hydride, to provide amine B1.

SCHEME V-2.

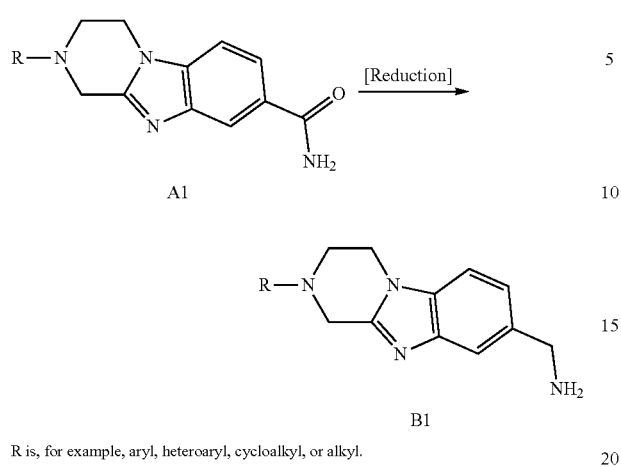

R is, for example, aryl, heteroaryl, cycloalkyl, or alkyl.

The synthetic route illustrated in Scheme V-3 depicts exemplary procedures for attaching various groups to the piperazine nitrogen atom of the tricyclic core of compound A2. The synthetic route involves reacting amine A2 with an aryl bromide or heteroaryl bromide B2 in the presence of a palladium catalyst to provide compound C2. Further description of such palladium coupling reactions are available in the literature. Protecting groups (Pg) can be removed from compound C2 using standard procedures, such as those described in, for example, Greene, T. W.; Wuts, P. G. M. *Protective Groups in Organic Synthesis*, $2_{nd}$ ed.; Wiley, New York, 1991. Such amide protecting groups are commonly known in the literature, such as described in Greene, T. W.; Wuts, P. G. M. *Protective Groups in Organic Synthesis*, $2_{nd}$ ed.; Wiley, New York, 1991. Alternatively, other groups (e.g., alkyl groups, substituted alkyl groups, aralkyl groups, heteroalkyl groups) can be added to the piperazine nitrogen atom of the tricyclic core of compound A2 by reacting compound A2 with an alkyl bromide, substituted alkyl bromide, aralkyl bromide, or heteroaralkyl bromide in an N-alkylation reaction.

SCHEME V-3.

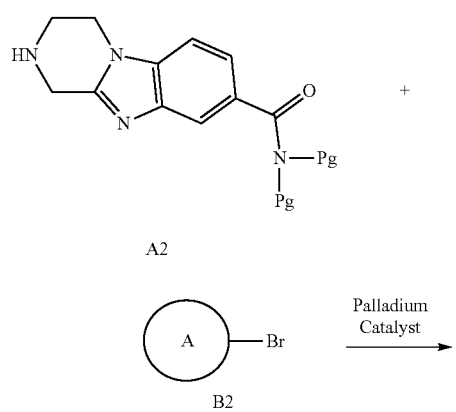

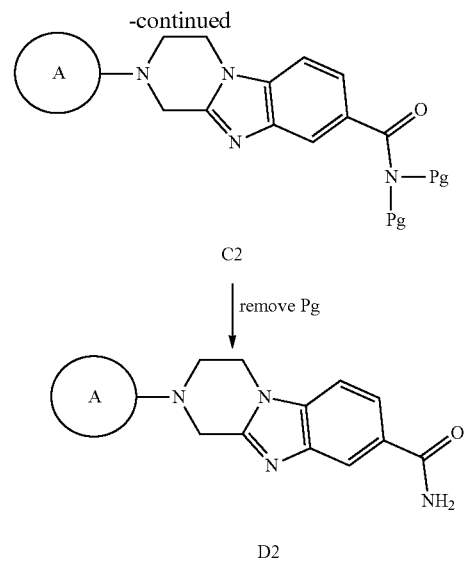

B. Therapeutic Applications of Tetrahydrobenzo[4,5]Imidazo[1,2-a]Pyrazine Organic Compounds The invention provides methods for body contouring and/or reduction of fat in a subject using the tetrahydrobenzo[4,5]imidazo[1,2-a]pyrazine organic compounds and pharmaceutical compositions described herein. Methods include the use of tetrahydrobenzo[4,5]imidazo[1,2-a]pyrazine organic compounds described herein as stand-alone therapeutic agents and/or as part of a combination therapy with another medicinal agent.

Cosmetic Methods of Modifying the Contour of a Subject's Externally Exposed Body Part One aspect of the invention provides a method of modifying the contour of a subject's externally exposed body part containing fat. The method comprises administering to said body part an amount of a tetrahydrobenzo[4,5]imidazo[1,2-a]pyrazine organic compound described herein, such as a compound of Formula I described above in Sub-Section A, effective to modify the contour of said body part. Formula I, as described above in Sub-Section A, is represented by:

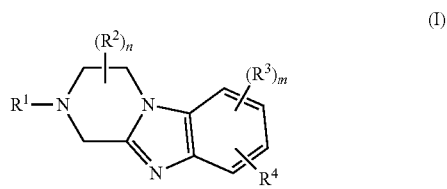

or a pharmaceutically acceptable salt thereof, wherein the variables are as defined in Sub-Section A.

In certain embodiments, the externally exposed body part containing fat is the subject's face, neck, chin, submental region, arm, thigh, knee, calf, buttocks, hips, or abdomen. In certain other embodiments, the externally exposed body part containing fat is the subject's face. In certain other embodiments, the externally exposed body part containing fat is the subject's chin or cheek. In certain embodiments, the externally exposed body part is the subject's neck.

In certain embodiments, the subject experiences at least a 5% by weight reduction in the amount of fat in the subject's body part exposed to said compound. In certain other embodiments, the subject experiences at least a 10% by weight reduction in the amount of fat in the subject's body part exposed to said compound. In certain embodiments, the subject experiences at least a 15% by weight reduction in the amount of fat in the subject's body part exposed to said compound. In certain other embodiments, the subject experiences at least a 25% by weight reduction in the amount of fat in the subject's body part exposed to said compound. In certain other embodiments, the subject experiences from about 1% to about 10%, about 10% to about 20%, about 20% to about 40%, about 40% to about 60%, about 60% to about 80%, about 1% to about 30%, or about 1% to about 50% by weight reduction in the amount of fat in the subject's body part exposed to said compound.

In certain embodiments, the administering comprises injecting said compound into said body part.

In certain embodiments, the subject is an adult human. In certain embodiments, the subject is an animal, such as dog or cat.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing the Amount of Subcutaneous Fat

Another aspect of the invention provides a method of reducing the amount of subcutaneous fat in a subject. The method comprises exposing subcutaneous fat in a subject to an effective amount of a tetrahydrobenzo[4,5]imidazo[1,2-a]pyrazine organic compound described herein, such as a compound of Formula I described above in Sub-Section A, to reduce the amount of subcutaneous fat in said subject. Formula I, as described above in Sub-Section A, is represented by:

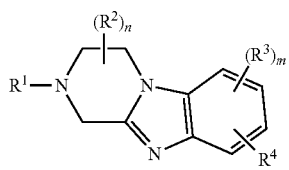

(I)

or a pharmaceutically acceptable salt thereof, wherein the variables are as defined in Sub-Section A.

In certain embodiments, the subcutaneous fat is located in the subject's face, neck, chin, submental region, arm, thigh, knee, calf, buttocks, hips, or abdomen. In certain other embodiments, the subcutaneous fat is located in subject's face. In certain other embodiments, the subcutaneous fat is located in subject's neck.

In certain embodiments, the subject experiences at least a 5% by weight reduction in the amount of subcutaneous fat in the subject's body part exposed to said compound. In certain other embodiments, the subject experiences at least a 10% by weight reduction in the amount of subcutaneous fat in the subject's body part exposed to said compound. In certain embodiments, the subject experiences at least a 15% by weight reduction in the amount of subcutaneous fat in the subject's body part exposed to said compound. In certain other embodiments, the subject experiences at least a 25% by weight reduction in the amount of subcutaneous fat in the subject's body part exposed to said compound. In certain other embodiments, the subject experiences 1% to about 10%, about 10% to about 20%, about 20% to about 40%, about 40% to about 60%, about 60% to about 80%, about 1% to about 30%, or about 1% to about 50% by weight reduction in the amount of subcutaneous fat in the subject's body part exposed to said compound.

In certain embodiments, said exposing comprises injecting said compound of Formula I into a region of subcutaneous fat.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Inducing Retraction of Dermal Tissue

Another aspect of the invention provides a method for inducing retraction of dermal tissue in a subject. The method comprises administering an effective amount of a tetrahydrobenzo[4,5]imidazo[1,2-a]pyrazine organic compound described herein, such as a compound of Formula I described above in Sub-Section A, to dermal tissue of a subject to induce retraction of dermal tissue. Formula I, as described above in Sub-Section A, is represented by:

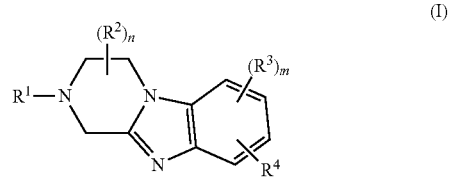

(I)

or a pharmaceutically acceptable salt thereof, wherein the variables are as defined in Sub-Section A.

In certain embodiments, said administering comprises injecting said compound into dermal tissue.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Inducing Retraction of Subcutaneous Tissue

Another aspect of the invention provides a method for inducing retraction of subcutaneous tissue in a subject. The method comprises administering an effective amount of a tetrahydrobenzo[4,5]imidazo[1,2-a]pyrazine organic compound described herein, such as a compound of Formula I described above in Sub-Section A, to subcutaneous tissue of a subject to induce retraction of subcutaneous tissue. Formula I, as described above in Sub-Section A, is represented by:

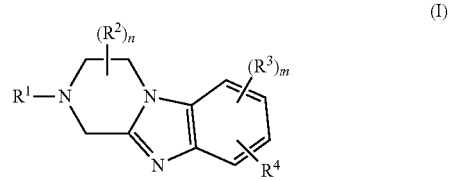

(I)

or a pharmaceutically acceptable salt thereof, wherein the variables are as defined in Sub-Section A.

In certain embodiments, said administering comprises injecting said compound into subcutaneous tissue.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Preventing Accumulation of Fat

Another aspect of the invention provides a method of preventing the accumulation of fat in a subject. The method comprises administering to a subject in need thereof an effective amount of a tetrahydrobenzo[4,5]imidazo[1,2-a]pyrazine organic compound described herein, such as a compound of Formula I described above in Sub-Section A, to prevent accumulation of fat in the subject. Formula I, as described above in Sub-Section A, is represented by:

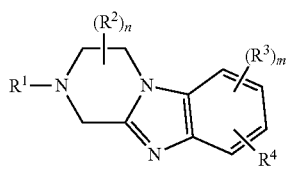

(I)

or a pharmaceutically acceptable salt thereof, wherein the variables are as defined in Sub-Section A.

In certain embodiments, the fat is subcutaneous fat.

In certain embodiments, the accumulation of fat in a subject occurs in the subject's face, neck, chin, submental region, arm, thigh, knee, calf, buttocks, hips, or abdomen.

In certain embodiments, said administering comprises injecting said compound into tissue in the region in which accumulation of fat is to be prevented.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Treating Medical Disorders

Another aspect of the invention provides a method of treating a disorder selected from the group consisting of an adipose tissue tumor, fat embolism, dyslipidemia, or fatty liver disease in a subject. The method comprises administering to a subject in need thereof a therapeutically effective amount of a tetrahydrobenzo[4,5]imidazo[1,2-a]pyrazine organic compound described herein, such as a compound of Formula I described above in Sub-Section A, to treat the disorder. Formula I, as described above in Sub-Section A, is represented by:

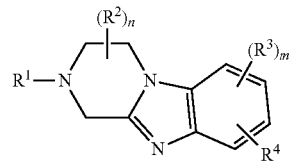

(I)

or a pharmaceutically acceptable salt thereof, wherein the variables are as defined in Sub-Section A.

In certain embodiments, the disorder is an adipose tissue tumor (e.g., a lipoma). For example, in certain embodiments, the lipoma is an adenolipoma, angiolipoleiomyoma, angiolipoma, chondroid lipoma, corpus callosum lipoma, hibernoma, intradermal spindle cell lipoma, neural fibrolipoma, pleomorphic lipoma, spindle-cell lipoma, or a superficial subcutaneous lipoma.

In certain embodiments, the disorder is fat embolism. In certain other embodiments, the disorder is dyslipidemia. In certain other embodiments, the disorder is fatty liver disease. In certain embodiments, the disorder is fatty liver disease due to alcohol-induced liver cirrhosis.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing the Amount of Fat or Cholesterol

Another aspect of the invention provides a method of reducing the amount of fat or cholesterol in a subject. The method comprises administering to a subject in need thereof an effective amount of a tetrahydrobenzo[4,5]imidazo[1,2-a]pyrazine organic compound described herein, such as a compound of Formula I described above in Sub-Section A, to reduce the amount of fat or cholesterol in the subject. Formula I, as described above in Sub-Section A, is represented by:

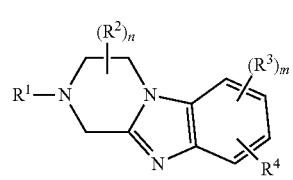

(I)

or a pharmaceutically acceptable salt thereof, wherein the variables are as defined in Sub-Section A.

In certain embodiments, the method reduces the amount of fat in a subject.

In certain embodiments, the method improves regulation of energy balance in the subject, lipid homeostatis, insulin sensitivity, blood pressure homeostatis, or vascular health of the subject.

In certain embodiments, the method reduces the amount of cholesterol in a subject.

In certain embodiments, the subject suffers from a cardiovascular disease. For example, in certain embodiments, the cardiovascular disease is coronary artery disease or peripheral vascular disease.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing the Amount of Mesenchymal Pre-adipocyte Stem Cell Precursors Another aspect of the invention provides a method of reducing the amount of mesenchymal pre-adipocyte stem cell precursors in a subject. The method comprises administering to a subject in need thereof an effective amount of a tetrahydrobenzo[4,5]imidazo[1,2-a]pyrazine organic compound described herein, such as a compound of Formula I described above in Sub-Section A, to reduce the amount of mesenchymal pre-adipocyte stem cell precursors in the subject. Formula I, as described above in Sub-Section A, is represented by:

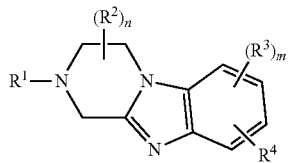
(I)

or a pharmaceutically acceptable salt thereof, wherein the variables are as defined in Sub-Section A.

In certain embodiments, the subject is an adult human.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Inducing Death of Adipocyte Cells

Another aspect of the invention provides a method of inducing the death of an adipocyte cell. The method comprises exposing an adipocyte cell to an effective amount of a tetrahydrobenzo[4,5]imidazo[1,2-a]pyrazine organic compound described herein, such as a compound of Formula I described above in Sub-Section A, to induce death of the adipocyte cell. Formula I, as described above in Sub-Section A, is represented by:

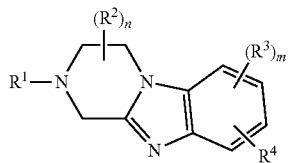
(I)

or a pharmaceutically acceptable salt thereof, wherein the variables are as defined in Sub-Section A.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

Methods of Reducing Skin Aging

Another aspect of the invention provides a method of reducing skin aging in a subject. The method comprises administering to a subject in need thereof an effective amount of a tetrahydrobenzo[4,5]imidazo[1,2-a]pyrazine organic compound described herein, such as a compound of Formula I described above in Sub-Section A, to reduce the effects of skin aging. Formula I, as described above in Sub-Section A, is represented by:

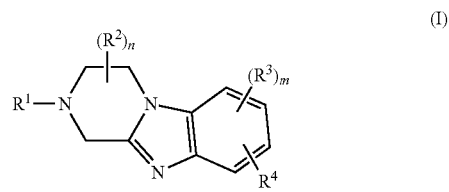
(I)

or a pharmaceutically acceptable salt thereof, wherein the variables are as defined in Sub-Section A.

In certain embodiments, the compound is one of the generic or specific compounds described in Sub-Section A, such as a compound of Formula I, a compound embraced by one of the further embodiments describing definitions for certain variables of Formula I, a compound of Formula I-A, or a compound embraced by one of the further embodiments describing definitions for certain variables of Formula I-A.

The description above describes multiple embodiments relating to various methods, such as methods of body contouring and/or reducing fat in a subject using certain tetrahydrobenzo[4,5]imidazo[1,2-a]pyrazine organic compounds. The patent application specifically contemplates all combinations of the embodiments. For example, the invention contemplates body contouring and/or reducing fat in a subject by administering a therapeutically effective amount of a compound of Formula I-A.

Combination Therapy

As indicated above, the invention embraces combination therapy, which includes the administration of a tetrahydrobenzo[4,5]imidazo[1,2-a]pyrazine organic compound described herein (such as compound of Formula I or I-A described above in Sub-Section A) and a second agent as part of a specific treatment regimen intended to provide the beneficial effect from the co-action of these therapeutic agents. The beneficial effect of the combination may include pharmacokinetic or pharmacodynamic co-action resulting from the combination of therapeutic agents.

C. Pharmaceutical Compositions Containing Tetrahydrobenzo[4,5]Imidazo[1,2-a]Pyrazine Organic Compounds The invention provides pharmaceutical compositions comprising a tetrahydrobenzo[4,5]imidazo[1,2-a]pyrazine organic compound described herein, such as a compound of Formula I or I-A described above in Sub-Section A, and a pharmaceutically acceptable carrier. In certain embodiments, the pharmaceutical compositions preferably comprise an effective amount of one or more of the tetrahydrobenzo[4,5]imidazo[1,2-a]pyrazine organic compounds described above (i.e., an amount effective to achieve one or more of the therapeutic applications described above in Sub-Section B), formulated together with one or more pharmaceutically acceptable carriers (additives) and/or diluents. As described in detail below in Section VI, pharmaceutical compositions of the present invention may be specially formulated for administration in solid or liquid form, including those adapted for the following: (1) parenteral administration by, for example, subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) oral administration, for example, drenches (aqueous or non-aqueous solutions or suspensions), tablets (e.g., those targeted for buccal, sublingual, and/or systemic absorption), boluses, powders, granules, pastes for application to the tongue; (4) intravaginally or intrarectally, for example, as a pessary, cream or foam; (5) sublingually; (6) occularly; (7) transdermally; or (8) nasally.

D. Medical Kits Containing Tetrahydrobenzo[4,5]Imidazo[1,2-a]Pyrazine Organic Compounds Another aspect of the invention provides a kit for body contouring and/or reducing the amount of fat in a subject. The kit comprises: i) instructions for body contouring and/or reducing the amount of fat in a subject (for example, modifying the contour of a subject's externally exposed body part containing fat; reducing the amount of subcutaneous fat in a subject; inducing retraction of dermal tissue or subcutaneous tissue in a subject; preventing the accumulation of fat in a subject; treating a disorder selected from the group consisting of an adipose tissue tumor (e.g., a lipoma), fat embolism, dyslipidemia, or fatty liver disease in a subject; reducing the amount of fat or cholesterol in a subject; and reducing the amount of mesenchymal pre-adipocyte stem cell precursors in a subject); and ii) a tetrahydrobenzo[4,5]imidazo[1,2-a]pyrazine organic compound described herein, such as a compound of Formula I described above in Sub-Section A. The kit may comprise one or more unit dosage forms containing an amount of a tetrahydrobenzo[4,5]imidazo[1,2-a]pyrazine organic compound described herein, such as a compound of Formula I described above in Sub-Section A, that is effective for body contouring and/or reduction of fat in a subject.

The description above describes multiple aspects and embodiments of the invention, including tetrahydrobenzo[4,5]imidazo[1,2-a]pyrazine organic compounds, compositions comprising tetrahydrobenzo[4,5]imidazo[1,2-a]pyrazine organic compounds, methods of using the tetrahydrobenzo[4,5]imidazo[1,2-a]pyrazine organic compounds, and kits. The patent application specifically contemplates all combinations and permutations of the aspects and embodiments. For example, the invention contemplates body contouring and/or reducing fat in a human patient by administering a therapeutically effective amount of a compound of Formula I-A described above in Sub-Section A. Further, for example, the invention contemplates a kit for body contouring and/or reduction of fat in a subject, the kit comprising instructions for body contouring and/or reducing fat in a subject and ii) a tetrahydrobenzo[4,5]imidazo[1,2-a]pyrazine organic compound described herein, such as a compound of Formula I-A described above in Sub-Section A.

VI. Pharmaceutical Compositions

The invention provides pharmaceutical compositions comprising a fused heterocyclic organic compound described herein and a pharmaceutically acceptable carrier. In certain embodiments, the pharmaceutical compositions preferably comprise an effective amount of one or more of the fused heterocyclic organic compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) parenteral administration by, for example, subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) oral administration, for example, drenches (aqueous or non-aqueous solutions or suspensions), tablets (e.g., those targeted for buccal, sublingual, and/or systemic absorption), boluses, powders, granules, pastes for application to the tongue; (4) intravaginally or intrarectally, for example, as a pessary, cream or foam; (5) sublingually; (6) occularly; (7) transdermally; or (8) nasally.

Particularly preferred pharmaceutical compositions are those formulated for injection, particularly subcutaneous injection. Such pharmaceutical compositions desirably comprise water and one or more excipients. Exemplary excipients include, for example, salts (e.g., sodium acetate, sodium chloride, sodium citrate, sodium phosphate, sodium sulfate, succinate, tris, phosphate buffered saline (i.e., PBS), and the like), amino acids (e.g., arginine, histidine, glycine, and the like), detergents (e.g., polysorbate 20, polysorbate 0, Triton X-100, and the like), carbohydrates (e.g., sucrose, trehalose, and the like), polyols (e.g., glycerol, sorbitol, and the like), cyclodextrins (e.g., 2-hydroxypropyl-beta-cyclodextrin, sulfobutyl ether beta-cyclodextrin, and the like), celluloses, liposomes, micelle forming agents (e.g., bile acids), polymeric carriers (e.g., polyesters, polyanhydrides, polyalkylene ethers such as polyethylene glycol and polyethylene glycol 400, and the like), propylene glycol, ethanol, dimethylsulfoxide (DMSO), and dimethylacetamide (DMA).

In certain embodiments, the pharmaceutical composition is formulated for reducing the amount of fat in a subject. In certain other embodiments, the pharmaceutical composition is formulated for reducing the amount of subcutaneous fat in a subject.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration.

The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

The preparations of the present invention may be given parenterally, topically, orally, or rectally. They are of course given in forms suitable for each administration route. For example, they are administered in tablets or capsule form; by injection, infusion or inhalation; topically by lotion or ointment; and rectally by suppositories.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5)

solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

The description above describes multiple aspects and embodiments of the invention, including fused heterotricyclic organic compounds, compositions comprising fused heterocyclic organic compounds, methods of using the fused heterocyclic organic compounds, and kits. The patent application specifically contemplates all combinations and permutations of the aspects and embodiments. For example, the invention contemplates body contouring and/or reducing fat in a human patient by administering a therapeutically effective amount of a compound of Formula I-A in Section II, Sub-Section A. Further, for example, the invention contemplates a kit for body contouring and/or reduction of fat in a subject, the kit comprising instructions for body contouring and/or reducing fat in a subject and ii) a fused heterotricyclic organic compound described herein, such as a compound of Formula I-A in Section II, Sub-Section A.

EXAMPLES

The invention now being generally described, will be more readily understood by reference to the following examples, which are included merely for purposes of illustration of certain aspects and embodiments of the present invention, and are not intended to limit the invention.

Example 1

Evaluation of Adipocyte Cell Cytotoxicity for Exemplary Fused Heterotricyclic Organic Compounds Exemplary fused heterotricyclic organic compounds of the invention were evaluated for adipocyte cell cytotoxicity using a cell viability/cytotoxicity assay commercially available from Molecular Probes, located in Eugene Oreg.

Materials and Methods

Adipocytes were maintained using standard cell culture procedures. Approximately, 1-2 million cells/mL were incubated with 10 mg/mL of test compound or control at 37° C. for varying amounts of time up to 24 hours. Following incubation with a test compound or control, aliquots of cells in solution were transferred to a 96-well microplate and prepared according to the manufacturer's instructions. Cells were exposed to calcein AM and ethidium homodimer-1, each purchased from Molecular Probes. Following incubation of the cells in presence of calcein AM and ethidium homodimer-1, the fluorescence signal of calcein and ethidium was then measured using a SpectraMax Multi-Mode Microplate Reader using optical filters and excitation and emission wavelengths of 494 nm/517 nm and 528 nm/617 nm for calcein and ethidium bromide, respectively. Test compounds listed in Table 5 below were purchased from a commercial vendor.

Results and Discussion

The time dependent effects of test compounds on both cell viability and cell toxicity were evaluated using a fluorescence assay that measures plasma membrane integrity and intracellular enzyme activity. Briefly, live cells are determined by the increased fluorescence signal of calcein AM upon enzymatic conversion. In contrast, the ethidium fluorescence signal is dramatically increased upon entering a cell with damaged membranes and binding to nucleic acids. The ratio of ethidium to calcein fluorescence can also be used to measure the relative amount of live and dead cells.

The ethidium signal was used as a measure of cell death following the protocols outlined by the assay manufacturer.

The cell membrane disruption effects of various test compounds were compared to the known cytotoxic compound deoxycholic acid (DC), and the combination of phosphatidylcholine and deoxycholic acid (PC/DC) (i.e., as positive controls). Saline was used as a negative control. All compounds were incubated with approximately 1-2 million cells/mL for varying amounts of time to induce cell death and/or disrupt membrane integrity. The compounds tested showed a gradient of cell membrane disruption and cell death as a function of time. All test compounds induced some degree of cell death that continued overnight. Fused heterotricyclic organic compounds tested in the assay are shown in Table 5 below, along with their compound identification number.

TABLE 5

| Compound No. | Chemical Structure |
|---|---|
| II-1 | (structure) |
| II-2 | (structure) |
| II-3 | (structure) |
| II-4 | (structure) |
| II-5 | (structure) |
| II-6 | (structure) |
| II-7 | (structure) |

Example 2

Evaluation of Adipocyte Cell Cytotoxicity for Exemplary Dipyrido-pyrimidinone Organic Compounds Exemplary dipyrido-pyrimidinone compounds of the invention were evaluated for adipocyte cell cytotoxicity using a cell viability/cytotoxicity assay commercially available from Molecular Probes, located in Eugene Oreg.

Materials and Methods

Adipocytes were maintained using standard cell culture procedures. Approximately, 1-2 million cells/mL were incubated with either 10 or 15 mg/mL of test compound or control at 37° C. for varying amounts of time up to 24 hours. Following incubation with a test compound or control, aliquots of cells in solution were transferred to a 96-well microplate and prepared according to the manufacturer's instructions. Cells were exposed to calcein AM and ethidium homodimer-1, each purchased from Molecular Probes. Following incubation of the cells in presence of calcein AM and ethidium homodimer-1, the fluorescence signal of calcein and ethidium was then measured using a SpectraMax Multi-Mode Microplate Reader using optical filters and excitation and emission wavelengths of 494 nm/517 nm and 528 nm/617 nm for calcein and ethidium bromide, respectively.

Results and Discussion

The time dependent effects of test compounds on both cell viability and cell toxicity were evaluated using a fluorescence assay that measures plasma membrane integrity and intracellular enzyme activity. Briefly, live cells are determined by the increased fluorescence signal of calcein AM upon enzymatic conversion. In contrast, the ethidium fluorescence signal is dramatically increased upon entering a cell with damaged membranes and binding to nucleic acids. The ratio of ethidium to calcein fluorescence can also be used to measure the relative amount of live and dead cells. The ethidium signal was used as a measure of cell death following the protocols outlined by the assay manufacturer. Test compounds listed in Table 6 below were purchased from a commercial vendor.

Figure 3:
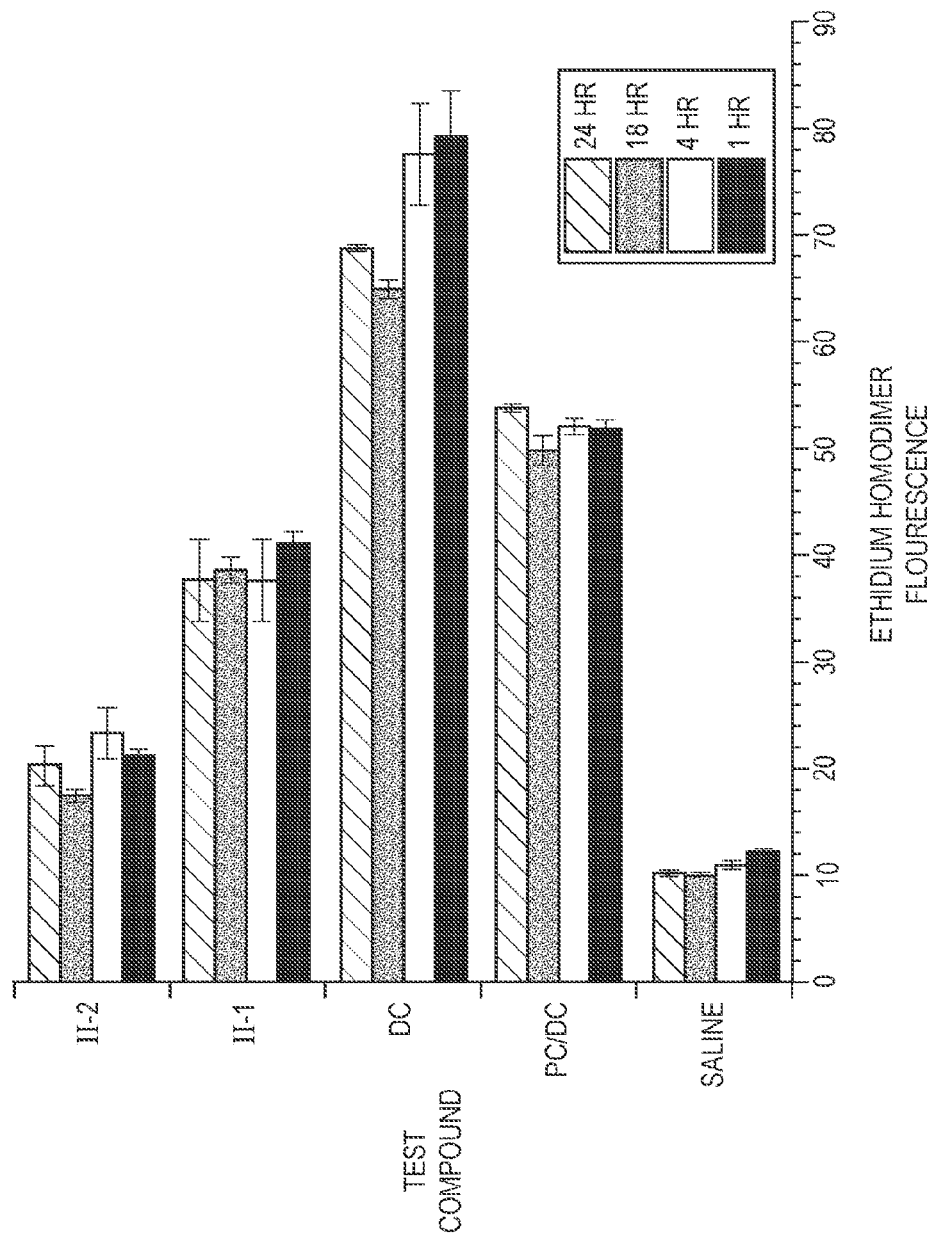
FIG. 3 is a histogram profile showing ethidium homodimer fluorescence intensity when adipocytes are incubated with 10 mg/mL of test compound or control for 1 hr, 4 hrs, 18 hrs, or 24 hrs, as described in Example 2.
Figure 4:
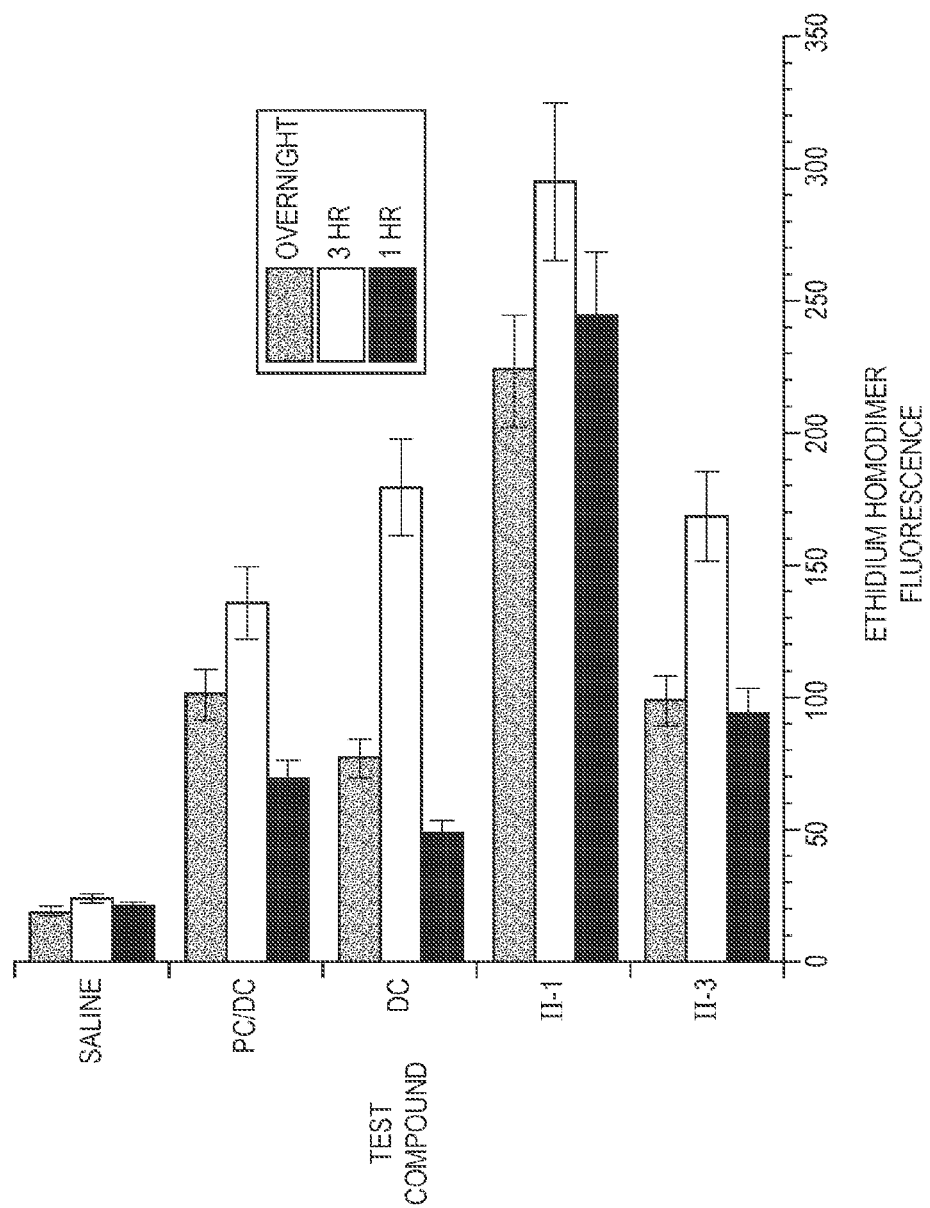
FIG. 4 is a histogram profile showing ethidium homodimer fluorescence intensity when adipocytes are incubated with 15 mg/mL of test compound or control for 1 hr, 3 hrs, or overnight, as described in Example 2.

The cell membrane disruption effects of various test compounds were compared to the known cytotoxic compounds deoxycholic acid (DC), and the combination of phosphatidylcholine and deoxycholic acid (PC/DC) (i.e., as positive controls). Saline was used as a negative control. All compounds were incubated with approximately 1-2 million cells/mL for varying amounts of time to induce cell death and/or disrupt membrane integrity. The compounds tested showed a gradient of cell membrane disruption and cell death as a function of time. All tested contemplated compounds induced some degree of cell death that continued for at least 24 hrs. However, at 10 mg/mL, the test compounds were initially less aggressive than DC or PC/DC (FIG. 3). Increasing the concentration of test compound to 15 mg/mL nonlinearly influenced the compound's cell killing behavior (FIG. 4). Dipyrido-pyrimidinone organic compounds tested in the assay are shown in Table 6 below, along with their compound identification number.

TABLE 6

| Compound No. | Chemical Structure |
| --- | --- |
| II-1 | (structure) |
| II-2 | (structure) |
| II-3 | (structure) |

Example 3

Evaluation of Adipocyte Cell Cytotoxicity for Exemplary Tetrahydropyrimido-furo-isoquinolinone Organic Compounds Exemplary tetrahydropyrimido-furo-isoquinolinone compounds of the invention were evaluated for adipocyte cell cytotoxicity using a cell viability/cytotoxicity assay commercially available from Molecular Probes, located in Eugene Oreg. Experimental procedures were analogous to those described in Example 1.

Figure 5:
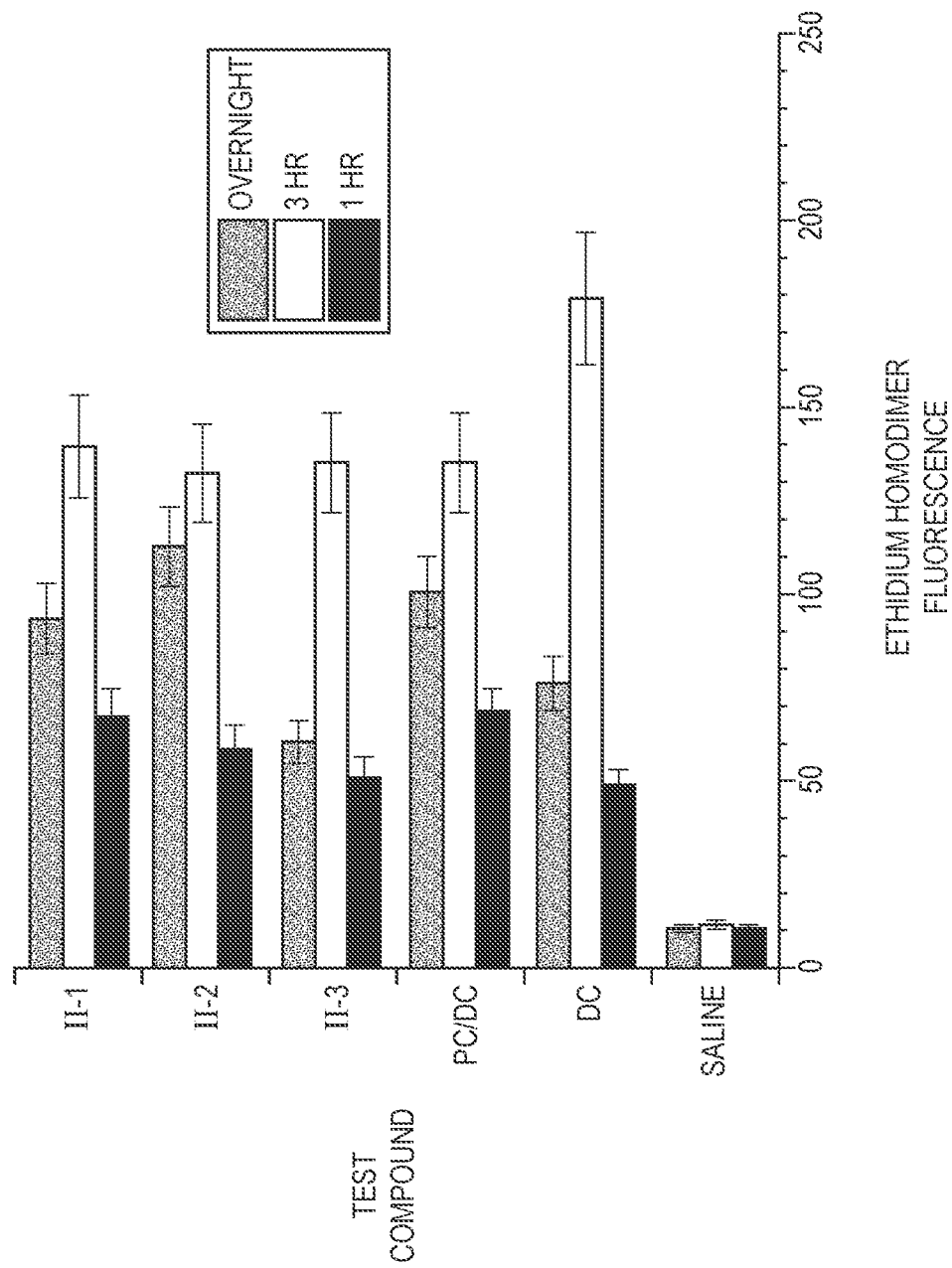
FIG. 5 is a histogram profile showing ethidium homodimer fluorescence intensity when adipocytes are incubated with 10 mg/mL of test compound or control for 1 hr, 3 hrs, or overnight, as described in Example 3.

All test compounds were incubated with approximately 1-2 million cells/mL for varying amounts of time to induce cell death and/or disrupt membrane integrity. The compounds tested showed a gradient of cell membrane disruption and cell death as a function of time. All tested compounds induced some degree of cell death that continued overnight (FIG. 5). Tetrahydropyrimido-furo-isoquinolinone organic compounds tested in the assay are shown in Table 7 below, along with their compound identification number.

TABLE 7

| Compound No. | Chemical Structure |
| --- | --- |
| II-1 | (structure) |
| II-2 | (structure) |
| II-3 | (structure) |

Example 4

Evaluation of Adipocyte Cell Cytotoxicity for Exemplary Tetrahydrobenzo[4,5]Imidazo[1,2-a]Pyrazine Organic Compounds Exemplary tetrahydrobenzo[4,5]imidazo[1,2-a]pyrazine compounds of the invention were evaluated for adipocyte cell cytotoxicity using a cell viability/cytotoxicity assay commercially available from Molecular Probes, located in Eugene Oreg. Experimental procedures were analogous to those described in Example 1.

Figure 6:
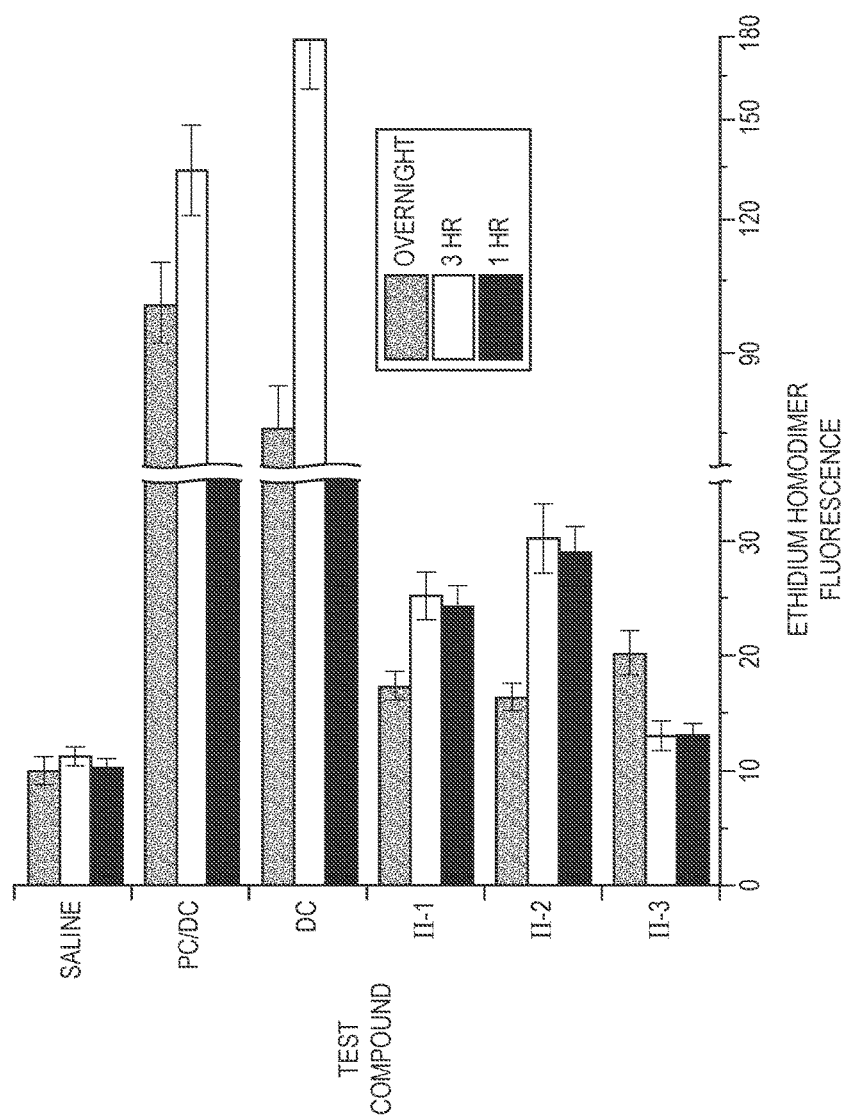
FIG. 6 is a histogram profile showing ethidium homodimer fluorescence intensity when adipocytes are incubated with 10 mg/mL of test compound or control for 1 hr, 3 hrs, or overnight, as described in Example 4.

All test compounds were incubated with approximately 1-2 million cells/mL for varying amounts of time to induce cell death and/or disrupt membrane integrity. The compounds tested showed a gradient of cell membrane disruption and cell death as a function of time. Deoxycholic acid was the most aggressive cell killing compound tested, which correlates with the highest ethidium signal over time. All tested compounds induced some degree of cell death that continued overnight (FIG. 6). Tetrahydrobenzo[4,5]imidazo[1,2-a]pyrazine organic compounds tested in the assay are shown in Table 8 below, along with their compound identification number.

TABLE 8

| Compound No. | Chemical Structure |
|---|---|
| II-1 | 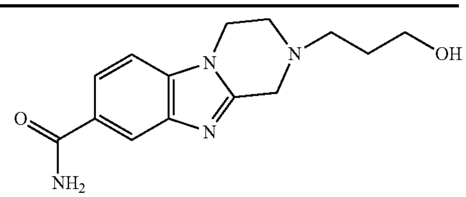 |
| II-2 | 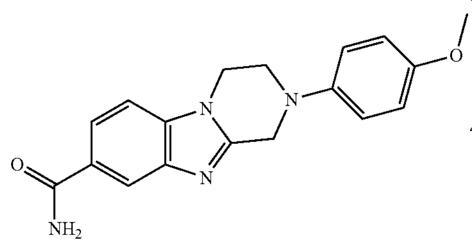 |
| II-3 | 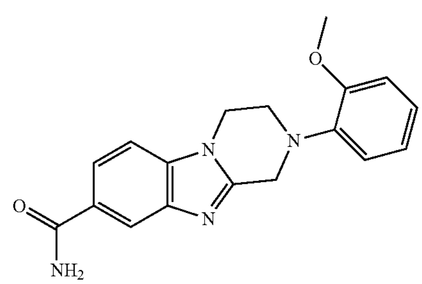 [SMILES: COc1ccccc1N1CCn2c(nc3cc(C(N)=O)ccc32)C1] |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A cosmetic method of modifying the contour of a subject's externally exposed body part containing fat, the method comprising administering to said body part an amount of a compound of Formula I effective to modify the contour of said body part, wherein Formula I is represented by:

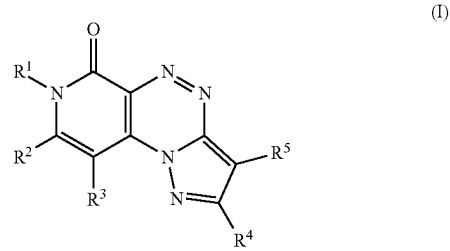

(I)

or a pharmaceutically acceptable salt thereof; wherein:
$R^1$ is —$(C_1-C_6)$alkylene-$X^1$, —$(C_3-C_6)$cycloalkyl-$X^1$, —$CO_2R^6$, —$C(O)R^6$, —OH, or —$N(R^6)C(O)$—$(C_1-C_6)$alkyl;
$X^1$ is —$CO_2R^6$, —$C(O)R^6$, —$C(O)N(R^7)R^6$, —$N(R^7)C(O)R^6$, or —$OR^6$;
$R^2$ and $R^3$ each represent independently hydrogen or —$(C_1-C_6)$alkyl;
$R^4$ is hydrogen, —$(C_1-C_6)$alkyl, —$(C_3-C_7)$cycloalkyl, —$(C_1-C_6)$alkoxy, or —$(C_3-C_7)$cycloalkoxy;
$R^5$ is phenyl, 5-6 membered heteroaryl, —$(C_3-C_7)$cycloalkyl, —$(C_1-C_6)$alkoxy, or aralkyl, each of which is optionally substituted with 1, 2, or 3 substituents independently selected from the group consisting of halogen, —$(C_1-C_6)$alkyl, —$(C_3-C_5)$cycloalkyl, hydroxyl, and —$(C_1-C_6)$alkoxy; or $R_5$ is hydrogen or —$(C_1-C_6)$alkyl; and
$R^6$ and $R^7$ each represent independently hydrogen or —$(C_1-C_6)$alkyl.

2. The method of claim 1, wherein the body part is the subject's face, neck, chin, submental region, arm, thigh, knee, calf, buttocks, hips, or abdomen.

3. The method of claim 1, wherein the body part is the subject's face.

4. The method of claim 1, wherein the body part is the subject's neck or submental region.

5. The method of claim 1, wherein the subject experiences at least a 5% by weight reduction in the amount of fat in the subject's body part exposed to said compound.

6. The method of claim 1, wherein the subject experiences at least a 15% by weight reduction in the amount of fat in the subject's body part exposed to said compound.

7. The method of claim 1, wherein the administering comprises injecting said compound into said body part.

8. A method selected from:
(a) a method of reducing the amount of subcutaneous fat in a subject, comprising exposing subcutaneous fat in a subject to an effective amount of a compound of Formula I to reduce the amount of subcutaneous fat in said subject, wherein Formula I is represented by:

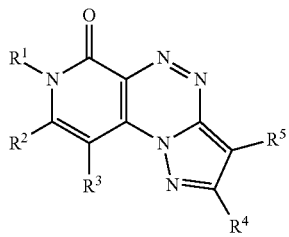

(I)

or a pharmaceutically acceptable salt thereof; wherein:
R¹ is —(C₁-C₆)alkylene-X¹, —(C₃-C₆)cycloalkyl-X¹, —CO₂R⁶, —C(O)R⁶, —OH, or —N(R⁶)C(O)—(C₁-C₆)alkyl;
X¹ is —CO₂R⁶, —C(O)R⁶, —C(O)N(R⁷)R⁶, —N(R⁷)C(O)R⁶, or —OR⁶;
R² and R³ each represent independently hydrogen or —(C₁-C₆)alkyl;
R⁴ is hydrogen, —(C₁-C₆)alkyl, —(C₃-C₇)cycloalkyl, —(C₁-C₆)alkoxy, or —(C₃-C₇)cycloalkoxy;
R⁵ is phenyl, 5-6 membered heteroaryl, —(C₃-C₇)cycloalkyl, —(C₁-C₆)alkoxy, or aralkyl, each of which is optionally substituted with 1, 2, or 3 substituents independently selected from the group consisting of halogen, —(C₁-C₆)alkyl, —(C₃-C₅)cycloalkyl, hydroxyl, and —(C₁-C₆)alkoxy; or R₅ is hydrogen or —(C₁-C₆)alkyl; and
R⁶ and R⁷ each represent independently hydrogen or —(C₁-C₆)alkyl;

(b) a method for inducing retraction of dermal tissue in a subject, comprising administering an effective amount of a compound of Formula I to dermal tissue of a subject to induce retraction of dermal tissue, wherein Formula I is represented by:

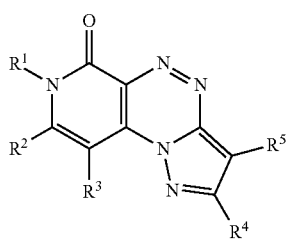

(I)

or a pharmaceutically acceptable salt thereof; wherein:
R¹ is —(C₁-C₆)alkylene-X¹, —(C₃-C₆)cycloalkyl-X¹, —CO₂R⁶, —C(O)R⁶, —OH, or —N(R⁶)C(O)—(C₁-C₆)alkyl;
X¹ is —CO₂R⁶, —C(O)R⁶, —C(O)N(R⁷)R⁶, —N(R⁷)C(O)R⁶, or —OR⁶;
R² and R³ each represent independently hydrogen or —(C₁-C₆)alkyl;
R⁴ is hydrogen, —(C₁-C₆)alkyl, —(C₃-C₇)cycloalkyl, —(C₁-C₆)alkoxy, or —(C₃-C₇)cycloalkoxy;
R⁵ is phenyl, 5-6 membered heteroaryl, —(C₃-C₇)cycloalkyl, —(C₁-C₆)alkoxy, or aralkyl, each of which is optionally substituted with 1, 2, or 3 substituents independently selected from the group consisting of halogen, —(C₁-C₆)alkyl, —(C₃-C₅)cycloalkyl, hydroxyl, and —(C₁-C₆)alkoxy; or R₅ is hydrogen or —(C₁-C₆)alkyl; and
R⁶ and R⁷ each represent independently hydrogen or —(C₁-C₆)alkyl;

(c) a method for inducing retraction of subcutaneous tissue in a subject, comprising administering an effective amount of a compound of Formula I to subcutaneous tissue of a subject to induce retraction of subcutaneous tissue, wherein Formula I is represented by:

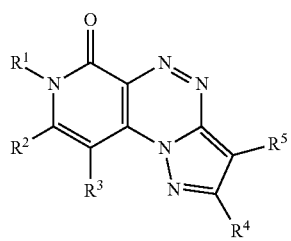

(I)

or a pharmaceutically acceptable salt thereof; wherein:
R¹ is —(C₁-C₆)alkylene-X¹, —(C₃-C₆)cycloalkyl-X¹, —CO₂R⁶, —C(O)R⁶, —OH, or —N(R⁶)C(O)—(C₁-C₆)alkyl;
X¹ is —CO₂R⁶, —C(O)R⁶, —C(O)N(R⁷)R⁶, —N(R⁷)C(O)R⁶, or —OR⁶;
R² and R³ each represent independently hydrogen or —(C₁-C₆)alkyl;
R⁴ is hydrogen, —(C₁-C₆)alkyl, —(C₃-C₇)cycloalkyl, —(C₁-C₆)alkoxy, or —(C₃-C₇)cycloalkoxy;
R⁵ is phenyl, 5-6 membered heteroaryl, —(C₃-C₇)cycloalkyl, —(C₁-C₆)alkoxy, or aralkyl, each of which is optionally substituted with 1, 2, or 3 substituents independently selected from the group consisting of halogen, —(C₁-C₆)alkyl, —(C₃-C₅)cycloalkyl, hydroxyl, and —(C₁-C₆)alkoxy; or R₅ is hydrogen or —(C₁-C₆)alkyl; and
R⁶ and R⁷ each represent independently hydrogen or —(C₁-C₆)alkyl;

(f) a method of reducing the amount of fat or cholesterol in a subject, comprising administering to a subject in need thereof an effective amount of a compound of Formula I to reduce the amount of fat or cholesterol in the subject, wherein Formula I is represented by:

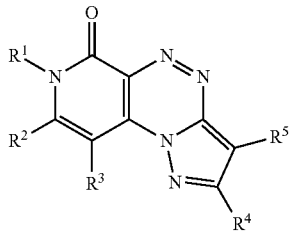

(I)

or a pharmaceutically acceptable salt thereof; wherein:
R¹ is —(C₁-C₆)alkylene-X¹, —(C₃-C₆)cycloalkyl-X¹, —CO₂R⁶, —C(O)R⁶, —OH, or —N(R⁶)C(O)—(C₁-C₆)alkyl;

$X^1$ is —$CO_2R^6$, —$C(O)R^6$, —$C(O)N(R^7)R^6$, —$N(R^7)C(O)R^6$, or —$OR^6$;

$R^2$ and $R^3$ each represent independently hydrogen or —$(C_1-C_6)$alkyl;

$R^4$ is hydrogen, —$(C_1-C_6)$alkyl, —$(C_3-C_7)$cycloalkyl, —$(C_1-C_6)$alkoxy, or —$(C_3-C_7)$cycloalkoxy;

$R^5$ is phenyl, 5-6 membered heteroaryl, —$(C_3-C_7)$cycloalkyl, —$(C_1-C_6)$alkoxy, or aralkyl, each of which is optionally substituted with 1, 2, or 3 substituents independently selected from the group consisting of halogen, —$(C_1-C_6)$alkyl, —$(C_3-C_5)$cycloalkyl, hydroxyl, and —$(C_1-C_6)$alkoxy; or $R_5$ is hydrogen or —$(C_1-C_6)$alkyl; and $R^6$ and $R^7$ each represent independently hydrogen or —$(C_1-C_6)$alkyl;

(g) a method of reducing the amount of mesenchymal pre-adipocyte stem cell precursors in a subject, comprising administering to a subject in need thereof an effective amount of a compound of Formula I to reduce the amount of mesenchymal pre-adipocyte stem cell precursors in the subject, wherein Formula I is represented by:

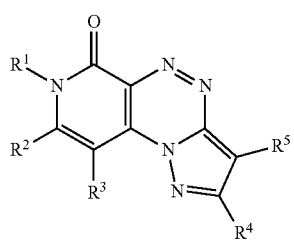

(I)

or a pharmaceutically acceptable salt thereof; wherein:

$R^1$ is —$(C_1-C_6)$alkylene-$X^1$, —$(C_3-C_6)$cycloalkyl-$X^1$, —$CO_2R^6$, —$C(O)R^6$, —OH, or —$N(R^6)C(O)$—$(C_1-C_6)$alkyl;

$X^1$ is —$CO_2R^6$, —$C(O)R^6$, —$C(O)N(R^7)R^6$, —$N(R^7)C(O)R^6$, or —$OR^6$;

$R^2$ and $R^3$ each represent independently hydrogen or —$(C_1-C_6)$alkyl;

$R^4$ is hydrogen, —$(C_1-C_6)$alkyl, —$(C_3-C_7)$cycloalkyl, —$(C_1-C_6)$alkoxy, or —$(C_3-C_7)$cycloalkoxy;

$R^5$ is phenyl, 5-6 membered heteroaryl, —$(C_3-C_7)$cycloalkyl, —$(C_1-C_6)$alkoxy, or aralkyl, each of which is optionally substituted with 1, 2, or 3 substituents independently selected from the group consisting of halogen, —$(C_1-C_6)$alkyl, —$(C_3-C_5)$cycloalkyl, hydroxyl, and —$(C_1-C_6)$alkoxy; or $R_5$ is hydrogen or —$(C_1-C_6)$alkyl; and $R^6$ and $R^7$ each represent independently hydrogen or —$(C_1-C_6)$alkyl.

9. The method of claim 1, wherein the subject is an adult human.

10. The method of claim 1, wherein the compound is a compound of Formula I-A:

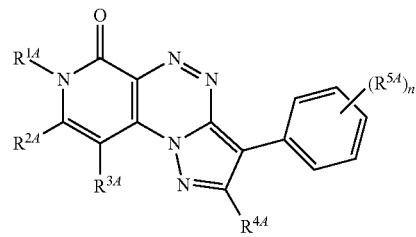

(I-A)

or a pharmaceutically acceptable salt thereof; wherein:

$R^{1A}$ is —$(C_1-C_6)$alkylene-$CO_2R^{6A}$, —$(C_3-C_6)$cycloalkyl-$CO_2R^{6A}$, —$(C_1-C_6)$alkylene-O—$(C_1-C_6)$alkyl, or —$(C_3-C_6)$cycloalkyl-O—$(C_1-C_6)$alkyl;

$R^{2A}$ and $R^{3A}$ each represent independently hydrogen or methyl;

$R^{4A}$ is hydrogen or —$(C_1-C_6)$alkyl;

$R^{5A}$ represents independently for each occurrence hydrogen, halogen, or —$(C_1-C_6)$alkyl;

$R^{6A}$ is hydrogen or —$(C_1-C_6)$alkyl, and n is 1, 2, or 3.

11. The method of claim 1, wherein the compound is one of the following or a pharmaceutically acceptable salt thereof:

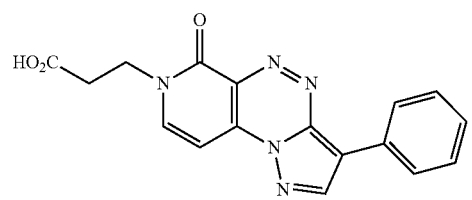

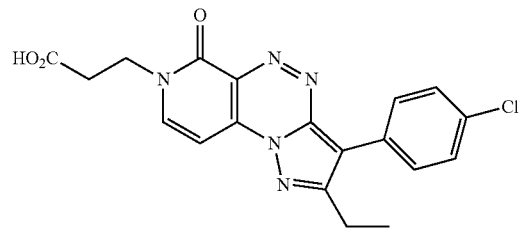

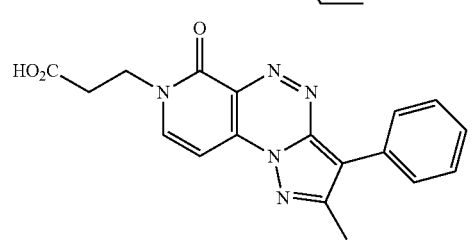

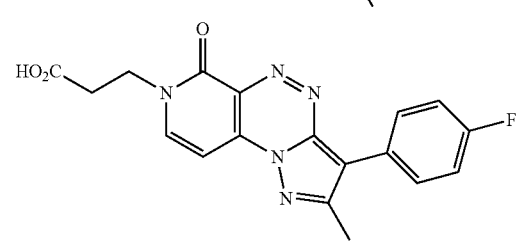

-continued
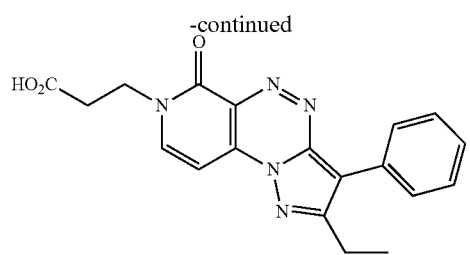
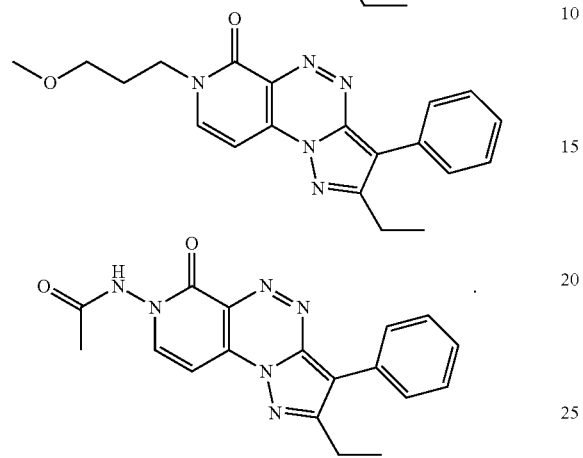
* * * * *